US012612462B2

(12) United States Patent
Bruse et al.

(10) Patent No.: US 12,612,462 B2
(45) Date of Patent: Apr. 28, 2026

(54) TREATMENT AND INHIBITION OF INFLAMMATORY LUNG DISEASES IN PATIENTS HAVING RISK ALLELES IN THE GENES ENCODING IL33 AND IL1RL1

(71) Applicant: Regeneron Pharmaceuticals, Inc., Tarrytown, NY (US)

(72) Inventors: Shannon Bruse, Tarrytown, NY (US); Shane McCarthy, Tarrytown, NY (US); Aris Baras, Tarrytown, NY (US); Frederick Dewey, Tarrytown, NY (US); Omri Gottesman, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 279 days.

(21) Appl. No.: 18/330,736

(22) Filed: Jun. 7, 2023

(65) Prior Publication Data

US 2023/0374145 A1 Nov. 23, 2023

Related U.S. Application Data

(63) Continuation of application No. 16/599,709, filed on Oct. 11, 2019, now Pat. No. 11,708,415, which is a continuation of application No. PCT/US2018/023266, filed on Mar. 20, 2018.

(60) Provisional application No. 62/485,077, filed on Apr. 13, 2017.

(51) Int. Cl.
| | |
|---|---|
| *A61K 39/00* | (2006.01) |
| *A61P 11/00* | (2006.01) |
| *A61P 11/06* | (2006.01) |
| *C07K 16/28* | (2006.01) |
| *C12Q 1/6883* | (2018.01) |
| *C07K 16/24* | (2006.01) |

(52) U.S. Cl.
CPC .......... *C07K 16/2866* (2013.01); *A61P 11/00* (2018.01); *A61P 11/06* (2018.01); *C12Q 1/6883* (2013.01); *A61K 2039/507* (2013.01); *C07K 16/244* (2013.01); *C07K 2317/76* (2013.01); *C12Q 2600/106* (2013.01); *C12Q 2600/112* (2013.01); *C12Q 2600/156* (2013.01)

(58) Field of Classification Search
CPC ................... A61K 39/395; A61K 2039/55527
See application file for complete search history.

(56) References Cited

U.S. PATENT DOCUMENTS

| | | | |
|---|---|---|---|
| 7,186,809 | B2 | 3/2007 | Pluenneke |
| 7,452,980 | B2 | 11/2008 | Kingsbury et al. |
| 7,605,237 | B2 | 10/2009 | Stevens et al. |
| 7,608,693 | B2 | 10/2009 | Martin et al. |
| 7,638,606 | B2 | 12/2009 | Carter et al. |
| 8,092,804 | B2 | 1/2012 | Eriksson et al. |
| 8,187,596 | B1 | 5/2012 | Chackerian et al. |
| 8,444,987 | B2 | 5/2013 | Kingsbury et al. |
| 8,679,487 | B2 | 3/2014 | Armitage et al. |
| 8,877,189 | B2 | 11/2014 | Eriksson et al. |
| 9,290,574 | B2 | 3/2016 | Kostic et al. |
| 9,453,072 | B2 | 9/2016 | Murphy et al. |
| 11,708,415 | B2 * | 7/2023 | Bruse ...................... A61P 11/00 424/139.1 |
| 2010/0160802 | A1 | 6/2010 | Gudbjartsson et al. |
| 2013/0253847 | A1 | 9/2013 | Gudbjartsson et al. |
| 2014/0271642 | A1 | 9/2014 | Murphy et al. |
| 2014/0271658 | A1 | 9/2014 | Murphy |
| 2015/0320021 | A1 | 11/2015 | Wang et al. |
| 2015/0320022 | A1 | 11/2015 | Wang et al. |
| 2016/0168242 | A1 | 6/2016 | Hass et al. |
| 2016/0168640 | A1 | 6/2016 | Khosla et al. |
| 2017/0096483 | A1 | 4/2017 | Orengo et al. |
| 2018/0155436 | A1 | 6/2018 | Orengo et al. |

FOREIGN PATENT DOCUMENTS

| | | |
|---|---|---|
| EP | 1725261 | 11/2006 |
| EP | 2928916 | 10/2015 |
| WO | 2011031600 | 3/2011 |
| WO | 2012113813 | 8/2012 |
| WO | 2013165894 | 11/2013 |
| WO | 2013173761 | 11/2013 |
| WO | 2014031610 | 2/2014 |
| WO | 2014152195 | 9/2014 |
| WO | 2016077675 | 5/2015 |
| WO | 2015099175 | 7/2015 |
| WO | 2015106080 | 7/2015 |
| WO | 2015127229 | 8/2015 |
| WO | 2016077366 | 5/2016 |
| WO | 2016077381 | 5/2016 |

(Continued)

OTHER PUBLICATIONS

Meigs et al., "Genotype Score in Addition to Common Risk Factors for Prediction of Type 2 Diabetes", New England Journal of Medicine, 2008, 359(21), pp. 2208-2219.
Buysschaert et al., "Genetic evidence for a role of IL33 in nasal polyposis", Allergy, 2010, 65, pp. 616-622.
March et al., "Genome-wide association studies in asthma: progress and pitfalls", Advances in Genomics and Genetics, 2015, 5, pp. 107-119.
Corren et al., "A randomized, controlled, phase 2 study of AMG 317, an IL-4Ralpha antagonist, in patients with asthma", Am J Respir Crit Care Med, 2010, 181(8), pp. 788-796.

(Continued)

*Primary Examiner* — Prema M Mertz
(74) *Attorney, Agent, or Firm* — Armstrong Teasdale LLP

(57) ABSTRACT

IL33 antagonists alone or in combination with IL-4R antagonists can be used to treat or inhibit eosinophilic asthma, eosinophilic COPD, eosinophilic ACOS, and nasal polyps in a subject having one or more risk alleles in the intronic IL1RL1 variant rs1420101, in the IL33 variant rs1342326, in both, or in variants in linkage disequilibrium thereof.

12 Claims, 24 Drawing Sheets

Specification includes a Sequence Listing.

(56)                    References Cited

FOREIGN PATENT DOCUMENTS

WO          2016156440          10/2016

OTHER PUBLICATIONS

Grotenboer et al., "Decoding asthma: Translating genetic variation in IL33 and IL1RL1 into disease pathophysiology", Journal of Allergy and Clinical Immunology, 2013, 131(3), pp. 856-865.

Meyers et al., "The Genetics of Asthma: Towards a Personalised Approach to Diagnosis and Treatment", The Lancet, 2014, 2(5), pp. 405-415.

Ramasamy et al., "Genome-Wide Association Studies of Asthma in Population-Based Cohorts Confirm Known and Suggested Loci and Identify an Additional Association near HLA", PLOS ONE, 2012, 7(9), pp e44008.

Tulah et al., "Defining the contribution of SNPs identified in asthma GWAS to clinical variables in asthmatic children", BMC Medical Genetics, Biomed Central, 2013, 14(1), pp. 100.

International Search Report and Written Opinion for PCT Application PCT/2018/023266 (189238.01102 (3022) (10340WO01)).

Chung et al., "Targeting the interleukin pathway in the treatment of asthma", Lancet, 2015, 386, pp. 1086-1094.

Moffatt et al., "A Large-Scale, Consortium-Based Genomewide Association Study of Asthma", NEJM, 2010, 363, pp. 1211-1221.

Tomkinson et al., "A Murine IL-4 Receptor Antagonist That Inhibits IL-4 and IL-13-Induced Responses Prevents Antigen-Induced Airway Eosinophilia and Airway Hyperresponsiveness", J Immunol, 2001, 166, pp. 5792-5800.

Kim et al., "Factors associated with plasma IL-33 levels in patients with chronic obstructive pulmonary disease", International Journal of COPD, 2017, 12, pp. 395-402.

Wenzel, "Asthma phenotypes: the evolution from clinical to molecular approaches", Nature Medicine, 2012, 18(5), pp. 716-725.

Meijer et al., "Neutrophils and emerging targets for treatment in chronic obstructive pulmonary disease", Expert Rev Clin Immunol, 2013, 9(11), pp. 1055-1068.

Lea et al., "The effect of peroxisome proliferator-activated receptor-gamma ligands on in vitro and in vivo models of COPD", Eur Respir J, 2014, 43, pp. 409-420.

* cited by examiner

B

| Gene | SNP | Group | N (AAF) | Beta (95% CI) | | P-value |
|------|-----|-------|---------|---------------|---|---------|
| IL33 | rs1342326 | GSA | 20736 (0.17) | 0.0138 (0.0072-0.0204) | | 4.0e-05 |
| | | OMNI | 46040 (0.16) | 0.0151 (0.0108-0.0195) | | 6.0e-12 |
| | | Meta | 66776 (0.16) | 0.0147 (0.0111-0.0184) | | 1.6e-15 |
| IL1RL1 | rs1420101 | GSA | 20735 (0.37) | 0.0142 (0.0091-0.0193) | | 5.0e-08 |
| | | OMNI | 46041 (0.37) | 0.0179 (0.0145-0.0212) | | 8.9e-26 |
| | | Meta | 66776 (0.37) | 0.0168 (0.014-0.0195) | | 3.8e-32 |
| IL33 | rs146597587 | xGEN | 20950 (0.0031) | -0.03 (-0.0741-0.0142) | | 1.8e-01 |
| | | VCRome | 47851 (0.0029) | -0.0585 (-0.0879--0.0292) | | 9.4e-05 |
| | | Meta | 68801 (0.0029) | -0.0497 (-0.0742--0.0253) | | 6.8e-05 |

C

| Group | Sum | Num (AAF) | Beta (95% CI) | P-value |
|---|---|---|---|---|
| Meta | 0 | 18637 | | |
| | 1 | 29006 (0.61) | 0.0055 (0.0034-0.0075) | 1.7e-07 |
| | 2 | 15521 (0.45) | 0.0057 (0.0048-0.0071) | 1.3e-20 |
| | 3 | 3332 (0.15) | 0.0071 (0.0057-0.0085) | 8.8e-24 |
| | 4 | 235 (0.01) | 0.0053 (0.0021-0.0092) | 0.0034 |
| Allelic | | 66731 | 0.0067 (0.0054-0.0074) | 1e-39 |

A) Asthma

| Gene | SNP | Group | NumCases (AAF) | NumCtrls (AAF) | OR (95% CI) | | P-value |
|------|-----|-------|----------------|----------------|-------------|---|---------|
| IL33 | rs1342326 | GSA | 3911 (0.16) | 20814 (0.16) | 1.11 (1.04-1.19) | | 1.1e-03 |
| | | OMNI | 8813 (0.17) | 37183 (0.16) | 1.08 (1.03-1.12) | | 1.2e-03 |
| | | Meta | 12824 (0.16) | 58007 (0.16) | 1.09 (1.05-1.13) | | 6.0e-06 |
| IL1RL1 | rs1420101 | GSA | 3911 (0.38) | 20815 (0.37) | 1.07 (1.02-1.13) | | 5.6e-03 |
| | | OMNI | 8909 (0.38) | 37207 (0.38) | 1.07 (1.04-1.11) | | 4.3e-05 |
| | | Meta | 12820 (0.38) | 58022 (0.37) | 1.07 (1.04-1.1) | | 8.2e-07 |
| IL33 | rs146597587 | xGEN | 3874 (0.002) | 21150 (0.0033) | 0.59 (0.35-1) | | 4.9e-02 |
| | | VCRome | 9292 (0.0027) | 36804 (0.003) | 0.92 (0.68-1.25) | | 6.0e-01 |
| | | Meta | 13266 (0.0025) | 59954 (0.0031) | 0.82 (0.63-1.07) | | 1.5e-01 |

Figure 3

B) High Eosinophil Asthma

| Gene | SNP | Group | NumCases (AAF) | NumCtrls (AAF) | OR (95% CI) | | P-value |
|------|-----|-------|----------------|----------------|-------------|---|---------|
| IL33 | rs1342326 | GSA | 1417 (0.18) | 20814 (0.16) | 1.12 (1.01-1.23) | | 3.2e-02 |
| | | OMNI | 3503 (0.18) | 37193 (0.16) | 1.12 (1.05-1.19) | | 6.5e-04 |
| | | Meta | 4920 (0.18) | 58007 (0.16) | 1.12 (1.06-1.18) | | 5.6e-05 |
| IL1RL1 | rs1420101 | GSA | 1416 (0.41) | 20815 (0.37) | 1.17 (1.08-1.27) | | 6.4e-05 |
| | | OMNI | 3497 (0.4) | 37207 (0.36) | 1.15 (1.1-1.21) | | 3.3e-08 |
| | | Meta | 4913 (0.4) | 58022 (0.37) | 1.16 (1.11-1.21) | | 9.6e-12 |
| IL33 | rs146597587 | xGEN | 1458 (0.0031) | 21150 (0.0033) | 0.89 (0.45-1.76) | | 7.4e-01 |
| | | VCRome | 3619 (0.0017) | 38804 (0.003) | 0.55 (0.31-0.99) | | 4.8e-02 |
| | | Meta | 5077 (0.0021) | 59954 (0.0031) | 0.68 (0.44-1.06) | | 8.6e-02 |

Figure 3 (cont.)

B) High Eosinophil COPD

B) High Eosinophil ACOS

C) Low Eosinophil ACOS

| Gene | SNP | Group | NumCases (AAF) | NumCtrls (AAF) | OR (95% CI) | P-value |
|---|---|---|---|---|---|---|
| IL33 | rs13342326 | GGA | 293 (0.18) | 20814 (0.16) | 1.12 (0.9-1.39) | 3.0e-01 |
| | | OMNI | 1022 (0.17) | 37193 (0.16) | 1.03 (0.91-1.16) | 6.2e-01 |
| | | Meta | 1315 (0.17) | 58007 (0.16) | 1.05 (0.95-1.17) | 3.4e-01 |
| IL1RL1 | rs1420101 | GGA | 293 (0.34) | 20815 (0.37) | 0.86 (0.74-1.05) | 1.7e-01 |
| | | OMNI | 1021 (0.35) | 37207 (0.36) | 0.97 (0.88-1.06) | 4.8e-01 |
| | | Meta | 1314 (0.35) | 58022 (0.37) | 0.95 (0.87-1.03) | 1.8e-01 |
| IL33 | rs148597587 | xGEN | 294 (0) | 21150 (0.0033) | 0 (0-1.64082072573848e+259) | 9.7e-01 |
| | | VCRome | 1060 (0.00047) | 38804 (0.003) | 1.57 (0.82-3) | 1.8e-01 |
| | | Meta | 1356 (0.00037) | 59954 (0.0031) | NA (0.82-3) | 2.2e-01 |

Figure 5 (cont.)

B) COPD

A

| | Asthma | COPD | ACOS | Controls |
|---|---|---|---|---|
| Number of Cases/Cases | 9293 | 7556 | 2336 | 38810 |
| Median Age Yrs (IQR) | 57.6 (43-69.1) | 70 (61-78.7) | 67.3 (57.9-76.625) | 60.7 (47-72) |
| Number of Females (%) | 6835 (0.74) | 3632 (0.48) | 1458 (0.62) | 22002 (0.58) |
| BMI kg/m2, (IQR) | 32.27 (27.12-38.2575) | 29.99 (25.62-35.18) | 31.92 (27.1-37.53) | 30.1 (26.055-35.24) |
| Height, in (IQR) | 65 (62.5-67.5) | 66 (63-69) | 65 (62-68) | 66 (63-69) |
| Current Smoker | 1583 (0.17) | 2171 (0.29) | 570 (0.24) | 5177 (0.13) |
| Former Smoker | 3655 (0.39) | 4541 (0.6) | 1308 (0.56) | 14201 (0.37) |
| Number with Eosinophil Counts | 8244 (0.89) | 6743 (0.89) | 2168 (0.93) | 30467 (0.79) |
| Median Eos Count (IQR) | 0.18 (0.115-0.26) | 0.19 (0.125-0.27) | 0.2 (0.13-0.28) | 0.15 (0.1-0.22) |

B

| | AERN | COPD | ACOS | Controls |
|---|---|---|---|---|
| Number of Cases/Cases | 3974 | 2227 | 657 | 21151 |
| Median Age Yrs (IQR) | 49.1 (34.2-62.3) | 64.8 (56.65-73.35) | 61.7 (52.8-71.6) | 53.5 (38.5-65.3) |
| Number of Females (%) | 2968 (0.75) | 1237 (0.56) | 449 (0.68) | 12886 (0.61) |
| BMI kg/m2, (IQR) | 31.07 (26.09-36.81) | 29.27 (25.2-34.8425) | 31.235 (26.57-37.14) | 29.3 (25.33-34.28) |
| Height, in (IQR) | 65 (63-67.99) | 66 (63-69) | 65 (62-68) | 66 (63-69) |
| Current Smoker | 843 (0.21) | 798 (0.36) | 211 (0.32) | 3658 (0.17) |
| Former Smoker | 1309 (0.33) | 1186 (0.53) | 325 (0.49) | 6619 (0.31) |
| Number with Eosinophil Counts | 3232 (0.81) | 1923 (0.86) | 599 (0.91) | 14571 (0.69) |
| Median Eos Count (IQR) | 0.18 (0.115-0.265) | 0.19 (0.12-0.27) | 0.2 (0.125-0.28) | 0.15 (0.1-0.22) |

| BMI | Asthma | COPD | AERD | Controls |
|---|---|---|---|---|
| Number of CasesCases | 8922 | 7322 | 2258 | 37244 |
| Median Age Yrs (IQR) | 57.8 (43.3-69.3) | 70.1 (61.1-78.9) | 67.45 (58.0-25-76.8) | 60.9 (47.2-72.2) |
| Number of Females (%) | 6552 (0.73) | 3903 (0.48) | 1406 (0.62) | 21677 (0.58) |
| BMI kg/m2, (IQR) | 32.285 (27.12-38.26) | 29.99 (25.62-625-35.15) | 31.93 (26.985-37.49) | 30.1 (26.07-35.22) |
| Height, in (IQR) | 65 (62.5-67.5) | 66 (63-69) | 65 (62-68) | 66 (63-69) |
| Current Smoker | 1516 (0.17) | 2393 (0.29) | 549 (0.24) | 4939 (0.13) |
| Former Smoker | 3522 (0.39) | 4412 (0.6) | 1269 (0.56) | 13658 (0.37) |
| Number with Eosinophil Counts | 7941 (0.89) | 6536 (0.89) | 2097 (0.93) | 29299 (0.79) |
| Median Eos Count (IQR) | 0.18 (0.115-0.26) | 0.19 (0.125-0.27) | 0.2 (0.13-0.28) | 0.15 (0.1-0.22) |

D

| CRS | Asthma | COPD | AERD | Controls |
|---|---|---|---|---|
| Number of CasesCases | 3912 | 2214 | 651 | 20816 |
| Median Age Yrs (IQR) | 49.6 (34.1-62.5) | 64.8 (56.7-73.4) | 61.7 (52.9-71.9) | 53.6 (38.6-65.4) |
| Number of Females (%) | 2915 (0.75) | 1218 (0.55) | 445 (0.68) | 12664 (0.61) |
| BMI kg/m2, (IQR) | 31.08 (26.14-36.8075) | 29.26 (25.18-34.84) | 31.17 (26.57-37.13) | 29.34 (25.36-34.28) |
| Height, in (IQR) | 65 (63-68) | 66 (63-69) | 65 (62.44-68) | 66 (63-69) |
| Current Smoker | 820 (0.21) | 782 (0.35) | 209 (0.32) | 3571 (0.17) |
| Former Smoker | 1291 (0.33) | 1190 (0.54) | 324 (0.5) | 6518 (0.31) |
| Number with Eosinophil Counts | 3184 (0.81) | 1918 (0.87) | 593 (0.91) | 14430 (0.69) |
| Median Eos Count (IQR) | 0.18 (0.115-0.265) | 0.19 (0.12-0.27) | 0.2 (0.125-0.28) | 0.15 (0.1-0.22) |

Figure 8 (cont.)

A) Allergic Rhinitis
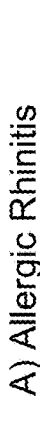
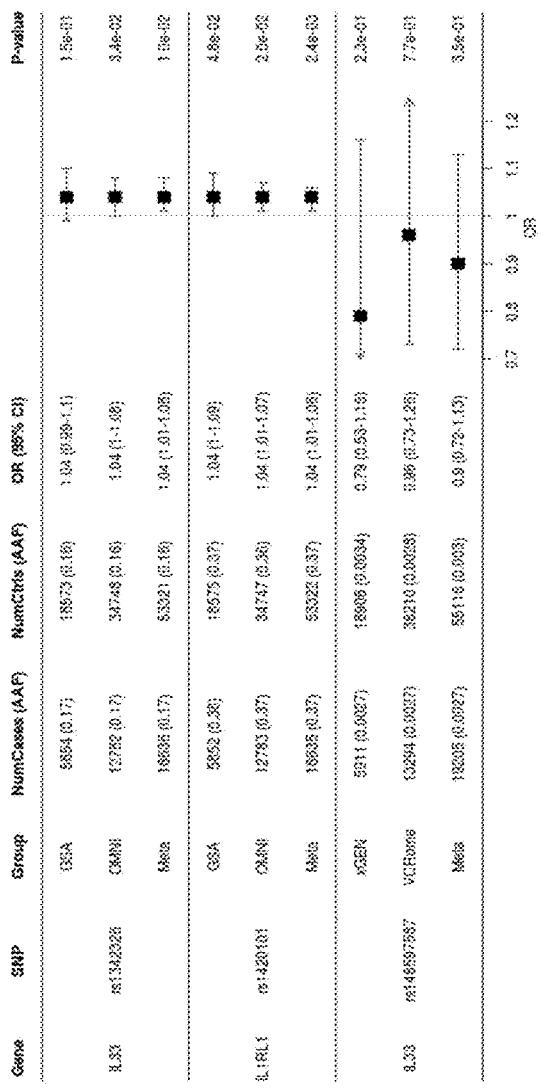
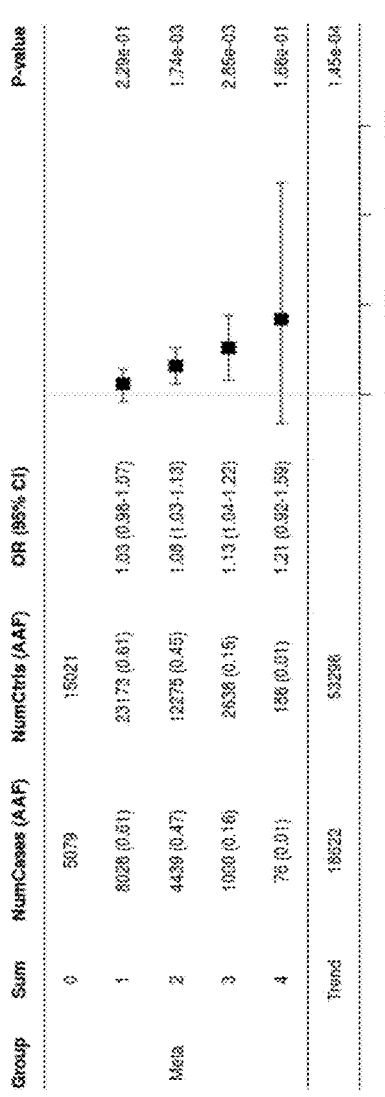
Figure 9

B) Nasal Polyps
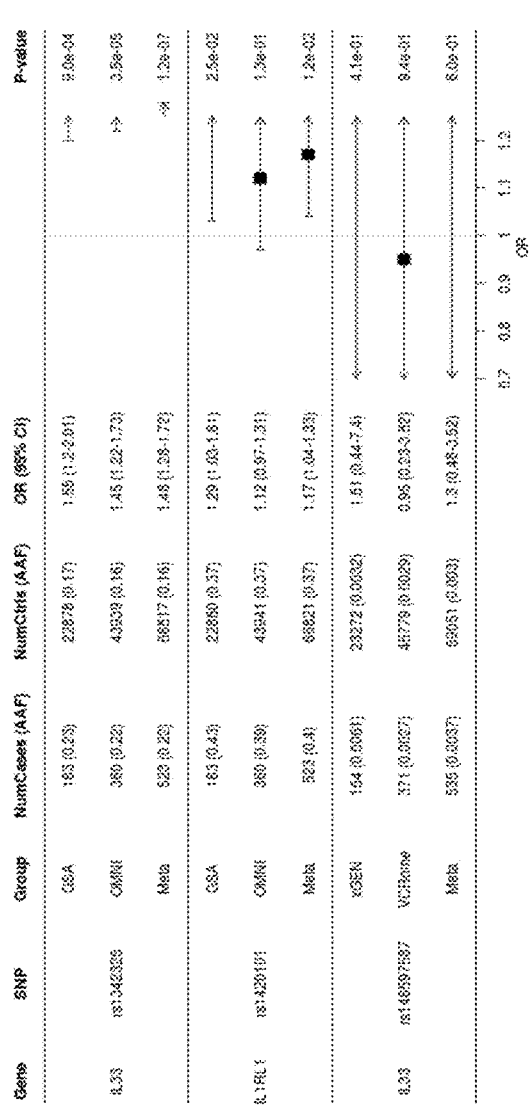
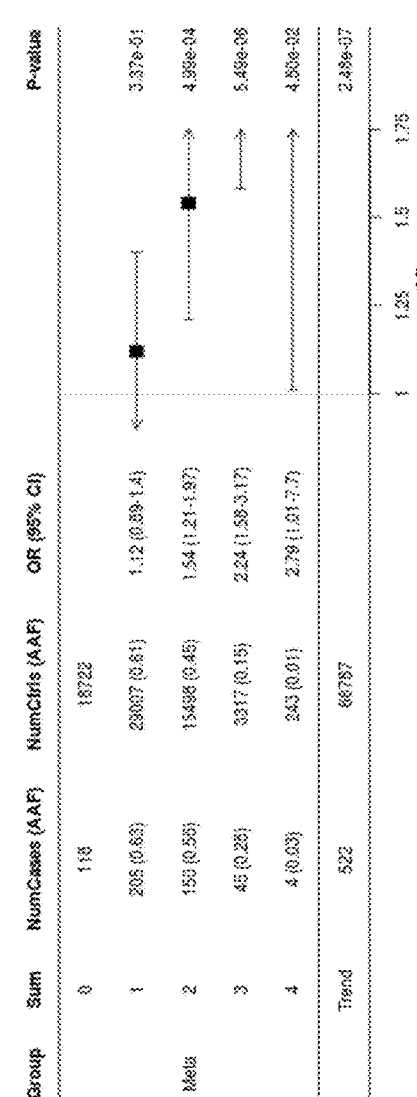
Figure 9 (cont.)

```
                          SEQUENCE LISTING

Sequence total quantity: 358
SEQ ID NO: 1              moltype = DNA  length = 366
FEATURE                   Location/Qualifiers
misc_feature              1..366
                          note = Synthetic
source                    1..366
                          mol_type = other DNA
                          organism = synthetic construct
SEQUENCE: 1
caggtgcagc tggtggagtc tggggggaggc gtggtccagc ctgggaggtc cctgagactc   60
tcctgtgcag cgtctggatt caccttcagt agttatggca tgcattgggt ccgccaggct  120
ccaggcaagg ggctggagtg ggtggcagtt atatggtatg atggaagaaa taaatactat  180
acagactccg tgaagggccg attcaccatc tccagagaca attccaagaa cacgctgtat  240
ctgcaaatgg acagcctgag agccgaggac acggctgtgt attactgtgc gagagagagg  300
tatatcagca gctattatgg ggggttcgac ccctgggggcc agggagccct ggtcaccgtc  360
tcctca                                                             366

SEQ ID NO: 2              moltype = AA  length = 122
FEATURE                   Location/Qualifiers
REGION                    1..122
                          note = Synthetic
source                    1..122
                          mol_type = protein
                          organism = synthetic construct
SEQUENCE: 2
QVQLVESGGG VVQPGRSLRL SCAASGFTFS SYGMHWVRQA PGKGLEWVAV IWYDGRNKYY   60
TDSVKGRFTI SRDNSKNTLY LQMDSLRAED TAVYYCARER YISSYYGGFD PWGQGALVTV  120
SS                                                                 122

SEQ ID NO: 3              moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 3
ggattcacct tcagtagtta tggc                                          24

SEQ ID NO: 4              moltype = AA  length = 8
FEATURE                   Location/Qualifiers
REGION                    1..8
                          note = Synthetic
source                    1..8
                          mol_type = protein
                          organism = synthetic construct
SEQUENCE: 4
GFTFSSYG                                                             8

SEQ ID NO: 5              moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 5
atatggtatg atggaagaaa taaa                                          24

SEQ ID NO: 6              moltype = AA  length = 8
FEATURE                   Location/Qualifiers
REGION                    1..8
                          note = Synthetic
source                    1..8
                          mol_type = protein
                          organism = synthetic construct
SEQUENCE: 6
IWYDGRNK                                                             8

SEQ ID NO: 7              moltype = DNA  length = 45
FEATURE                   Location/Qualifiers
misc_feature              1..45
                          note = Synthetic
```

```
source                1..45
                      mol_type = other DNA
                      organism = synthetic construct
SEQUENCE: 7
gcgagagaga ggtatatcag cagctattat gggggttcg accc                    45

SEQ ID NO: 8          moltype = AA   length = 15
FEATURE               Location/Qualifiers
REGION                1..15
                      note = Synthetic
source                1..15
                      mol_type = protein
                      organism = synthetic construct
SEQUENCE: 8
ARERYISSYY GGFDP                                                   15

SEQ ID NO: 9          moltype = DNA   length = 321
FEATURE               Location/Qualifiers
misc_feature          1..321
                      note = Synthetic
source                1..321
                      mol_type = other DNA
                      organism = synthetic construct
SEQUENCE: 9
gacatccaga tgacccagtc tccatcctcc gtgtctgcat ctgtaggaga cagagtcacc  60
atcacttgtc gggcgagtca gggtattagt agttggttag cctggtatca gcagaaacca  120
gggaaagccc ctaaggtcct gatctatgct gcatccagtt tgcaaagtgg ggtcccatca  180
aggttcagcg gcagtggatc tgggacagat ttcactctca ccatcagcag cctgcagcct  240
gaagattttg caacttacta ttgtcaacag gctaacagtt tcccattcac tttcggcccct  300
gggaccaaac tggatatcaa g                                            321

SEQ ID NO: 10         moltype = AA   length = 107
FEATURE               Location/Qualifiers
REGION                1..107
                      note = Synthetic
source                1..107
                      mol_type = protein
                      organism = synthetic construct
SEQUENCE: 10
DIQMTQSPSS VSASVGDRVT ITCRASQGIS SWLAWYQQKP GKAPKVLIYA ASSLQSGVPS  60
RFSGSGSGTD FTLTISSLQP EDFATYYCQQ ANSFPFTFGP GTKLDIK               107

SEQ ID NO: 11         moltype = DNA   length = 18
FEATURE               Location/Qualifiers
misc_feature          1..18
                      note = Synthetic
source                1..18
                      mol_type = other DNA
                      organism = synthetic construct
SEQUENCE: 11
cagggtatta gtagttgg                                                18

SEQ ID NO: 12         moltype = AA   length = 6
FEATURE               Location/Qualifiers
REGION                1..6
                      note = Synthetic
source                1..6
                      mol_type = protein
                      organism = synthetic construct
SEQUENCE: 12
QGISSW                                                             6

SEQ ID NO: 13         moltype =    length =
SEQUENCE: 13
000

SEQ ID NO: 14         moltype =    length =
SEQUENCE: 14
000

SEQ ID NO: 15         moltype = DNA   length = 27
FEATURE               Location/Qualifiers
misc_feature          1..27
                      note = Synthetic
source                1..27
                      mol_type = other DNA
                      organism = synthetic construct
SEQUENCE: 15
caacaggcta acagtttccc attcact                                      27
```

```
SEQ ID NO: 16          moltype = AA   length = 9
FEATURE                Location/Qualifiers
REGION                 1..9
                       note = Synthetic
source                 1..9
                       mol_type = protein
                       organism = synthetic construct
SEQUENCE: 16
QQANSFPFT                                                              9

SEQ ID NO: 17          moltype = DNA   length = 357
FEATURE                Location/Qualifiers
misc_feature           1..357
                       note = Synthetic
source                 1..357
                       mol_type = other DNA
                       organism = synthetic construct
SEQUENCE: 17
gaggtgcagc tgttggagtc tggggggac ttggtacagc ctggggggtc cctgagactc      60
tcctgtgcag cctctggatt caccttcagc agctatgcca tgagctgggt ccgccaggct     120
ccagggaagg ggctggagtg ggtctcagtt attagtggta gtggaagtag cacagactac     180
gcagactccg tgaagggccg gttcaccatt tccagagaca attccaggga cacgctgcat     240
ctgcaaatga acagcctgag agccgaggac acggccgtat attactgtgc gaaaacgttc     300
tactacttct acggtttgga cgtctggggc caagggacca cggtcaccgt ctcctca        357

SEQ ID NO: 18          moltype = AA   length = 119
FEATURE                Location/Qualifiers
REGION                 1..119
                       note = Synthetic
source                 1..119
                       mol_type = protein
                       organism = synthetic construct
SEQUENCE: 18
EVQLLESGGD LVQPGGSLRL SCAASGFTFS SYAMSWVRQA PGKGLEWVSV ISGSGSSTDY      60
ADSVKGRFTI SRDNSRDTLH LQMNSLRAED TAVYYCAKTF YYFYGLDVWG QGTTVTVSS      119

SEQ ID NO: 19          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 19
ggattcacct tcagcagcta tgcc                                            24

SEQ ID NO: 20          moltype = AA   length = 8
FEATURE                Location/Qualifiers
REGION                 1..8
                       note = Synthetic
source                 1..8
                       mol_type = protein
                       organism = synthetic construct
SEQUENCE: 20
GFTFSSYA                                                               8

SEQ ID NO: 21          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 21
attagtggta gtggaagtag caca                                            24

SEQ ID NO: 22          moltype = AA   length = 8
FEATURE                Location/Qualifiers
REGION                 1..8
                       note = Synthetic
source                 1..8
                       mol_type = protein
                       organism = synthetic construct
SEQUENCE: 22
ISGSGSST                                                               8

SEQ ID NO: 23          moltype = DNA   length = 36
FEATURE                Location/Qualifiers
```

-continued

```
misc_feature          1..36
                      note = Synthetic
source                1..36
                      mol_type = other DNA
                      organism = synthetic construct
SEQUENCE: 23
gcgaaaacgt tctactactt ctacggtttg gacgtc                             36

SEQ ID NO: 24         moltype = AA   length = 12
FEATURE               Location/Qualifiers
REGION                1..12
                      note = Synthetic
source                1..12
                      mol_type = protein
                      organism = synthetic construct
SEQUENCE: 24
AKTFYYFYGL DV                                                       12

SEQ ID NO: 25         moltype = DNA   length = 321
FEATURE               Location/Qualifiers
misc_feature          1..321
                      note = Synthetic
source                1..321
                      mol_type = other DNA
                      organism = synthetic construct
SEQUENCE: 25
gacatccaga tgacccagtc tccatcctcc ctgtctgcat ctttaagaga cagagtcacc    60
atcacttgcc gggcgagtca gggcattagc aattatttag cctggtatca gcagaaacca   120
gggaaagttc ctaaggtcct aatctatgct gcatccactt tgcaatcagg ggtcccatct   180
cggttcagtg gcagtggatc tgggacagtt ttcactctca ccatcagcag cctgcagact   240
gaagatgttg caacttatta ctgtcaaaag tatagcagtc ccccattcac tttcggccct   300
gggaccaaag tggatatcaa a                                             321

SEQ ID NO: 26         moltype = AA   length = 107
FEATURE               Location/Qualifiers
REGION                1..107
                      note = Synthetic
source                1..107
                      mol_type = protein
                      organism = synthetic construct
SEQUENCE: 26
DIQMTQSPSS LSASLRDRVT ITCRASQGIS NYLAWYQQKP GKVPKVLIYA ASTLQSGVPS    60
RFSGSGSGTV FTLTISSLQT EDVATYYCQK YSSAPFTFGP GTKVDIK                 107

SEQ ID NO: 27         moltype = DNA   length = 18
FEATURE               Location/Qualifiers
misc_feature          1..18
                      note = Synthetic
source                1..18
                      mol_type = other DNA
                      organism = synthetic construct
SEQUENCE: 27
cagggcatta gcaattat                                                 18

SEQ ID NO: 28         moltype = AA   length = 6
FEATURE               Location/Qualifiers
REGION                1..6
                      note = Synthetic
source                1..6
                      mol_type = protein
                      organism = synthetic construct
SEQUENCE: 28
QGISNY                                                               6

SEQ ID NO: 29         moltype =    length =
SEQUENCE: 29
000

SEQ ID NO: 30         moltype =    length =
SEQUENCE: 30
000

SEQ ID NO: 31         moltype = DNA   length = 27
FEATURE               Location/Qualifiers
misc_feature          1..27
                      note = Synthetic
source                1..27
                      mol_type = other DNA
                      organism = synthetic construct
```

```
SEQUENCE: 31
caaaagtata gcagtgcccc attcact                                             27

SEQ ID NO: 32           moltype = AA  length = 9
FEATURE                 Location/Qualifiers
REGION                  1..9
                        note = Synthetic
source                  1..9
                        mol_type = protein
                        organism = synthetic construct
SEQUENCE: 32
QKYSSAPFT                                                                 9

SEQ ID NO: 33           moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 33
caggtgcttc tggtacagtc tggggctgag gtgaagaagc ctggggccac agtgaaggtc   60
tcctgcaagg cttctggatc cactttcacc ggctactata tgcactgggt gcgacaggcc   120
cctggacaag ggcttgagtg gatgggatgg atcaacccta caatggtgg cacaaactat    180
gcacagaagt tcagggcag ggtcaccatg accagggaca cgtccatcag cacagcctac    240
atggaattga gcaggctgag atctgacgac acggccgtat attactgtgc gagagagttg   300
cggtataact ggaagtcctg gggccaggga accctggtca ccgtctcctc a             351

SEQ ID NO: 34           moltype = AA  length = 117
FEATURE                 Location/Qualifiers
REGION                  1..117
                        note = Synthetic
source                  1..117
                        mol_type = protein
                        organism = synthetic construct
SEQUENCE: 34
QVLLVQSGAE VKKPGATVKV SCKASGSTFT GYYMHWVRQA PGQGLEWMGW INPNNGGTNY   60
AQKFQGRVTM TRDTSISTAY MELSRLRSDD TAVYYCAREL RYNWKSWGQG TLVTVSS      117

SEQ ID NO: 35           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 35
ggatccactt tcaccggcta ctat                                                24

SEQ ID NO: 36           moltype = AA  length = 8
FEATURE                 Location/Qualifiers
REGION                  1..8
                        note = Synthetic
source                  1..8
                        mol_type = protein
                        organism = synthetic construct
SEQUENCE: 36
GSTFTGYY                                                                  8

SEQ ID NO: 37           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 37
atcaacccta acaatggtgg caca                                                24

SEQ ID NO: 38           moltype = AA  length = 8
FEATURE                 Location/Qualifiers
REGION                  1..8
                        note = Synthetic
source                  1..8
                        mol_type = protein
                        organism = synthetic construct
SEQUENCE: 38
INPNNGGT                                                                  8
```

-continued

```
SEQ ID NO: 39            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 39
gcgagagagt tgcggtataa ctggaagtcc                                   30

SEQ ID NO: 40            moltype = AA   length = 10
FEATURE                  Location/Qualifiers
REGION                   1..10
                         note = Synthetic
source                   1..10
                         mol_type = protein
                         organism = synthetic construct
SEQUENCE: 40
ARELRYNWKS                                                         10

SEQ ID NO: 41            moltype = DNA   length = 324
FEATURE                  Location/Qualifiers
misc_feature             1..324
                         note = Synthetic
source                   1..324
                         mol_type = other DNA
                         organism = synthetic construct
SEQUENCE: 41
gaaattgtgt tgacgcagtc tccaggcacc ctgtctttgt ctccagggga aagagtcacc   60
ctctcctgca gggccagtca gagtgttggc aggccctact tagcctggta ccaacagata  120
cctggccagg ctcccaggct cctcatctat ggtgcatcca gcagggccac tgacatccca  180
gacaggttca gtggcaatgg gtctgggaca gacttcactc tcaccatcag tagactggag  240
cctgaagatt ttgcagtgta ttactgtcag cagtatgata attcccctta cacttttggc  300
caggggacca ggctggagat caaa                                        324

SEQ ID NO: 42            moltype = AA   length = 108
FEATURE                  Location/Qualifiers
REGION                   1..108
                         note = Synthetic
source                   1..108
                         mol_type = protein
                         organism = synthetic construct
SEQUENCE: 42
EIVLTQSPGT LSLSPGERVT LSCRASQSVG RPYLAWYQQI PGQAPRLLIY GASSRATDIP   60
DRFSGNGSGT DFTLTISRLE PEDFAVYYCQ QYDNSPYTFG QGTRLEIK              108

SEQ ID NO: 43            moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 43
cagagtgttg gcaggcccta c                                            21

SEQ ID NO: 44            moltype = AA   length = 7
FEATURE                  Location/Qualifiers
REGION                   1..7
                         note = Synthetic
source                   1..7
                         mol_type = protein
                         organism = synthetic construct
SEQUENCE: 44
QSVGRPY                                                             7

SEQ ID NO: 45            moltype =    length =
SEQUENCE: 45
000

SEQ ID NO: 46            moltype =    length =
SEQUENCE: 46
000

SEQ ID NO: 47            moltype = DNA   length = 27
FEATURE                  Location/Qualifiers
misc_feature             1..27
                         note = Synthetic
source                   1..27
```

```
                      mol_type = other DNA
                      organism = synthetic construct
SEQUENCE: 47
cagcagtatg ataattcccc ttatact                                            27

SEQ ID NO: 48          moltype = AA  length = 9
FEATURE                Location/Qualifiers
REGION                 1..9
                       note = Synthetic
source                 1..9
                       mol_type = protein
                       organism = synthetic construct
SEQUENCE: 48
QQYDNSPYT                                                                9

SEQ ID NO: 49          moltype = DNA  length = 366
FEATURE                Location/Qualifiers
misc_feature           1..366
                       note = Synthetic
source                 1..366
                       mol_type = other DNA
                       organism = synthetic construct
SEQUENCE: 49
gaggtgcagc tggtggagtc tggggggaggc ttggtacaac ctggggggtc cctgagactc   60
tcctgtgcag cctctggatt cacctttaga agctttgcca tgagctgggt ccgccaggct  120
ccagggaagg ggctggaatt ggtctcagat ctcaggacta gtggtggtag tacatactac  180
gcagactccg tgaagggccg gctcaccatc tccagagaca attccaagaa cacgctgtat  240
ctgcaaatga acagcctgag agccgaggac acggccgtat attactgtgc gaaaagccac  300
tatagcacca gctggttcgg gggctttgac tactggggcc agggaaccct ggtcactgtc  360
tcctca                                                               366

SEQ ID NO: 50          moltype = AA  length = 122
FEATURE                Location/Qualifiers
REGION                 1..122
                       note = Synthetic
source                 1..122
                       mol_type = protein
                       organism = synthetic construct
SEQUENCE: 50
EVQLVESGGG LVQPGGSLRL SCAASGFTFR SFAMSWVRQA PGKGLELVSD LRTSGGSTYY   60
ADSVKGRLTI SRDNSKNTLY LQMNSLRAED TAVYYCAKSH YSTSWFGGFD YWGQGTLVTV  120
SS                                                                   122

SEQ ID NO: 51          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 51
ggattcacct ttagaagctt tgcc                                               24

SEQ ID NO: 52          moltype = AA  length = 8
FEATURE                Location/Qualifiers
REGION                 1..8
                       note = Synthetic
source                 1..8
                       mol_type = protein
                       organism = synthetic construct
SEQUENCE: 52
GFTFRSFA                                                                 8

SEQ ID NO: 53          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 53
ctcaggacta gtggtggtag taca                                               24

SEQ ID NO: 54          moltype = AA  length = 8
FEATURE                Location/Qualifiers
REGION                 1..8
                       note = Synthetic
source                 1..8
                       mol_type = protein
```

-continued

```
                               organism = synthetic construct
SEQUENCE: 54
LRTSGGST                                                                8

SEQ ID NO: 55              moltype = DNA  length = 45
FEATURE                    Location/Qualifiers
misc_feature               1..45
                           note = Synthetic
source                     1..45
                           mol_type = other DNA
                           organism = synthetic construct
SEQUENCE: 55
gcgaaaagcc actatagcac cagctggttc gggggctttg actac                       45

SEQ ID NO: 56              moltype = AA  length = 15
FEATURE                    Location/Qualifiers
REGION                     1..15
                           note = Synthetic
source                     1..15
                           mol_type = protein
                           organism = synthetic construct
SEQUENCE: 56
AKSHYSTSWF GGFDY                                                         15

SEQ ID NO: 57              moltype = DNA  length = 321
FEATURE                    Location/Qualifiers
misc_feature               1..321
                           note = Synthetic
source                     1..321
                           mol_type = other DNA
                           organism = synthetic construct
SEQUENCE: 57
gacatccaga tgacccagtc tccatcttcc gtgtctgctt ctgtaggaga cagagtcacc  60
atcacttgtc gggcgagtca gggtttttagc agctggttag cctggtatca gcagaaacca  120
gggaaagccc ctaagctcct gatctatgct gcatccagtt tgcaaagtgg ggtcccatca  180
aggttcagcg gcagtggatc tgggacagat ttcactctca ccatcaccaa cctgcagcct  240
gaagattttg caacttacta ttgtcaacag gctaacagtt tccctctcac tttcggcgga  300
gggaccaagg tggagatcaa a                                            321

SEQ ID NO: 58              moltype = AA  length = 107
FEATURE                    Location/Qualifiers
REGION                     1..107
                           note = Synthetic
source                     1..107
                           mol_type = protein
                           organism = synthetic construct
SEQUENCE: 58
DIQMTQSPSS VSASVGDRVT ITCRASQGFS SWLAWYQQKP GKAPKLLIYA ASSLQSGVPS  60
RFSGSGSGTD FTLTITNLQP EDFATYYCQQ ANSFPLTFGG GTKVEIK               107

SEQ ID NO: 59              moltype = DNA  length = 18
FEATURE                    Location/Qualifiers
misc_feature               1..18
                           note = Synthetic
source                     1..18
                           mol_type = other DNA
                           organism = synthetic construct
SEQUENCE: 59
cagggtttta gcagctgg                                                     18

SEQ ID NO: 60              moltype = AA  length = 6
FEATURE                    Location/Qualifiers
REGION                     1..6
                           note = Synthetic
source                     1..6
                           mol_type = protein
                           organism = synthetic construct
SEQUENCE: 60
QGFSSW                                                                  6

SEQ ID NO: 61              moltype =    length =
SEQUENCE: 61
000

SEQ ID NO: 62              moltype =    length =
SEQUENCE: 62
000

SEQ ID NO: 63              moltype = DNA  length = 27
```

-continued

```
FEATURE                Location/Qualifiers
misc_feature           1..27
                       note = Synthetic
source                 1..27
                       mol_type = other DNA
                       organism = synthetic construct
SEQUENCE: 63
caacaggcta acagtttccc tctcact                                          27

SEQ ID NO: 64          moltype = AA  length = 9
FEATURE                Location/Qualifiers
REGION                 1..9
                       note = Synthetic
source                 1..9
                       mol_type = protein
                       organism = synthetic construct
SEQUENCE: 64
QQANSFPLT                                                              9

SEQ ID NO: 65          moltype = DNA  length = 366
FEATURE                Location/Qualifiers
misc_feature           1..366
                       note = Synthetic
source                 1..366
                       mol_type = other DNA
                       organism = synthetic construct
SEQUENCE: 65
gaggtgcagc tggtggagtc tggggggaggc ttggtacagc ctggggggtc cctgagactc    60
tcctgtgcag cctctggatt cacgtttagc agctatgtca tgagctgggt ccgccaggct    120
ccagggaagg ggctggagtg ggtctcaagt attagtggta atggtggtag cacaaactac    180
gcagactccg tgaagggccg gttcaccatc tccagagaca attccaagaa cacgctgttt    240
ctggaaatga acagcctgag agccgaggac acggccgtat attactgtgc gaaatcactg    300
ggaactacca cgacttttttt ggggtttgac tattggggcc agggaaccct ggtcaccgtc    360
tcctca                                                                366

SEQ ID NO: 66          moltype = AA  length = 122
FEATURE                Location/Qualifiers
REGION                 1..122
                       note = Synthetic
source                 1..122
                       mol_type = protein
                       organism = synthetic construct
SEQUENCE: 66
EVQLVESGGG LVQPGGSLRL SCAASGFTFS SYVMSWVRQA PGKGLEWVSS ISGNGGSTNY     60
ADSVKGRFTI SRDNSKNTLF LEMNSLRAED TAVYYCAKSL GTTTTFLGFD YWGQGTLVTV     120
SS                                                                    122

SEQ ID NO: 67          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 67
ggattcacgt ttagcagcta tgtc                                            24

SEQ ID NO: 68          moltype = AA  length = 8
FEATURE                Location/Qualifiers
REGION                 1..8
                       note = Synthetic
source                 1..8
                       mol_type = protein
                       organism = synthetic construct
SEQUENCE: 68
GFTFSSYV                                                               8

SEQ ID NO: 69          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 69
attagtggta atggtggtag caca                                            24

SEQ ID NO: 70          moltype = AA  length = 8
FEATURE                Location/Qualifiers
```

-continued

```
REGION                  1..8
                        note = Synthetic
source                  1..8
                        mol_type = protein
                        organism = synthetic construct
SEQUENCE: 70
ISGNGGST                                                                         8

SEQ ID NO: 71           moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 71
gcgaaatcac tgggaactac cacgactttt ttggggtttg actat           45

SEQ ID NO: 72           moltype = AA  length = 15
FEATURE                 Location/Qualifiers
REGION                  1..15
                        note = Synthetic
source                  1..15
                        mol_type = protein
                        organism = synthetic construct
SEQUENCE: 72
AKSLGTTTTF LGFDY                                                                 15

SEQ ID NO: 73           moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 73
gacatccaga tgacccagtc tccatcttcc gtgtctgcat ctgtaggaga cagagtcacc   60
atcacttgtc gggcgagtca gggtattagc agctggttag cctggtatca gcagaaacca  120
gggaaagccc ctaaactcct gatctatgct gcatccagtt tgcaaagtgg ggtcccatca  180
aggttcagcg gcagtggatc tgggacatat ttcactctca ccatcagcag cctgcagcct  240
gaagattttg caacttacta ttgtcaacag gctaacagtt ccctctcac tttcggcgga  300
gggaccaagg tggagatcaa a                                            321

SEQ ID NO: 74           moltype = AA  length = 107
FEATURE                 Location/Qualifiers
REGION                  1..107
                        note = Synthetic
source                  1..107
                        mol_type = protein
                        organism = synthetic construct
SEQUENCE: 74
DIQMTQSPSS VSASVGDRVT ITCRASQGIS SWLAWYQQKP GKAPKLLIYA ASSLQSGVPS   60
RFSGSGSGTY FTLTISSLQP EDFATYYCQQ ANSFPLTFGG GTKVEIK               107

SEQ ID NO: 75           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 75
cagggtatta gcagctgg                                                 18

SEQ ID NO: 76           moltype = AA  length = 6
FEATURE                 Location/Qualifiers
REGION                  1..6
                        note = Synthetic
source                  1..6
                        mol_type = protein
                        organism = synthetic construct
SEQUENCE: 76
QGISSW                                                                            6

SEQ ID NO: 77           moltype =    length =
SEQUENCE: 77
000

SEQ ID NO: 78           moltype =    length =
```

```
SEQUENCE: 78
000

SEQ ID NO: 79            moltype = DNA   length = 27
FEATURE                  Location/Qualifiers
misc_feature             1..27
                         note = Synthetic
source                   1..27
                         mol_type = other DNA
                         organism = synthetic construct
SEQUENCE: 79
caacaggcta acagtttccc tctcact                                      27

SEQ ID NO: 80            moltype = AA   length = 9
FEATURE                  Location/Qualifiers
REGION                   1..9
                         note = Synthetic
source                   1..9
                         mol_type = protein
                         organism = synthetic construct
SEQUENCE: 80
QQANSFPLT                                                          9

SEQ ID NO: 81            moltype = DNA   length = 363
FEATURE                  Location/Qualifiers
misc_feature             1..363
                         note = Synthetic
source                   1..363
                         mol_type = other DNA
                         organism = synthetic construct
SEQUENCE: 81
caggtgcagc tgcaggagtc gggcccagga ctggtgaagc cttcggagac cctgtccctc   60
acctgcactg tctctggtgg ctccatcagt agttattact ggagctggat ccggcagccc  120
ccagggaagg gactggagtt gattgggtat atttattaca gtgggagcac caattataac  180
ccctccctca agagtcgagt caccatatct gtagacacgt ccaagaacca cttctccctg  240
aagctgagct ctgtgaccgc tgcggacacg gccgtatatt actgtgcgag atcccagtat  300
accagtagtt ggtacggttc ttttgatatc tggggccaag ggacaatggt caccgtctct  360
tca                                                               363

SEQ ID NO: 82            moltype = AA   length = 121
FEATURE                  Location/Qualifiers
REGION                   1..121
                         note = Synthetic
source                   1..121
                         mol_type = protein
                         organism = synthetic construct
SEQUENCE: 82
QVQLQESGPG LVKPSETLSL TCTVSGGSIS SYYWSWIRQP PGKGLELIGY IYYSGSTNYN   60
PSLKSRVTIS VDTSKNHFSL KLSSVTAADT AVYYCARSQY TSSWYGSFDI WGQGTMVTVS  120
S                                                                 121

SEQ ID NO: 83            moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 83
ggtggctcca tcagtagtta ttac                                         24

SEQ ID NO: 84            moltype = AA   length = 8
FEATURE                  Location/Qualifiers
REGION                   1..8
                         note = Synthetic
source                   1..8
                         mol_type = protein
                         organism = synthetic construct
SEQUENCE: 84
GGSISSYY                                                           8

SEQ ID NO: 85            moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 85
```

```
atttattaca gtgggagcac c                                              21

SEQ ID NO: 86          moltype = AA  length = 7
FEATURE                Location/Qualifiers
REGION                 1..7
                       note = Synthetic
source                 1..7
                       mol_type = protein
                       organism = synthetic construct
SEQUENCE: 86
IYYSGST                                                              7

SEQ ID NO: 87          moltype = DNA  length = 45
FEATURE                Location/Qualifiers
misc_feature           1..45
                       note = Synthetic
source                 1..45
                       mol_type = other DNA
                       organism = synthetic construct
SEQUENCE: 87
gcgagatccc agtataccag tagttggtac ggttcttttg atatc                    45

SEQ ID NO: 88          moltype = AA  length = 15
FEATURE                Location/Qualifiers
REGION                 1..15
                       note = Synthetic
source                 1..15
                       mol_type = protein
                       organism = synthetic construct
SEQUENCE: 88
ARSQYTSSWY GSFDI                                                     15

SEQ ID NO: 89          moltype = DNA  length = 321
FEATURE                Location/Qualifiers
misc_feature           1..321
                       note = Synthetic
source                 1..321
                       mol_type = other DNA
                       organism = synthetic construct
SEQUENCE: 89
gacatccaga tgacccagtc tccatcttcc gtgtctgcat ctgtaggaga cagagtcacc    60
atcacttgtc gggcgagtca gggtattagc acctggttag cctggtttca gcagaaacca   120
gggaaagccc ctaagctcct gatctatgct gcatccactt tacaaggtgg ggtcccatca   180
aggttcagcg gcagtggatc tgggccagaa ttcactctca ccatcagcag cctgcagcct   240
gaagattttg caacttacta ttgtcaacag gctaacagtt tcccgtggac gttcggccaa   300
gggaccaagg tggaaatcaa a                                             321

SEQ ID NO: 90          moltype = AA  length = 107
FEATURE                Location/Qualifiers
REGION                 1..107
                       note = Synthetic
source                 1..107
                       mol_type = protein
                       organism = synthetic construct
SEQUENCE: 90
DIQMTQSPSS VSASVGDRVT ITCRASQGIS TWLAWFQQKP GKAPKLLIYA ASTLQGGVPS    60
RFSGSGSGPE FTLTISSLQP EDFATYYCQQ ANSFPWTFGQ GTKVEIK                 107

SEQ ID NO: 91          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 91
cagggtatta gcacctgg                                                  18

SEQ ID NO: 92          moltype = AA  length = 6
FEATURE                Location/Qualifiers
REGION                 1..6
                       note = Synthetic
source                 1..6
                       mol_type = protein
                       organism = synthetic construct
SEQUENCE: 92
QGISTW                                                               6

SEQ ID NO: 93          moltype =    length =
```

-continued

```
SEQUENCE: 93
000

SEQ ID NO: 94              moltype =    length =
SEQUENCE: 94
000

SEQ ID NO: 95              moltype = DNA   length = 27
FEATURE                    Location/Qualifiers
misc_feature               1..27
                           note = Synthetic
source                     1..27
                           mol_type = other DNA
                           organism = synthetic construct
SEQUENCE: 95
caacaggcta acagtttccc gtggacg                                   27

SEQ ID NO: 96              moltype = AA   length = 9
FEATURE                    Location/Qualifiers
REGION                     1..9
                           note = Synthetic
source                     1..9
                           mol_type = protein
                           organism = synthetic construct
SEQUENCE: 96
QQANSFPWT                                                        9

SEQ ID NO: 97              moltype = DNA   length = 366
FEATURE                    Location/Qualifiers
misc_feature               1..366
                           note = Synthetic
source                     1..366
                           mol_type = other DNA
                           organism = synthetic construct
SEQUENCE: 97
caggttcagc tggtgcagtc tggagctgag gtgaagaagc ctgggggcctc agtgaaggtc   60
tcctgcaagg cctctggtta caccttaac agctatggta tcagctgggt gcgacaggcc  120
cctggacaag ggcttgagtg gatgggatgg atcagctccc acaatggtaa cagtcactat  180
gtacagaagt tccagggcag agtctccatg accacagaca catccacgag tacagcctac  240
atggaactga ggagccttag atctgacgac acggccgtgt attactgtgc gagacactcg  300
tataccacca gctggtacgg gggtttttgac tattggggcc agggaaccct ggtcaccgtc  360
tcctca                                                         366

SEQ ID NO: 98              moltype = AA   length = 122
FEATURE                    Location/Qualifiers
REGION                     1..122
                           note = Synthetic
source                     1..122
                           mol_type = protein
                           organism = synthetic construct
SEQUENCE: 98
QVQLVQSGAE VKKPGASVKV SCKASGYTFN SYGISWVRQA PGQGLEWMGW ISSHNGNSHY   60
VQKFQGRVSM TTDTSTSTAY MELRSLRSDD TAVYYCARHS YTTSWYGGFD YWGQGTLVTV  120
SS                                                             122

SEQ ID NO: 99              moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 99
ggttacacct ttaacagcta tggt                                      24

SEQ ID NO: 100             moltype = AA   length = 8
FEATURE                    Location/Qualifiers
REGION                     1..8
                           note = Synthetic
source                     1..8
                           mol_type = protein
                           organism = synthetic construct
SEQUENCE: 100
GYTFNSYG                                                         8

SEQ ID NO: 101             moltype = DNA   length = 24
FEATURE                    Location/Qualifiers
misc_feature               1..24
                           note = Synthetic
```

```
source                  1..24
                        mol_type = other DNA
                        organism = synthetic construct
SEQUENCE: 101
atcagctccc acaatggtaa cagt                                          24

SEQ ID NO: 102          moltype = AA  length = 8
FEATURE                 Location/Qualifiers
REGION                  1..8
                        note = Synthetic
source                  1..8
                        mol_type = protein
                        organism = synthetic construct
SEQUENCE: 102
ISSHNGNS                                                            8

SEQ ID NO: 103          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 103
gcgagacact cgtataccac cagctggtac gggggttttg actat                   45

SEQ ID NO: 104          moltype = AA  length = 15
FEATURE                 Location/Qualifiers
REGION                  1..15
                        note = Synthetic
source                  1..15
                        mol_type = protein
                        organism = synthetic construct
SEQUENCE: 104
ARHSYTTSWY GGFDY                                                    15

SEQ ID NO: 105          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 105
gacatccaga tgacccagtc tccatcttcc gtgtctgcat ctgtaggaga cagagtcacc   60
atcacttgtc gggcgagtca gggttttagc agctggttag cctggtatca gcagaaacca  120
gggaaagccc ctcagctcct gatctatgct gcatccagtt tgcaaagtgg ggtcccatca  180
aggttcagcg gcagtggatc tgggtcagat ttcactctca ccatcagcag cctgcagcct  240
gaagattttg caacttacta ttgtcaacag gctaacagtt ccctctcac tttcggcgga   300
gggaccaagg tggagatcaa a                                            321

SEQ ID NO: 106          moltype = AA  length = 107
FEATURE                 Location/Qualifiers
REGION                  1..107
                        note = Synthetic
source                  1..107
                        mol_type = protein
                        organism = synthetic construct
SEQUENCE: 106
DIQMTQSPSS VSASVGDRVT ITCRASQGFS SWLAWYQQKP GKAPQLLIYA ASSLQSGVPS   60
RFSGSGSGSD FTLTISSLQP EDFATYYCQQ ANSFPLTFGG GTKVEIK                107

SEQ ID NO: 107          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 107
cagggtttta gcagctgg                                                18

SEQ ID NO: 108          moltype = AA  length = 6
FEATURE                 Location/Qualifiers
REGION                  1..6
                        note = Synthetic
source                  1..6
                        mol_type = protein
                        organism = synthetic construct
```

-continued

```
SEQUENCE: 108
QGFSSW                                                                     6

SEQ ID NO: 109         moltype =    length =
SEQUENCE: 109
000

SEQ ID NO: 110         moltype =    length =
SEQUENCE: 110
000

SEQ ID NO: 111         moltype = DNA   length = 27
FEATURE                Location/Qualifiers
misc_feature           1..27
                       note = Synthetic
source                 1..27
                       mol_type = other DNA
                       organism = synthetic construct
SEQUENCE: 111
caacaggcta acagtttccc tctcact                                             27

SEQ ID NO: 112         moltype = AA   length = 9
FEATURE                Location/Qualifiers
REGION                 1..9
                       note = Synthetic
source                 1..9
                       mol_type = protein
                       organism = synthetic construct
SEQUENCE: 112
QQANSFPLT                                                                  9

SEQ ID NO: 113         moltype = DNA   length = 366
FEATURE                Location/Qualifiers
misc_feature           1..366
                       note = Synthetic
source                 1..366
                       mol_type = other DNA
                       organism = synthetic construct
SEQUENCE: 113
gaggtgcagc tggtggagtc cggggggaggc ttggttcagc cggggggggtc cctgagactc        60
tcctgtgcag cctctggaat caccttgagc agctatggca tgagctgggt ccgccaggct         120
ccagggaagg gactggagtg ggtcgcatcc atttttggta gtggtggtgg cccatactac         180
gcagactccg tgaagggccg gttcaccatg tccagagaca attccaagaa cacgctgtat         240
ttgcaaatga acagcctgag agccgaggac acggccgtat attattgtgc gaaagatcga         300
tacagtggga gctactacgg aggttttgac tactgggcc ggggaaccct ggtcaccgtc          360
tcctca                                                                    366

SEQ ID NO: 114         moltype = AA   length = 122
FEATURE                Location/Qualifiers
REGION                 1..122
                       note = Synthetic
source                 1..122
                       mol_type = protein
                       organism = synthetic construct
SEQUENCE: 114
EVQLVESGGG LVQPGGSLRL SCAASGITLS SYGMSWVRQA PGKGLEWVAS IFGSGGGPYY          60
ADSVKGRFTM SRDNSKNTLY LQMNSLRAED TAVYYCAKDR YSGSYYGGFD YWGRGTLVTV         120
SS                                                                        122

SEQ ID NO: 115         moltype = DNA   length = 24
FEATURE                Location/Qualifiers
misc_feature           1..24
                       note = Synthetic
source                 1..24
                       mol_type = other DNA
                       organism = synthetic construct
SEQUENCE: 115
ggaatcacct tgagcagcta tggc                                                24

SEQ ID NO: 116         moltype = AA   length = 8
FEATURE                Location/Qualifiers
REGION                 1..8
                       note = Synthetic
source                 1..8
                       mol_type = protein
                       organism = synthetic construct
SEQUENCE: 116
GITLSSYG                                                                   8
```

-continued

```
SEQ ID NO: 117            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 117
atttttggta gtggtggtgg ccca                                     24

SEQ ID NO: 118            moltype = AA   length = 8
FEATURE                   Location/Qualifiers
REGION                    1..8
                          note = Synthetic
source                    1..8
                          mol_type = protein
                          organism = synthetic construct
SEQUENCE: 118
IFGSGGGP                                                        8

SEQ ID NO: 119            moltype = DNA   length = 45
FEATURE                   Location/Qualifiers
misc_feature              1..45
                          note = Synthetic
source                    1..45
                          mol_type = other DNA
                          organism = synthetic construct
SEQUENCE: 119
gcgaaagatc gatacagtgg gagctactac ggaggttttg actac             45

SEQ ID NO: 120            moltype = AA   length = 15
FEATURE                   Location/Qualifiers
REGION                    1..15
                          note = Synthetic
source                    1..15
                          mol_type = protein
                          organism = synthetic construct
SEQUENCE: 120
AKDRYSGSYY GGFDY                                                15

SEQ ID NO: 121            moltype = DNA   length = 321
FEATURE                   Location/Qualifiers
misc_feature              1..321
                          note = Synthetic
source                    1..321
                          mol_type = other DNA
                          organism = synthetic construct
SEQUENCE: 121
gacatccaga tgacccagtc tccatcttcc gtgtctgcat ctgtaggaga cagagtcacc  60
atcacttgtc gggcgagtca gggtattacc agctggttag cctggtatca gcagaaacca 120
gggaaagccc ctacactcct gatctatgct gcatccagtt tgcaaactgg ggtcccatca 180
aggttcagcg gcagtggatc tgggacagat ttcactctca ccatcagcag cctgcagcct 240
gaacattttg caacttacta ttgtcaacag gctaacagtt tccctcctac tttcggcgga 300
gggaccaagg tggagatcaa a                                          321

SEQ ID NO: 122            moltype = AA   length = 107
FEATURE                   Location/Qualifiers
REGION                    1..107
                          note = Synthetic
source                    1..107
                          mol_type = protein
                          organism = synthetic construct
SEQUENCE: 122
DIQMTQSPSS VSASVGDRVT ITCRASQGIT SWLAWYQQKP GKAPTLLIYA ASSLQTGVPS  60
RFSGSGSGTD FTLTISSLQP EHFATYYCQQ ANSFPPTFGG GTKVEIK              107

SEQ ID NO: 123            moltype = DNA   length = 18
FEATURE                   Location/Qualifiers
misc_feature              1..18
                          note = Synthetic
source                    1..18
                          mol_type = other DNA
                          organism = synthetic construct
SEQUENCE: 123
cagggtatta ccagctgg                                             18

SEQ ID NO: 124            moltype = AA   length = 6
FEATURE                   Location/Qualifiers
REGION                    1..6
```

```
                          note = Synthetic
source                    1..6
                          mol_type = protein
                          organism = synthetic construct
SEQUENCE: 124
QGITSW                                                             6

SEQ ID NO: 125            moltype =    length =
SEQUENCE: 125
000

SEQ ID NO: 126            moltype =    length =
SEQUENCE: 126
000

SEQ ID NO: 127            moltype = DNA   length = 27
FEATURE                   Location/Qualifiers
misc_feature              1..27
                          note = Synthetic
source                    1..27
                          mol_type = other DNA
                          organism = synthetic construct
SEQUENCE: 127
caacaggcta acagtttccc tcctact                                      27

SEQ ID NO: 128            moltype = AA   length = 9
FEATURE                   Location/Qualifiers
REGION                    1..9
                          note = Synthetic
source                    1..9
                          mol_type = protein
                          organism = synthetic construct SEQUENCE: 128
QQANSFPPT                                                          9

SEQ ID NO: 129            moltype = DNA   length = 366
FEATURE                   Location/Qualifiers
misc_feature              1..366
                          note = Synthetic
source                    1..366
                          mol_type = other DNA
                          organism = synthetic construct
SEQUENCE: 129
gaggtgcagc tggtggagtc tggggggaggc ttggtacagc ctggggggtc cctaagactc  60
tcctgtgcag cctctggatt caccttttagc agttatgcct tgacctgggt ccgccaggct  120
ccagggaagg ggctggagtg ggtctctttt attagtggta gtggtggtag gccattctac  180
gcagactccg tgaagggccg gttcaccatc tccagagaca attccaagaa catgctgtat  240
ctgcaaatga acagcctgag agccgaggac acggccatat attactgtgc gaagtccctg  300
tataccacca gctggtacgg ggggttcgac tcctggggcc agggaaccct ggtcaccgtc  360
tcctca                                                             366

SEQ ID NO: 130            moltype = AA   length = 122
FEATURE                   Location/Qualifiers
REGION                    1..122
                          note = Synthetic
source                    1..122
                          mol_type = protein
                          organism = synthetic construct
SEQUENCE: 130
EVQLVESGGG LVQPGGSLRL SCAASGFTFS SYALTWVRQA PGKGLEWVSF ISGSGGRPFY  60
ADSVKGRFTI SRDNSKNMLY LQMNSLRAED TAIYYCAKSL YTTSWYGGFD SWGQGTLVTV  120
SS                                                                 122

SEQ ID NO: 131            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 131
ggattcacct ttagcagtta tgcc                                         24

SEQ ID NO: 132            moltype = AA   length = 8
FEATURE                   Location/Qualifiers
REGION                    1..8
                          note = Synthetic
source                    1..8
                          mol_type = protein
```

-continued

```
                           organism = synthetic construct
SEQUENCE: 132
GFTFSSYA                                                          8

SEQ ID NO: 133            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 133
attagtggta gtggtggtag gcca                                       24

SEQ ID NO: 134            moltype = AA   length = 8
FEATURE                   Location/Qualifiers
REGION                    1..8
                          note = Synthetic
source                    1..8
                          mol_type = protein
                          organism = synthetic construct
SEQUENCE: 134
ISGSGGRP                                                          8

SEQ ID NO: 135            moltype = DNA   length = 45
FEATURE                   Location/Qualifiers
misc_feature              1..45
                          note = Synthetic
source                    1..45
                          mol_type = other DNA
                          organism = synthetic construct
SEQUENCE: 135
gcgaagtccc tgtataccac cagctggtac gggggggttcg actcc              45

SEQ ID NO: 136            moltype = AA   length = 15
FEATURE                   Location/Qualifiers
REGION                    1..15
                          note = Synthetic
source                    1..15
                          mol_type = protein
                          organism = synthetic construct
SEQUENCE: 136
AKSLYTTSWY GGFDS                                                 15

SEQ ID NO: 137            moltype = DNA   length = 321
FEATURE                   Location/Qualifiers
misc_feature              1..321
                          note = Synthetic
source                    1..321
                          mol_type = other DNA
                          organism = synthetic construct
SEQUENCE: 137
gacatccaga tgacccagtc tccatcttcc gtgtctgcat ctgtaggaga cagagtcacc  60
atcacttgtc gggcgagtca gggtgtcgtc agctggttag cctggtatca gcagaaacca  120
gggaaagccc ctaagctcct gatctatgct gcatccagtt tgcaaagtgg ggtcccatca  180
aggttcagcg gcagtggatc tgggacagat ttcactctca ccatcagcag cctgcagcct  240
gaagattttg caacttatta ttgtcaacag tctaacagtt ttcctttcac tctcggccct  300
gggaccaaag tggatatcaa a                                            321

SEQ ID NO: 138            moltype = AA   length = 107
FEATURE                   Location/Qualifiers
REGION                    1..107
                          note = Synthetic
source                    1..107
                          mol_type = protein
                          organism = synthetic construct
SEQUENCE: 138
DIQMTQSPSS VSASVGDRVT ITCRASQGVV SWLAWYQQKP GKAPKLLIYA ASSLQSGVPS  60
RFSGSGSGTD FTLTISSLQP EDFATYYCQQ SNSFPFTLGP GTKVDIK               107

SEQ ID NO: 139            moltype = DNA   length = 18
FEATURE                   Location/Qualifiers
misc_feature              1..18
                          note = Synthetic
source                    1..18
                          mol_type = other DNA
                          organism = synthetic construct
SEQUENCE: 139
cagggtgtcg tcagctgg                                              18
```

-continued

```
SEQ ID NO: 140          moltype = AA   length = 6
FEATURE                 Location/Qualifiers
REGION                  1..6
                        note = Synthetic
source                  1..6
                        mol_type = protein
                        organism = synthetic construct
SEQUENCE: 140
QGVVSW                                                              6

SEQ ID NO: 141          moltype =    length =
SEQUENCE: 141
000

SEQ ID NO: 142          moltype =    length =
SEQUENCE: 142
000

SEQ ID NO: 143          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 143
caacagtcta acagtttccc tttc                                         24

SEQ ID NO: 144          moltype = AA   length = 8
FEATURE                 Location/Qualifiers
REGION                  1..8
                        note = Synthetic
source                  1..8
                        mol_type = protein
                        organism = synthetic construct
SEQUENCE: 144
QQSNSFPF                                                            8

SEQ ID NO: 145          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 145
caggtgcagc tggtgcagtc tgggggctgaa gtgaagaagc ctggggcctc agtgaaggtc  60
tcctgcaagg cttctggata caccttcacc ggccactata tgtactggat gcgacaggcc  120
cctgacaag ggcttgagtg gatgggatgg atcaacccta cagtggtgg cacaaactat  180
gcacagaagt ttcaggacag ggtcaccatg accagggaca cgtccatcag cacagcctac  240
atggagctga gcaggctgag atctgacgac acggccgtgt attactgtgc gagagggaga  300
tatggcagta gctggtacgg ggggtttgag tactgggggc agggaaccct ggtcaccgtc  360
tcctca                                                             366

SEQ ID NO: 146          moltype = AA   length = 122
FEATURE                 Location/Qualifiers
REGION                  1..122
                        note = Synthetic
source                  1..122
                        mol_type = protein
                        organism = synthetic construct
SEQUENCE: 146
QVQLVQSGAE VKKPGASVKV SCKASGYTFT GHYMYWMRQA PGQGLEWMGW INPNSGGTNY  60
AQKFQDRVTM TRDTSISTAY MELSRLRSDD TAVYYCARGR YGSSWYGGFE YWGQGTLVTV  120
SS                                                                 122

SEQ ID NO: 147          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 147
ggatacacct tcaccggcca ctat                                         24

SEQ ID NO: 148          moltype = AA   length = 8
FEATURE                 Location/Qualifiers
```

-continued

```
REGION                 1..8
                       note = Synthetic
source                 1..8
                       mol_type = protein
                       organism = synthetic construct
SEQUENCE: 148
GYTFTGHY                                                          8

SEQ ID NO: 149         moltype = DNA   length = 24
FEATURE                Location/Qualifiers
misc_feature           1..24
                       note = Synthetic
source                 1..24
                       mol_type = other DNA
                       organism = synthetic construct
SEQUENCE: 149
atcaacccta acagtggtgg caca                                        24

SEQ ID NO: 150         moltype = AA   length = 8
FEATURE                Location/Qualifiers
REGION                 1..8
                       note = Synthetic
source                 1..8
                       mol_type = protein
                       organism = synthetic construct
SEQUENCE: 150
INPNSGGT                                                          8

SEQ ID NO: 151         moltype = DNA   length = 45
FEATURE                Location/Qualifiers
misc_feature           1..45
                       note = Synthetic
source                 1..45
                       mol_type = other DNA
                       organism = synthetic construct
SEQUENCE: 151
gcgagaggga gatatggcag tagctggtac gggggggtttg agtac               45

SEQ ID NO: 152         moltype = AA   length = 15
FEATURE                Location/Qualifiers
REGION                 1..15
                       note = Synthetic
source                 1..15
                       mol_type = protein
                       organism = synthetic construct
SEQUENCE: 152
ARGRYGSSWY GGFEY                                                  15

SEQ ID NO: 153         moltype = DNA   length = 321
FEATURE                Location/Qualifiers
misc_feature           1..321
                       note = Synthetic
source                 1..321
                       mol_type = other DNA
                       organism = synthetic construct
SEQUENCE: 153
gacatccaga tgacccagtc tccatcttcc gtgtctgcat ctgttggaga cagagtcacc  60
atcacttgtc gggcgagtca gggtattacc agctggttag cctggtatca gcagaaacca  120
gggaaagccc ctaacctcct gatctatgct gcagccagtt tacaaagtgg ggtcccatca  180
aggttcagcg gcagtggatc tgggacggat ttcactctca ccatcagcag cctgcagcct  240
gaagacttta caacttacta ttgtcaacag gcttacagtc tccctctcac tttcggcgga  300
gggaccaagg tggagatcaa a                                            321

SEQ ID NO: 154         moltype = AA   length = 107
FEATURE                Location/Qualifiers
REGION                 1..107
                       note = Synthetic
source                 1..107
                       mol_type = protein
                       organism = synthetic construct
SEQUENCE: 154
DIQMTQSPSS VSASVGDRVT ITCRASQGIT SWLAWYQQKP GKAPNLLIYA AASLQSGVPS  60
RFSGSGSGTD FTLTISSLQP EDFTTYYCQQ AYSLPLTFGG GTKVEIK              107

SEQ ID NO: 155         moltype = DNA   length = 18
FEATURE                Location/Qualifiers
misc_feature           1..18
                       note = Synthetic
source                 1..18
```

-continued

```
                         mol_type = other DNA
                         organism = synthetic construct
SEQUENCE: 155
cagggtatta ccagctgg                                              18

SEQ ID NO: 156          moltype = AA   length = 6
FEATURE                 Location/Qualifiers
REGION                  1..6
                        note = Synthetic
source                  1..6
                        mol_type = protein
                        organism = synthetic construct
SEQUENCE: 156
QGITSW                                                           6

SEQ ID NO: 157          moltype =    length =
SEQUENCE: 157
000

SEQ ID NO: 158          moltype =    length =
SEQUENCE: 158
000

SEQ ID NO: 159          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 159
caacaggctt acagtctccc tctcact                                    27

SEQ ID NO: 160          moltype = AA   length = 9
FEATURE                 Location/Qualifiers
REGION                  1..9
                        note = Synthetic
source                  1..9
                        mol_type = protein
                        organism = synthetic construct
SEQUENCE: 160
QQAYSLPLT                                                        9

SEQ ID NO: 161          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 161
caggtgcagc tggtggagtc tggggggagc gtggtccagc ctgggaggtc cctgagactc   60
tcctgtgcag cctctggatt caccttcagt agctatggct tgcactgggt ccgccagtct  120
ccaggcaagg ggctggaatg ggtggcactt atatcatatg acggaagtaa taaatactat  180
gcagactccg tgaagggccg attcaccatc tccagagaca attccaagaa cacgctgtat  240
ctgcaaatga acagcctgag acctgaggac acggctggat atttctgtgc gaaatcccta  300
tatacaacca gctggtacgg gggctttgac tattggggcc agggaaccct ggtcaccgtc  360
tcctca                                                            366

SEQ ID NO: 162          moltype = AA   length = 122
FEATURE                 Location/Qualifiers
REGION                  1..122
                        note = Synthetic
source                  1..122
                        mol_type = protein
                        organism = synthetic construct
SEQUENCE: 162
QVQLVESGGG VVQPGRSLRL SCAASGFTFS SYGLHWVRQS PGKGLEWVAL ISYDGSNKYY   60
ADSVKGRFTI SRDNSKNTLY LQMNSLRPED TAGYFCAKSL YTTSWYGGFD YWGQGTLVTV  120
SS                                                                122

SEQ ID NO: 163          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 163
```

-continued

```
ggattcacct tcagtagcta tggc                                           24

SEQ ID NO: 164          moltype = AA  length = 8
FEATURE                 Location/Qualifiers
REGION                  1..8
                        note = Synthetic
source                  1..8
                        mol_type = protein
                        organism = synthetic construct
SEQUENCE: 164
GFTFSSYG                                                             8

SEQ ID NO: 165          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 165
atatcatatg acggaagtaa taaa                                           24

SEQ ID NO: 166          moltype = AA  length = 8
FEATURE                 Location/Qualifiers
REGION                  1..8
                        note = Synthetic
source                  1..8
                        mol_type = protein
                        organism = synthetic construct
SEQUENCE: 166
ISYDGSNK                                                             8

SEQ ID NO: 167          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 167
gcgaaatccc tatatacaac cagctggtac gggggctttg actat                    45

SEQ ID NO: 168          moltype = AA  length = 15
FEATURE                 Location/Qualifiers
REGION                  1..15
                        note = Synthetic
source                  1..15
                        mol_type = protein
                        organism = synthetic construct
SEQUENCE: 168
AKSLYTTSWY GGFDY                                                     15

SEQ ID NO: 169          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 169
gacatccaga tgacccagtc tccatcttcc gtgtctgcat ctgtaggaga cagagtcacc    60
atcacttgtc gggcgagtca gggtattaga agctggttag cctggtatca gcaaaaacca   120
gggaaagccc ctaacctcct gatctatgct gcgtccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt ccctccccac tttcggcccct   300
gggaccaaag tggatatcaa a                                             321

SEQ ID NO: 170          moltype = AA  length = 107
FEATURE                 Location/Qualifiers
REGION                  1..107
                        note = Synthetic
source                  1..107
                        mol_type = protein
                        organism = synthetic construct
SEQUENCE: 170
DIQMTQSPSS VSASVGDRVT ITCRASQGIR SWLAWYQQKP GKAPNLLIYA ASSLQSGVPS    60
RFSGSGSGTD FTLTISSLQP EDFATYYCQQ ANSFPPTFGP GTKVDIK                 107

SEQ ID NO: 171          moltype = DNA  length = 18
```

```
FEATURE              Location/Qualifiers
misc_feature         1..18
                     note = Synthetic
source               1..18
                     mol_type = other DNA
                     organism = synthetic construct
SEQUENCE: 171
cagggtatta gaagctgg                                              18

SEQ ID NO: 172       moltype = AA   length = 6
FEATURE              Location/Qualifiers
REGION               1..6
                     note = Synthetic
source               1..6
                     mol_type = protein
                     organism = synthetic construct
SEQUENCE: 172
QGIRSW                                                           6

SEQ ID NO: 173       moltype =    length =
SEQUENCE: 173
000

SEQ ID NO: 174       moltype =    length =
SEQUENCE: 174
000

SEQ ID NO: 175       moltype = DNA   length = 27
FEATURE              Location/Qualifiers
misc_feature         1..27
                     note = Synthetic
source               1..27
                     mol_type = other DNA
                     organism = synthetic construct
SEQUENCE: 175
caacaggcta acagtttccc tcccact                                   27

SEQ ID NO: 176       moltype = AA   length = 9
FEATURE              Location/Qualifiers
REGION               1..9
                     note = Synthetic
source               1..9
                     mol_type = protein
                     organism = synthetic construct
SEQUENCE: 176
QQANSFPPT                                                        9

SEQ ID NO: 177       moltype = DNA   length = 366
FEATURE              Location/Qualifiers
misc_feature         1..366
                     note = Synthetic
source               1..366
                     mol_type = other DNA
                     organism = synthetic construct
SEQUENCE: 177
gaggtgcagc tggtggagtc tggggggaggc ttggtacagc ctggggggtc cctgagactc   60
tcctgtgcag cctctgggtt caccttcagc aactatgcca tgacctgggt ccgccaggct  120
ccagggaagg ggctggagtg ggtctcaact atcagtggca gtggtgataa cacatactac  180
gcagactccg tgcagggccg gttcaccatc tccagaggcc attccaagaa cacgctgtat  240
ctgcaaatga acagcctgag agccgaggac acggccgtat attactgtgc gaaacctacg  300
tatagcagaa gctggtacgg tgcttttgat ttctggggcc aagggacaat ggtcaccgtc  360
tcttca                                                         366

SEQ ID NO: 178       moltype = AA   length = 122
FEATURE              Location/Qualifiers
REGION               1..122
                     note = Synthetic
source               1..122
                     mol_type = protein
                     organism = synthetic construct
SEQUENCE: 178
EVQLVESGGG LVQPGGSLRL SCAASGFTFS NYAMTWVRQA PGKGLEWVST ISGSGDNTYY   60
ADSVQGRFTI SRGHSKNTLY LQMNSLRAED TAVYYCAKPT YSRSWYGAFD FWGQGTMVTV  120
SS                                                            122

SEQ ID NO: 179       moltype = DNA   length = 24
FEATURE              Location/Qualifiers
misc_feature         1..24
                     note = Synthetic
```

-continued

```
source                   1..24
                         mol_type = other DNA
                         organism = synthetic construct
SEQUENCE: 179
gggttcacct tcagcaacta tgcc                                      24

SEQ ID NO: 180           moltype = AA  length = 8
FEATURE                  Location/Qualifiers
REGION                   1..8
                         note = Synthetic
source                   1..8
                         mol_type = protein
                         organism = synthetic construct
SEQUENCE: 180
GFTFSNYA                                                        8

SEQ ID NO: 181           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 181
atcagtggca gtggtgataa caca                                      24

SEQ ID NO: 182           moltype = AA  length = 8
FEATURE                  Location/Qualifiers
REGION                   1..8
                         note = Synthetic
source                   1..8
                         mol_type = protein
                         organism = synthetic construct
SEQUENCE: 182
ISGSGDNT                                                        8

SEQ ID NO: 183           moltype = DNA  length = 45
FEATURE                  Location/Qualifiers
misc_feature             1..45
                         note = Synthetic
source                   1..45
                         mol_type = other DNA
                         organism = synthetic construct
SEQUENCE: 183
gcgaaaccta cgtatagcag aagctggtac ggtgcttttg atttc               45

SEQ ID NO: 184           moltype = AA  length = 15
FEATURE                  Location/Qualifiers
REGION                   1..15
                         note = Synthetic
source                   1..15
                         mol_type = protein
                         organism = synthetic construct
SEQUENCE: 184
AKPTYSRSWY GAFDF                                                15

SEQ ID NO: 185           moltype = DNA  length = 321
FEATURE                  Location/Qualifiers
misc_feature             1..321
                         note = Synthetic
source                   1..321
                         mol_type = other DNA
                         organism = synthetic construct
SEQUENCE: 185
gacatccaga tgacccagtc tccatcctcc gtgtctgcat ctgtaggaga cagagtcacc  60
atcacttgtc gggcgagtca gggtattagc agctggttag cctggtatca gcagaaaccg  120
gggaaagccc ctcaactcct gatctatgct gcatccagat tgcaaagtgg ggtcccatca  180
aggttctggg gcagtggatc tgggacagat ttcactctca ccatcagcag cctgcagcct  240
gaagattttg caacttacta ttgtcaacag gctaacaatt tcccattcac tttcggccct  300
gggaccaaag tggatatcaa a                                          321

SEQ ID NO: 186           moltype = AA  length = 107
FEATURE                  Location/Qualifiers
REGION                   1..107
                         note = Synthetic
source                   1..107
                         mol_type = protein
                         organism = synthetic construct
SEQUENCE: 186
```

```
DIQMTQSPSS VSASVGDRVT ITCRASQGIS SWLAWYQQKP GKAPQLLIYA ASRLQSGVPS  60
RFWGSGSGTD FTLTISSLQP EDFATYYCQQ ANNFPFTFGP GTKVDIK                 107

SEQ ID NO: 187          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 187
cagggtatta gcagctgg                                                18

SEQ ID NO: 188          moltype = AA   length = 6
FEATURE                 Location/Qualifiers
REGION                  1..6
                        note = Synthetic
source                  1..6
                        mol_type = protein
                        organism = synthetic construct
SEQUENCE: 188
QGISSW                                                             6

SEQ ID NO: 189          moltype =    length =
SEQUENCE: 189
000

SEQ ID NO: 190          moltype =    length =
SEQUENCE: 190
000

SEQ ID NO: 191          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 191
caacaggcta acaatttccc attcact                                      27

SEQ ID NO: 192          moltype = AA   length = 9
FEATURE                 Location/Qualifiers
REGION                  1..9
                        note = Synthetic
source                  1..9
                        mol_type = protein
                        organism = synthetic construct
SEQUENCE: 192
QQANNFPFT                                                          9

SEQ ID NO: 193          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 193
caggttcagc tggtgcagtc tggagctgag gtgaagaagc ctggggcctc agtgaaggtc  60
tcctgcaagg cttctggtta caccttttacc agttatggta tcagctgggt gcgacaggcc  120
cctggacaag gccttgagtg gatgggatgg atccgcgctt acaatggtta cacaaactat  180
gcacagaagt tcagggcag agtcaccatg accacagaca catccacgaa caccgcctac  240
atggagctga ggaccctgaa ttctgacgat acggccgttt attactgtgc gagagatcga  300
tatagtggga gcttccacgg taactttgac tactggggcc agggaaccct ggtcaccgtc  360
tcctca                                                            366

SEQ ID NO: 194          moltype = AA   length = 122
FEATURE                 Location/Qualifiers
REGION                  1..122
                        note = Synthetic
source                  1..122
                        mol_type = protein
                        organism = synthetic construct
SEQUENCE: 194
QVQLVQSGAE VKKPGASVKV SCKASGYTFT SYGISWVRQA PGQGLEWMGW IRAYNGYTNY  60
AQKFQGRVTM TTDTSTNTAY MELRTLNSDD TAVYYCARDR YSGSFHGNFD YWGQGTLVTV  120
SS                                                                122
```

```
SEQ ID NO: 195          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 195
ggttacacct ttaccagtta tggt                                                  24

SEQ ID NO: 196          moltype = AA   length = 8
FEATURE                 Location/Qualifiers
REGION                  1..8
                        note = Synthetic
source                  1..8
                        mol_type = protein
                        organism = synthetic construct
SEQUENCE: 196
GYTFTSYG                                                                    8

SEQ ID NO: 197          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 197
atccgcgctt acaatggtta caca                                                  24

SEQ ID NO: 198          moltype = AA   length = 8
FEATURE                 Location/Qualifiers
REGION                  1..8
                        note = Synthetic
source                  1..8
                        mol_type = protein
                        organism = synthetic construct
SEQUENCE: 198
IRAYNGYT                                                                    8

SEQ ID NO: 199          moltype = DNA   length = 45
FEATURE                 Location/Qualifiers
misc_feature            1..45
                        note = Synthetic
source                  1..45
                        mol_type = other DNA
                        organism = synthetic construct
SEQUENCE: 199
gcgagagatc gatatagtgg gagcttccac ggtaactttg actac                           45

SEQ ID NO: 200          moltype = AA   length = 15
FEATURE                 Location/Qualifiers
REGION                  1..15
                        note = Synthetic
source                  1..15
                        mol_type = protein
                        organism = synthetic construct
SEQUENCE: 200
ARDRYSGSFH GNFDY                                                            15

SEQ ID NO: 201          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 201
gacatccaga tgacccagtc tccatcttcc gtgtctgcgt ctgtaggaga cagagtgacc  60
atcacttgtc gggcgagtca gggtattttc agctggttag cctggtatca gcagaaacca  120
gggaaagccc ctaaggtcct aatctatgct gcatccaatt tggaaagtgg ggtcccatca  180
aggttcagcg gcagtggatc tgggacagat ttcactctca ccatcagcag cctgcagcct  240
gaagattttg caacttacta ttgtcaacag gctaacagtt taccgctcac tttcggcgga  300
gggaccaagg tggagatcaa a                                                      321

SEQ ID NO: 202          moltype = AA   length = 107
FEATURE                 Location/Qualifiers
REGION                  1..107
                        note = Synthetic
```

-continued

```
source                  1..107
                        mol_type = protein
                        organism = synthetic construct
SEQUENCE: 202
DIQMTQSPSS VSASVGDRVT ITCRASQGIF SWLAWYQQKP GKAPKVLIYA ASNLESGVPS   60
RFSGSGSGTD FTLTISSLQP EDFATYYCQQ ANSLPLTFGG GTKVEIK                 107

SEQ ID NO: 203          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 203
cagggtattt tcagctgg                                                 18

SEQ ID NO: 204          moltype = AA   length = 6
FEATURE                 Location/Qualifiers
REGION                  1..6
                        note = Synthetic
source                  1..6
                        mol_type = protein
                        organism = synthetic construct
SEQUENCE: 204
QGIFSW                                                              6

SEQ ID NO: 205          moltype =    length =
SEQUENCE: 205
000

SEQ ID NO: 206          moltype =    length =
SEQUENCE: 206
000

SEQ ID NO: 207          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 207
caacaggcta acagtttacc gctcact                                       27

SEQ ID NO: 208          moltype = AA   length = 9
FEATURE                 Location/Qualifiers
REGION                  1..9
                        note = Synthetic
source                  1..9
                        mol_type = protein
                        organism = synthetic construct
SEQUENCE: 208
QQANSLPLT                                                           9

SEQ ID NO: 209          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 209
gaggtgcagc tggtggagtc tgggggaggc ttggtccagc ctggggggtc cctgagactc   60
tcctgtgcag cctctggatt caccttcagt acctattcta tgcactgggt ccgccaggct  120
ccagggaagg gactggaata tgtttcaact attaataata tgggggatac cacatattat  180
gcagactctg tgaagggcag attcaccatc tccagagaca attccaagaa cacgctgtat  240
cttcaactgg gcagcctgag acctgaggac atggctgtgt attactgtgc gagacagacg  300
tataccagca gctggtacgg ggggttcgac tcctggggcc agggaaccct ggtcaccgtc  360
tcctca                                                             366

SEQ ID NO: 210          moltype = AA   length = 122
FEATURE                 Location/Qualifiers
REGION                  1..122
                        note = Synthetic
source                  1..122
                        mol_type = protein
                        organism = synthetic construct
SEQUENCE: 210
```

-continued

```
EVQLVESGGG LVQPGGSLRL SCAASGFTFS TYSMHWVRQA PGKGLEYVST INNNGDTTYY    60
ADSVKGRFTI SRDNSKNTLY LQLGSLRPED MAVYYCARQT YTSSWYGGFD SWGQGTLVTV    120
SS                                                                   122

SEQ ID NO: 211          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 211
ggattcacct tcagtaccta ttct                                           24

SEQ ID NO: 212          moltype = AA  length = 8
FEATURE                 Location/Qualifiers
REGION                  1..8
                        note = Synthetic
source                  1..8
                        mol_type = protein
                        organism = synthetic construct
SEQUENCE: 212
GFTFSTYS                                                             8

SEQ ID NO: 213          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 213
attaataata atggggatac caca                                           24

SEQ ID NO: 214          moltype = AA  length = 8
FEATURE                 Location/Qualifiers
REGION                  1..8
                        note = Synthetic
source                  1..8
                        mol_type = protein
                        organism = synthetic construct
SEQUENCE: 214
INNNGDTT                                                             8

SEQ ID NO: 215          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 215
gcgagacaga cgtataccag cagctggtac gggggggttcg actcc                   45

SEQ ID NO: 216          moltype = AA  length = 15
FEATURE                 Location/Qualifiers
REGION                  1..15
                        note = Synthetic
source                  1..15
                        mol_type = protein
                        organism = synthetic construct
SEQUENCE: 216
ARQTYTSSWY GGFDS                                                     15

SEQ ID NO: 217          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 217
gacatccaga tgacccagtc tccatcttcc gtgtctgcat ctgtaggcga cagagtcacc    60
atcacttgtc gggcgagtca gggtattacc agctggttag cctggtatca gcagaaacca    120
gggaaagccc ctaaactcct gatctatgct gcatccaatt tgcaaagtgg ggtcccatca    180
aggttcagcg gcagtggatc tgggacagat ttcactctca ccatcaccag cctgcagcct    240
gaggattttg caacttacta ttgtcaacag gctaacagtc tcccattcac tttcggccct    300
gggaccaaag tggatatcaa a                                              321
```

-continued

```
SEQ ID NO: 218          moltype = AA   length = 107
FEATURE                 Location/Qualifiers
REGION                  1..107
                        note = Synthetic
source                  1..107
                        mol_type = protein
                        organism = synthetic construct
SEQUENCE: 218
DIQMTQSPSS VSASVGDRVT ITCRASQGIT SWLAWYQQKP GKAPKLLIYA ASNLQSGVPS   60
RFSGSGSGTD FTLTITSLQP EDFATYYCQQ ANSLPFTFGP GTKVDIK               107

SEQ ID NO: 219          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 219
cagggtatta ccagctgg                                                18

SEQ ID NO: 220          moltype = AA   length = 6
FEATURE                 Location/Qualifiers
REGION                  1..6
                        note = Synthetic
source                  1..6
                        mol_type = protein
                        organism = synthetic construct
SEQUENCE: 220
QGITSW                                                              6

SEQ ID NO: 221          moltype =    length =
SEQUENCE: 221
000

SEQ ID NO: 222          moltype =    length =
SEQUENCE: 222
000

SEQ ID NO: 223          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 223
caacaggcta acagtctccc attcact                                      27

SEQ ID NO: 224          moltype = AA   length = 9
FEATURE                 Location/Qualifiers
REGION                  1..9
                        note = Synthetic
source                  1..9
                        mol_type = protein
                        organism = synthetic construct
SEQUENCE: 224
QQANSLPFT                                                           9

SEQ ID NO: 225          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 225
gaggtgcagc tggtggagtc tggggggaggc ttggtacagc ctggggggtc cctgagactc   60
tcctgtgcag cctctggatt cacccttagc agctatgcca tgagctgggt ccgccaggct  120
ccagggaagg ggctggagtg ggtctcagct attagtggta gtggtggcag cacatactac  180
gcagactccg tgaagggccg gttcaccatc tccagagaca attccaagaa ctcgctgtat  240
ctgcaattga acagcctgag agccgaggac acggccgtat attactgtgc gaagacgctg  300
tatactacca gctggtacgg gggcttccag cactgggggcc agggcaccct ggtcactgtc  360
tcctca                                                             366

SEQ ID NO: 226          moltype = AA   length = 122
FEATURE                 Location/Qualifiers
REGION                  1..122
                        note = Synthetic
```

-continued

```
source                    1..122
                          mol_type = protein
                          organism = synthetic construct
SEQUENCE: 226
EVQLVESGGG LVQPGGSLRL SCAASGFTLS SYAMSWVRQA PGKGLEWVSA ISGSGGSTYY    60
ADSVKGRFTI SRDNSKNSLY LQLNSLRAED TAVYYCAKTL YTTSWYGGFQ HWGQGTLVTV   120
SS                                                                   122

SEQ ID NO: 227            moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 227
ggattcaccc ttagcagcta tgcc                                           24

SEQ ID NO: 228            moltype = AA  length = 8
FEATURE                   Location/Qualifiers
REGION                    1..8
                          note = Synthetic
source                    1..8
                          mol_type = protein
                          organism = synthetic construct
SEQUENCE: 228
GFTLSSYA                                                              8

SEQ ID NO: 229            moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 229
attagtggta gtggtggcag caca                                           24

SEQ ID NO: 230            moltype = AA  length = 8
FEATURE                   Location/Qualifiers
REGION                    1..8
                          note = Synthetic
source                    1..8
                          mol_type = protein
                          organism = synthetic construct
SEQUENCE: 230
ISGSGGST                                                              8

SEQ ID NO: 231            moltype = DNA  length = 45
FEATURE                   Location/Qualifiers
misc_feature              1..45
                          note = Synthetic
source                    1..45
                          mol_type = other DNA
                          organism = synthetic construct
SEQUENCE: 231
gcgaagacgc tgtatactac cagctggtac gggggcttcc agcac                    45

SEQ ID NO: 232            moltype = AA  length = 15
FEATURE                   Location/Qualifiers
REGION                    1..15
                          note = Synthetic
source                    1..15
                          mol_type = protein
                          organism = synthetic construct
SEQUENCE: 232
AKTLYTTSWY GGFQH                                                      15

SEQ ID NO: 233            moltype = DNA  length = 321
FEATURE                   Location/Qualifiers
misc_feature              1..321
                          note = Synthetic
source                    1..321
                          mol_type = other DNA
                          organism = synthetic construct
SEQUENCE: 233
gacatccaga tgacccagtc tccatcttcc gtgtctgcat ctataggaga cagagtcacc    60
atcacttgtc gggcgagtca gggaatcagc agttggttag cctggtatca gcagaaacca   120
gggaaagtcc ctaagctcct gatctatgct gcgtcctctt tgcaaagtgg gttcccatca   180
```

```
aggttcagcg gcagtggatc tgggacagat ttcactctca ccatcagtag cctgcagccc    240
gaagattttg caacttacta ttgtcaacag actcacagtt tcccgtggac ggtcggccaa    300
gggaccaagg tggaaatcaa a                                              321

SEQ ID NO: 234         moltype = AA   length = 107
FEATURE                Location/Qualifiers
REGION                 1..107
                       note = Synthetic
source                 1..107
                       mol_type = protein
                       organism = synthetic construct
SEQUENCE: 234
DIQMTQSPSS VSASIGDRVT ITCRASQGIS SWLAWYQQKP GKVPKLLIYA ASSLQSGFPS    60
RFSGSGSGTD FTLTISSLQP EDFATYYCQQ THSFPWTVGQ GTKVEIK                  107

SEQ ID NO: 235         moltype = DNA   length = 18
FEATURE                Location/Qualifiers
misc_feature          1..18
                       note = Synthetic
source                 1..18
                       mol_type = other DNA
                       organism = synthetic construct
SEQUENCE: 235
cagggaatca gcagttgg                                                  18

SEQ ID NO: 236         moltype = AA   length = 6
FEATURE                Location/Qualifiers
REGION                 1..6
                       note = Synthetic
source                 1..6
                       mol_type = protein
                       organism = synthetic construct
SEQUENCE: 236
QGISSW                                                               6

SEQ ID NO: 237         moltype =    length =
SEQUENCE: 237
000

SEQ ID NO: 238         moltype =    length =
SEQUENCE: 238
000

SEQ ID NO: 239         moltype = DNA   length = 24
FEATURE                Location/Qualifiers
misc_feature          1..24
                       note = Synthetic
source                 1..24
                       mol_type = other DNA
                       organism = synthetic construct
SEQUENCE: 239
caacagactc acagtttccc gtgg                                           24

SEQ ID NO: 240         moltype = AA   length = 8
FEATURE                Location/Qualifiers
REGION                 1..8
                       note = Synthetic
source                 1..8
                       mol_type = protein
                       organism = synthetic construct
SEQUENCE: 240
QQTHSFPW                                                             8

SEQ ID NO: 241         moltype = DNA   length = 366
FEATURE                Location/Qualifiers
misc_feature          1..366
                       note = Synthetic
source                 1..366
                       mol_type = other DNA
                       organism = synthetic construct
SEQUENCE: 241
gaggtgcagc tggtggagtc tggggggaggc ttggtacagc ctggggggtc cctgagactc    60
tcctgtgcag cctctggatt caccccttagg agctatttca tgacctgggt ccgccaggtt    120
ccagggaagg ggctggaggg ggtctctagct attagtggca ttagtggtgg cacatactac    180
acagactccg ttaagggccg gttcaccatc tccagagaca attccaagaa cacgctgttt    240
ctgcaaatga acagcctgag agccgaggac acggccgtat atttctgtgc gagaacggtg    300
tatagtagta gttactacgg gggcttccag cactgggggcc agggcaccct ggtcaccgtc    360
tcctca                                                              366
```

```
SEQ ID NO: 242          moltype = AA   length = 122
FEATURE                 Location/Qualifiers
REGION                  1..122
                        note = Synthetic
source                  1..122
                        mol_type = protein
                        organism = synthetic construct
SEQUENCE: 242
EVQLVESGGG LVQPGGSLRL SCAASGFTLR SYFMTWVRQV PGKGLEGVSA ISGISGGTYY  60
TDSVKGRFTI SRDNSKNTLF LQMNSLRAED TAVYFCARTV YSSSYYGGFQ HWGQGTLVTV  120
SS                                                                 122

SEQ ID NO: 243          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 243
ggattcaccc ttaggagcta tttc                                         24

SEQ ID NO: 244          moltype = AA   length = 8
FEATURE                 Location/Qualifiers
REGION                  1..8
                        note = Synthetic
source                  1..8
                        mol_type = protein
                        organism = synthetic construct
SEQUENCE: 244
GFTLRSYF                                                            8

SEQ ID NO: 245          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 245
attagtggca ttagtggtgg caca                                         24

SEQ ID NO: 246          moltype = AA   length = 8
FEATURE                 Location/Qualifiers
REGION                  1..8
                        note = Synthetic
source                  1..8
                        mol_type = protein
                        organism = synthetic construct
SEQUENCE: 246
ISGISGGT                                                            8

SEQ ID NO: 247          moltype = DNA   length = 45
FEATURE                 Location/Qualifiers
misc_feature            1..45
                        note = Synthetic
source                  1..45
                        mol_type = other DNA
                        organism = synthetic construct
SEQUENCE: 247
gcgagaacgg tgtatagtag tagttactac gggggcttcc agcac                  45

SEQ ID NO: 248          moltype = AA   length = 15
FEATURE                 Location/Qualifiers
REGION                  1..15
                        note = Synthetic
source                  1..15
                        mol_type = protein
                        organism = synthetic construct
SEQUENCE: 248
ARTVYSSSYY GGFQH                                                   15

SEQ ID NO: 249          moltype = DNA   length = 321
FEATURE                 Location/Qualifiers
misc_feature            1..321
                        note = Synthetic
source                  1..321
                        mol_type = other DNA
                        organism = synthetic construct
```

```
SEQUENCE: 249
gacatccaga tgacccagtc tccatcttcc gtgtctgtat ctgtaggaga cagagtcacc    60
atcacttgtc gggcgagtca gggtattagc agttggttag cctggtatca gcagaaacca   120
gggaaagccc ctaagctcct gatctatgtt gcatccagtt tacaaagtgg ggtcccatca   180
aggttcagcg gcagtggatc tgggacagat ttcactctca ccatcagcag cctgcagcct   240
gaagattttg caacttacta ttgtcaacag actaacagtt tccctctcac tttcggcgga   300
gggaccaagg tggagatcaa a                                              321

SEQ ID NO: 250        moltype = AA  length = 107
FEATURE               Location/Qualifiers
REGION                1..107
                      note = Synthetic
source                1..107
                      mol_type = protein
                      organism = synthetic construct
SEQUENCE: 250
DIQMTQSPSS VSVSVGDRVT ITCRASQGIS SWLAWYQQKP GKAPKLLIYV ASSLQSGVPS    60
RFSGSGSGTD FTLTISSLQP EDFATYYCQQ TNSFPLTFGG GTKVEIK                  107

SEQ ID NO: 251        moltype = DNA  length = 18
FEATURE               Location/Qualifiers
misc_feature          1..18
                      note = Synthetic
source                1..18
                      mol_type = other DNA
                      organism = synthetic construct
SEQUENCE: 251
cagggtatta gcagttgg                                                  18

SEQ ID NO: 252        moltype = AA  length = 6
FEATURE               Location/Qualifiers
REGION                1..6
                      note = Synthetic
source                1..6
                      mol_type = protein
                      organism = synthetic construct
SEQUENCE: 252
QGISSW                                                               6

SEQ ID NO: 253        moltype =    length =
SEQUENCE: 253
000

SEQ ID NO: 254        moltype =    length =
SEQUENCE: 254
000

SEQ ID NO: 255        moltype = DNA  length = 27
FEATURE               Location/Qualifiers
misc_feature          1..27
                      note = Synthetic
source                1..27
                      mol_type = other DNA
                      organism = synthetic construct
SEQUENCE: 255
caacagacta acagtttccc tctcact                                        27

SEQ ID NO: 256        moltype = AA  length = 9
FEATURE               Location/Qualifiers
REGION                1..9
                      note = Synthetic
source                1..9
                      mol_type = protein
                      organism = synthetic construct
SEQUENCE: 256
QQTNSFPLT                                                            9

SEQ ID NO: 257        moltype = DNA  length = 366
FEATURE               Location/Qualifiers
misc_feature          1..366
                      note = Synthetic
source                1..366
                      mol_type = other DNA
                      organism = synthetic construct
SEQUENCE: 257
gaggtgcagc tggtggagtc tggggggaggc ttggtacagc ctggggggtc cctgagactc   60
tcctgtgcag cctctggatt cacccttagg agttatgtca tgtactgggt ccgccagggt   120
ccagggaagg ggctggaggg ggtctcaggt attagtggca gtagtggtgg cacatactac   180
acagactccg tgaagggccg gttcaccatc tccagagaca attccaagaa cacgctgttt   240
```

-continued

```
ctgcaaatga acagcctgag agccgaggac acggccgtat atttctgtgc gagatcggtg   300
tatagtacca cctggtacgg gggcttccag cactggggcc agggcaccct ggtcaccgtc   360
tcctca                                                              366

SEQ ID NO: 258          moltype = AA  length = 122
FEATURE                 Location/Qualifiers
REGION                  1..122
                        note = Synthetic
source                  1..122
                        mol_type = protein
                        organism = synthetic construct
SEQUENCE: 258
EVQLVESGGG LVQPGGSLRL SCAASGFTLR SYVMYWVRQG PGKGLEGVSG ISGSSGGTYY    60
TDSVKGRFTI SRDNSKNTLF LQMNSLRAED TAVYFCARSV YSTTWYGGFQ HWGQGTLVTV   120
SS                                                                  122

SEQ ID NO: 259          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 259
ggattcaccc ttaggagtta tgtc                                           24

SEQ ID NO: 260          moltype = AA  length = 8
FEATURE                 Location/Qualifiers
REGION                  1..8
                        note = Synthetic
source                  1..8
                        mol_type = protein
                        organism = synthetic construct
SEQUENCE: 260
GFTLRSYV                                                              8

SEQ ID NO: 261          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 261
attagtggca gtagtggtgg caca                                           24

SEQ ID NO: 262          moltype = AA  length = 8
FEATURE                 Location/Qualifiers
REGION                  1..8
                        note = Synthetic
source                  1..8
                        mol_type = protein
                        organism = synthetic construct
SEQUENCE: 262
ISGSSGGT                                                              8

SEQ ID NO: 263          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 263
gcgagatcgg tgtatagtac cacctggtac gggggcttcc agcac                    45

SEQ ID NO: 264          moltype = AA  length = 15
FEATURE                 Location/Qualifiers
REGION                  1..15
                        note = Synthetic
source                  1..15
                        mol_type = protein
                        organism = synthetic construct
SEQUENCE: 264
ARSVYSTTWY GGFQH                                                      15

SEQ ID NO: 265          moltype = DNA  length = 321
FEATURE                 Location/Qualifiers
misc_feature            1..321
```

```
                          note = Synthetic
source                    1..321
                          mol_type = other DNA
                          organism = synthetic construct
SEQUENCE: 265
gacatccaga tgacccagtc tccatcttcc gtgtctgtat ctgtgggaga cagagtcacc    60
atcacttgtc gggcgagtca ggttattagc agttggttag cctggtatca gctgaaacca   120
gggaaagccc ctaaactcct gatctatgct gcatccagtt tacaaagtgg ggtcccatca   180
aggttcagcg gcagtggatc tgggacagat ttcactctca ccatcagcgg cctgcagcct   240
gaagattttg cagtttacta ttgtcaacag actaacagtt tccctctcac tttcggcgga   300
gggaccaagg tggagatcaa a                                             321

SEQ ID NO: 266           moltype = AA  length = 107
FEATURE                  Location/Qualifiers
REGION                   1..107
                         note = Synthetic
source                   1..107
                         mol_type = protein
                         organism = synthetic construct
SEQUENCE: 266
DIQMTQSPSS VSVSVGDRVT ITCRASQVIS SWLAWYQLKP GKAPKLLIYA ASSLQSGVPS    60
RFSGSGSGTD FTLTISGLQP EDFAVYYCQQ TNSFPLTFGG GTKVEIK                 107

SEQ ID NO: 267           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 267
caggttatta gcagttgg                                                  18

SEQ ID NO: 268           moltype = AA  length = 6
FEATURE                  Location/Qualifiers
REGION                   1..6
                         note = Synthetic
source                   1..6
                         mol_type = protein
                         organism = synthetic construct
SEQUENCE: 268
QVISSW                                                                6

SEQ ID NO: 269           moltype =   length =
SEQUENCE: 269
000

SEQ ID NO: 270           moltype =   length =
SEQUENCE: 270
000

SEQ ID NO: 271           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 271
caacagacta acagtttccc tctcact                                        27

SEQ ID NO: 272           moltype = AA  length = 9
FEATURE                  Location/Qualifiers
REGION                   1..9
                         note = Synthetic
source                   1..9
                         mol_type = protein
                         organism = synthetic construct
SEQUENCE: 272
QQTNSFPLT                                                             9

SEQ ID NO: 273           moltype = DNA  length = 366
FEATURE                  Location/Qualifiers
misc_feature             1..366
                         note = Synthetic
source                   1..366
                         mol_type = other DNA
                         organism = synthetic construct
SEQUENCE: 273
```

-continued

```
gaggtgcagc tggtggagtc tggggggaaac ttggaacagc ctgggggggtc ccttagactc   60
tcctgtacag cctctggatt caccttttagc agatctgcca tgaactgggt ccgccgggct  120
ccagggaagg ggctggagtg ggtctcagga attagtggta gtggtggtcg aacatactac  180
gcagactccg tgaagggccg gttcaccatc tccagagaca attccaagaa tacgctatat  240
ctgcaaatga acagcctgag cgccgaggac acggccgcat attactgtgc gaaagattcg  300
tatactacca gttggtacgg aggtatggac gtctggggcc acgggaccac ggtcaccgtc  360
tcctca                                                             366
```

SEQ ID NO: 274          moltype = AA  length = 122
FEATURE                 Location/Qualifiers
REGION                  1..122
                        note = Synthetic
source                  1..122
                        mol_type = protein
                        organism = synthetic construct
SEQUENCE: 274
EVQLVESGGN LEQPGGSLRL SCTASGFTFS RSAMNWVRRA PGKGLEWVSG ISGSGGRTYY   60
ADSVKGRFTI SRDNSKNTLY LQMNSLSAED TAAYYCAKDS YTTSWYGGMD VWGHGTTVTV  120
SS                                                                 122

SEQ ID NO: 275          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 275
ggattcacct ttagcagatc tgcc                                          24

SEQ ID NO: 276          moltype = AA  length = 8
FEATURE                 Location/Qualifiers
REGION                  1..8
                        note = Synthetic
source                  1..8
                        mol_type = protein
                        organism = synthetic construct
SEQUENCE: 276
GFTFSRSA                                                             8

SEQ ID NO: 277          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 277
attagtggta gtggtggtcg aaca                                          24

SEQ ID NO: 278          moltype = AA  length = 8
FEATURE                 Location/Qualifiers
REGION                  1..8
                        note = Synthetic
source                  1..8
                        mol_type = protein
                        organism = synthetic construct
SEQUENCE: 278
ISGSGGRT                                                             8

SEQ ID NO: 279          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 279
gcgaaagatt cgtatactac cagttggtac ggaggtatgg acgtc                   45

SEQ ID NO: 280          moltype = AA  length = 15
FEATURE                 Location/Qualifiers
REGION                  1..15
                        note = Synthetic
source                  1..15
                        mol_type = protein
                        organism = synthetic construct
SEQUENCE: 280
AKDSYTTSWY GGMDV                                                    15
```

-continued

```
SEQ ID NO: 281            moltype = DNA   length = 321
FEATURE                   Location/Qualifiers
misc_feature              1..321
                          note = Synthetic
source                    1..321
                          mol_type = other DNA
                          organism = synthetic construct
SEQUENCE: 281
gacatccaga tgacccagtc tccatcttcc gtgtctgcat ctgtaggaga cagagtcacc    60
atcacttgtc gggcgagtca gggtattttc agctggttag cctggtatca gcagaaacca   120
ggaaaagccc ctaagctcct gatctatgct gcttccagtt tacaaagtgg ggtcccatca   180
agattcagcg gcagtggatc tgggacagat ttcactctca ccatcagcag cctgcagcct   240
gaggattttg caatttacta ttgtcaacag gctaacagtg tcccgatcac cttcggccaa   300
gggacacgac tggagattaa a                                             321

SEQ ID NO: 282            moltype = AA   length = 107
FEATURE                   Location/Qualifiers
REGION                    1..107
                          note = Synthetic
source                    1..107
                          mol_type = protein
                          organism = synthetic construct
SEQUENCE: 282
DIQMTQSPSS VSASVGDRVT ITCRASQGIF SWLAWYQQKP GKAPKLLIYA ASSLQSGVPS    60
RFSGSGSGTD FTLTISSLQP EDFAIYYCQQ ANSVPITFGQ GTRLEIK                 107

SEQ ID NO: 283            moltype = DNA   length = 18
FEATURE                   Location/Qualifiers
misc_feature              1..18
                          note = Synthetic
source                    1..18
                          mol_type = other DNA
                          organism = synthetic construct
SEQUENCE: 283
cagggtattt tcagctgg                                                  18

SEQ ID NO: 284            moltype = AA   length = 6
FEATURE                   Location/Qualifiers
REGION                    1..6
                          note = Synthetic
source                    1..6
                          mol_type = protein
                          organism = synthetic construct
SEQUENCE: 284
QGIFSW                                                                6

SEQ ID NO: 285            moltype =    length =
SEQUENCE: 285
000

SEQ ID NO: 286            moltype =    length =
SEQUENCE: 286
000

SEQ ID NO: 287            moltype = DNA   length = 27
FEATURE                   Location/Qualifiers
misc_feature              1..27
                          note = Synthetic
source                    1..27
                          mol_type = other DNA
                          organism = synthetic construct
SEQUENCE: 287
caacaggcta acagtgtccc gatcacc                                        27

SEQ ID NO: 288            moltype = AA   length = 9
FEATURE                   Location/Qualifiers
REGION                    1..9
                          note = Synthetic
source                    1..9
                          mol_type = protein
                          organism = synthetic construct
SEQUENCE: 288
QQANSVPIT                                                             9

SEQ ID NO: 289            moltype = DNA   length = 366
FEATURE                   Location/Qualifiers
misc_feature              1..366
                          note = Synthetic
```

-continued

```
source                      1..366
                            mol_type = other DNA
                            organism = synthetic construct
SEQUENCE: 289
gaggtgcagc tggtggagtc tggggggaggc ttggtacagc ctggggggtc cctgagactc   60
tcctgttcag cctctggatt caccttagc agctatgcca tgaactgggt ccgccaggct  120
ccagggaagg ggctggagtg ggtcaccgct attagtggca gtggtggtgg cacatactac  180
gcagactccg tgaagggccg gttcaccatc tccagagaca attccaagaa ctcgctgttt  240
ctgcaattga acagcctgag agccgaggac acggccgtgt attactgtgc gaaacaaacg  300
tataccagca gctggtacgg tggctttgat atctggggc aggggacaat ggtcaccgtc  360
tcttca                                                             366

SEQ ID NO: 290            moltype = AA   length = 122
FEATURE                   Location/Qualifiers
REGION                    1..122
                          note = Synthetic
source                    1..122
                          mol_type = protein
                          organism = synthetic construct
SEQUENCE: 290
EVQLVESGGG LVQPGGSLRL SCSASGFTFS SYAMNWVRQA PGKGLEWVTA ISGSGGGTYY   60
ADSVKGRFTI SRDNSKNSLF LQLNSLRAED TAVYYCAKQT YTSSWYGGFD IWGQGTMVTV  120
SS                                                                  122

SEQ ID NO: 291            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 291
ggattcacct ttagcagcta tgcc                                          24

SEQ ID NO: 292            moltype = AA   length = 8
FEATURE                   Location/Qualifiers
REGION                    1..8
                          note = Synthetic
source                    1..8
                          mol_type = protein
                          organism = synthetic construct
SEQUENCE: 292
GFTFSSYA                                                            8

SEQ ID NO: 293            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 293
attagtggca gtggtggtgg caca                                          24

SEQ ID NO: 294            moltype = AA   length = 8
FEATURE                   Location/Qualifiers
REGION                    1..8
                          note = Synthetic
source                    1..8
                          mol_type = protein
                          organism = synthetic construct
SEQUENCE: 294
ISGSGGGT                                                            8

SEQ ID NO: 295            moltype = DNA   length = 45
FEATURE                   Location/Qualifiers
misc_feature              1..45
                          note = Synthetic
source                    1..45
                          mol_type = other DNA
                          organism = synthetic construct
SEQUENCE: 295
gcgaaacaaa cgtataccag cagctggtac ggtggctttg atatc                   45

SEQ ID NO: 296            moltype = AA   length = 15
FEATURE                   Location/Qualifiers
REGION                    1..15
                          note = Synthetic
source                    1..15
```

-continued

```
                         mol_type = protein
                         organism = synthetic construct
SEQUENCE: 296
AKQTYTSSWY GGFDI                                              15

SEQ ID NO: 297          moltype = DNA   length = 321
FEATURE                 Location/Qualifiers
misc_feature            1..321
                         note = Synthetic
source                  1..321
                         mol_type = other DNA
                         organism = synthetic construct
SEQUENCE: 297
gacatccaga tgacccagtc gccatcttcc gtgtccgcgt ctgtaggaga cagagtcacc   60
atcacttgtc gggcgagtca gggtttttagt tcctggttag cctggtatca gcagatacca  120
gggaaagccc ccaagctcct gatctatgct gcatcaaggt tgcaaagtgg ggtcccatcc  180
aggttccgcg gcagtggatc tgggacagat ttcactctca ccatcagcag cctgcagcct  240
gaggattttg caacttacta ttgtcaacag gctaacagtt tcccgctcac tttcggcgga  300
gggaccaagg tggagatcaa a                                            321

SEQ ID NO: 298          moltype = AA   length = 107
FEATURE                 Location/Qualifiers
REGION                  1..107
                         note = Synthetic
source                  1..107
                         mol_type = protein
                         organism = synthetic construct
SEQUENCE: 298
DIQMTQSPSS VSASVGDRVT ITCRASQGFS SWLAWYQQIP GKAPKLLIYA ASRLQSGVPS   60
RFRGSGSGTD FTLTISSLQP EDFATYYCQQ ANSFPLTFGG GTKVEIK                107

SEQ ID NO: 299          moltype = DNA   length = 18
FEATURE                 Location/Qualifiers
misc_feature            1..18
                         note = Synthetic
source                  1..18
                         mol_type = other DNA
                         organism = synthetic construct
SEQUENCE: 299
cagggtttta gttcctgg                                           18

SEQ ID NO: 300          moltype = AA   length = 6
FEATURE                 Location/Qualifiers
REGION                  1..6
                         note = Synthetic
source                  1..6
                         mol_type = protein
                         organism = synthetic construct
SEQUENCE: 300
QGFSSW                                                        6

SEQ ID NO: 301          moltype =    length =
SEQUENCE: 301
000

SEQ ID NO: 302          moltype =    length =
SEQUENCE: 302
000

SEQ ID NO: 303          moltype = DNA   length = 27
FEATURE                 Location/Qualifiers
misc_feature            1..27
                         note = Synthetic
source                  1..27
                         mol_type = other DNA
                         organism = synthetic construct
SEQUENCE: 303
caacaggcta acagtttccc gctcact                                 27

SEQ ID NO: 304          moltype = AA   length = 9
FEATURE                 Location/Qualifiers
REGION                  1..9
                         note = Synthetic
source                  1..9
                         mol_type = protein
                         organism = synthetic construct
SEQUENCE: 304
QQANSFPLT                                                     9
```

-continued

```
SEQ ID NO: 305          moltype = AA   length = 167
FEATURE                 Location/Qualifiers
REGION                  1..167
                        note = Synthetic
source                  1..167
                        mol_type = protein
                        organism = synthetic construct
SEQUENCE: 305
SITGISPITE SLASLSTYND QSITFALEDE SYEIYVEDLK KDKKKDKVLL SYYESQHPSS   60
ESGDGVDGKM LMVTLSPTKD FWLQANNKEH SVELHKCEKP LPDQAFFVLH NRSFNCVSFE  120
CKTDPGVFIG VKDNHLALIK VDYSENLGSE NILFKLSEIL EHHHHHH                167

SEQ ID NO: 306          moltype = AA   length = 167
FEATURE                 Location/Qualifiers
REGION                  1..167
                        note = Synthetic
source                  1..167
                        mol_type = protein
                        organism = synthetic construct
SEQUENCE: 306
SITGISPITE SLASLSTYND QSITFALEDE SYEIYVEDLK KDKKKDKVLL SYYESQHPSS   60
ESGDGVDGKM LMVTLSPTKD FWLQANNKEH SVELHKCEKP LPDQAFFVLH NRSFNCVSFE  120
CKTDPGVFIG VKDNHLALIK VDYSENLGSE NILFKLSEIL EHHHHHH                167

SEQ ID NO: 307          moltype = DNA   length = 354
FEATURE                 Location/Qualifiers
misc_feature            1..354
                        note = Synthetic
source                  1..354
                        mol_type = other DNA
                        organism = synthetic construct
SEQUENCE: 307
caggtcacct tgaaggagtc tggtcctgtg ctggtgaaac ccacagagag cctcacgctg   60
acctgctccg tctctggatt ctcactcagt aatgttagaa tgggtgtgag ctggatccgt  120
cagtccccag ggaaggccct gggagtggct gcacacattt tttcgaatga cgaaaaatcc  180
tacaccacat ctctgaagac caggctcacc atctccaagg acacctccag aagccaggtg  240
gtccttacca tgaccgacat ggaccctggg gacacagcca catattactg tgcacggata  300
cggaatttgg cctttaatta ctggggccag ggaaccctgg tcaccgtctc ctca        354

SEQ ID NO: 308          moltype = AA   length = 118
FEATURE                 Location/Qualifiers
REGION                  1..118
                        note = Synthetic
source                  1..118
                        mol_type = protein
                        organism = synthetic construct
SEQUENCE: 308
QVTLKESGPV LVKPTESLTL TCSVSGFSLS NVRMGVSWIR QSPGKALEWL AHIFSNDEKS   60
YTTSLKTRLT ISKDTSRSQV VLTMTDMDPG DTATYYCARI RNLAFNYWGQ GTLVTVSS    118

SEQ ID NO: 309          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 309
ggattctcac tcagtaatgt tagaatgggt                                    30

SEQ ID NO: 310          moltype = AA   length = 10
FEATURE                 Location/Qualifiers
REGION                  1..10
                        note = Synthetic
source                  1..10
                        mol_type = protein
                        organism = synthetic construct
SEQUENCE: 310
GFSLSNVRMG                                                          10

SEQ ID NO: 311          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 311
attttttcga atgacgaaaa a                                             21
```

-continued

```
SEQ ID NO: 312            moltype = AA   length = 7
FEATURE                   Location/Qualifiers
REGION                    1..7
                          note = Synthetic
source                    1..7
                          mol_type = protein
                          organism = synthetic construct
SEQUENCE: 312
IFSNDEK                                                                   7

SEQ ID NO: 313            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 313
gcacggatac ggaatttggc ctttaattac                                         30

SEQ ID NO: 314            moltype = AA   length = 10
FEATURE                   Location/Qualifiers
REGION                    1..10
                          note = Synthetic
source                    1..10
                          mol_type = protein
                          organism = synthetic construct
SEQUENCE: 314
ARIRNLAFNY                                                                10

SEQ ID NO: 315            moltype = DNA   length = 339
FEATURE                   Location/Qualifiers
misc_feature              1..339
                          note = Synthetic
source                    1..339
                          mol_type = other DNA
                          organism = synthetic construct
SEQUENCE: 315
gacttcgtga tgacccagtc tccagactcc ctggctgtgt ctctgggcga gagggccacc   60
atcaactgca agtccagcca gagtgtgtta cacaggtcca gcaataagaa ctacttagct  120
tggtatcagc agaagccagg acagcctcct aacctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcaata ttatggtact  300
ctatttactt tcggccctgg gaccaaagtg gatatcaaa                          339

SEQ ID NO: 316            moltype = AA   length = 113
FEATURE                   Location/Qualifiers
REGION                    1..113
                          note = Synthetic
source                    1..113
                          mol_type = protein
                          organism = synthetic construct
SEQUENCE: 316
DFVMTQSPDS LAVSLGERAT INCKSSQSVL HRSSNKNYLA WYQQKPGQPP NLLIYWASTR   60
ESGVPDRFSG SGSGTDFTLT ISSLQAEDVA VYYCQQYYGT LFTFGPGTKV DIK          113

SEQ ID NO: 317            moltype = DNA   length = 36
FEATURE                   Location/Qualifiers
misc_feature              1..36
                          note = Synthetic
source                    1..36
                          mol_type = other DNA
                          organism = synthetic construct
SEQUENCE: 317
cagagtgtgt tacacaggtc cagcaataag aactac                                  36

SEQ ID NO: 318            moltype = AA   length = 12
FEATURE                   Location/Qualifiers
REGION                    1..12
                          note = Synthetic
source                    1..12
                          mol_type = protein
                          organism = synthetic construct
SEQUENCE: 318
QSVLHRSSNK NY                                                             12

SEQ ID NO: 319            moltype =   length =
SEQUENCE: 319
```

-continued

```
000

SEQ ID NO: 320          moltype =   length =
SEQUENCE: 320
000

SEQ ID NO: 321          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 321
cagcaatatt atggtactct atttact                                              27

SEQ ID NO: 322          moltype = AA   length = 9
FEATURE                 Location/Qualifiers
REGION                  1..9
                        note = Synthetic
source                  1..9
                        mol_type = protein
                        organism = synthetic construct
SEQUENCE: 322
QQYYGTLFT                                                                   9

SEQ ID NO: 323          moltype = AA   length = 537
FEATURE                 Location/Qualifiers
REGION                  1..537
                        note = hST2-hFc
source                  1..537
                        mol_type = protein
                        organism = synthetic construct
SEQUENCE: 323
KFSKQSWGLE NEALIVRCPR QGKPSYTVDW YYSQTNKSIP TQERNRVFAS GQLLKFLPAA   60
VADSGIYTCI VRSPTFNRTG YANVTIYKKQ SDCNVPDYLM YSTVSGSEKN SKIYCPTIDL  120
YNWTAPLEWF KNCQALQGSR YRAHKSFLVI DNVMTEDAGD YTCKFIHNEN GANYSVTATR  180
SFTVKDEQGF SLFPVIGAPA QNEIKEVEIG KNANLTCSAC FGKGTQFLAA VLWQLNGTKI  240
TDFGEPRIQQ EEGQNQSFSN GLACLDMVLR IADVKEEDLL LQYDCLALNL HGLRRHTVRL  300
SRKNPIDHHS DKTHTCPPCP APELLGGPSV FLFPPKPKDT LMISRTPEVT CVVVDVSHED  360
PEVKFNWYVD GVEVHNAKTK PREEQYNSTY RVVSVLTVLH QDWLNGKEYK CKVSNKALPA  420
PIEKTISKAK GQPREPQVYT LPPSRDELTK NQVSLTCLVK GFYPSDIAVE WESNGQPENN  480
YKTTPPVLDS DGSFFLYSKL TVDKSRWQQG NVFSCSVMHE ALHNHYTQKS LSLSPGK     537

SEQ ID NO: 324          moltype = AA   length = 543
FEATURE                 Location/Qualifiers
REGION                  1..543
                        note = hST2-mFc
source                  1..543
                        mol_type = protein
                        organism = synthetic construct
SEQUENCE: 324
KFSKQSWGLE NEALIVRCPR QGKPSYTVDW YYSQTNKSIP TQERNRVFAS GQLLKFLPAA   60
VADSGIYTCI VRSPTFNRTG YANVTIYKKQ SDCNVPDYLM YSTVSGSEKN SKIYCPTIDL  120
YNWTAPLEWF KNCQALQGSR YRAHKSFLVI DNVMTEDAGD YTCKFIHNEN GANYSVTATR  180
SFTVKDEQGF SLFPVIGAPA QNEIKEVEIG KNANLTCSAC FGKGTQFLAA VLWQLNGTKI  240
TDFGEPRIQQ EEGQNQSFSN GLACLDMVLR IADVKEEDLL LQYDCLALNL HGLRRHTVRL  300
SRKNPIDHHS EPRGPTIKPC PPCKCPAPNL LGGPSVFIFP PKIKDVLMIS LSPIVTCVVV  360
DVSEDDPDVQ ISWFVNNVEV HTAQTQTHRE DYNSTLRVVS ALPIQHQDWM SGKEFKCKVN  420
NKDLPAPIER TISKPKGSVR APQVYVLPPP EEEMTKKQVT LTCMVTDFMP EDIYVEWTNN  480
GKTELNYKNT EPVLDSDGSY FMYSKLRVEK KNWVERNSYS CSVVHEGLHN HHTTKSFSRT  540
PGK                                                                        543

SEQ ID NO: 325          moltype = AA   length = 884
FEATURE                 Location/Qualifiers
REGION                  1..884
                        note = hST2-hIL1RAcP-mFc
source                  1..884
                        mol_type = protein
                        organism = synthetic construct
SEQUENCE: 325
KFSKQSWGLE NEALIVRCPR QGKPSYTVDW YYSQTNKSIP TQERNRVFAS GQLLKFLPAA   60
VADSGIYTCI VRSPTFNRTG YANVTIYKKQ SDCNVPDYLM YSTVSGSEKN SKIYCPTIDL  120
YNWTAPLEWF KNCQALQGSR YRAHKSFLVI DNVMTEDAGD YTCKFIHNEN GANYSVTATR  180
SFTVKDEQGF SLFPVIGAPA QNEIKEVEIG KNANLTCSAC FGKGTQFLAA VLWQLNGTKI  240
TDFGEPRIQQ EEGQNQSFSN GLACLDMVLR IADVKEEDLL LQYDCLALNL HGLRRHTVRL  300
SRKNPIDHHS SERCDDWGLD TMRQIQVFED EPARIKCPLF EHFLKFNYST AHSAGLTLIW  360
YWTRQDRDLE EPINFRLPEN RISKEKDVLW FRPTLLNDTG NYTCMLRNTT YCSKVAFPLE  420
VVQKDSCFNS PMKLPVHKLY IEYGIQRITC PNVDGYFPSS VKPTITWYMG CYKIQNFNNV  480
```

-continued

```
IPEGMNLSFL IALISNNGNY TCVVTYPENG RTFHLTRTLT VKVVGSPKNA VPPVIHSPND  540
HVVYEKEPGE ELLIPCTVYF SFLMDSRNEV WWTIDGKKPD DITIDVTINE SISHSRTEDE  600
TRTQILSIKK VTSEDLKRSY VCHARSAKGE VAKAAKVKQK VPAPRYTVES GEPRGPTIKP  660
CPPCKCPAPN LLGGPSVFIF PPKIKDVLMI SLSPIVTCVV VDVSEDDPDV QISWFVNNVE  720
VHTAQTQTHR EDYNSTLRVV SALPIQHQDW MSGKEFKCKV NNKDLPAPIE RTISKPKGSV  780
RAPQVYVLPP PEEEMTKKQV TLTCMVTDFM PEDIYVEWTN NGKTELNYKN TEPVLDSDGS  840
YFMYSKLRVE KKNWVERNSY SCSVVHEGLH NHHTTKSFSR TPGK               884

SEQ ID NO: 326             moltype = AA  length = 880
FEATURE                    Location/Qualifiers
REGION                     1..880
                           note = mST2-mIL1RAcP-mFc
source                     1..880
                           mol_type = protein
                           organism = synthetic construct
SEQUENCE: 326
SKSSWGLENE ALIVRCPQRG RSTYPVEWYY SDTNESIPTQ KRNRIFVSRD RLKFLPARVE  60
DSGIYACVIR SPNLNKTGYL NVTIHKKPPS CNIPDYLMYS TVRGSDKNFK ITCPTIDLYN  120
WTAPVQWFKN CKALQEPRFR AHRSYLFIDN VTHDDEGDYT CQFTHAENGT NYIVTATRSF  180
TVEEKGFSMF PVITNPPYNH TMEVEIGKPA SIACSACFGK GSHFLADVLW QINKTVVGNF  240
GEARIQEEEG RNESSSNDMD CLTSVLRITG VTEKDLSLEY DCLALNLHGM IRHTIRLRRK  300
QPIDHRSERC DDWGLDTMRQ IQVFEDEPAR IKCPLFEHPL KYNYSTAHSS GLTLIWYWTR  360
QDRDLEEPIN FRLPENRISK EKDVLWFRPT LLNDTGNYTC MLRNTTYCSK VAFPLEVVQK  420
DSCFNSAMRF PVHKMYIEHG IHKITCPNVD GYFPSSVKPS VTWYKGCTEI VDFHNVLPEG  480
MNLSFFIPLV SNNGNYTCVV TYPENGRLFH LTRTVTVKVV GSPKDALPPQ IYSPNDRVVY  540
EKEPGEELVI PCKVYFSFIM DSHNEVWWTI DGKKPDDVTV DITINESVSY SSTEDETRTQ  600
ILSIKKVTPE DLRRNYVCHA RNTKGEAEQA AKVKQKVIPP RYTVESGEPR GPTIKPCPPC  660
KCPAPNLLGG PSVFIFPPKI KDVLMISLSP IVTCVVVDVS EDDPDVQISW FVNNVEVHTA  720
QTQTHREDYN STLRVVSALP IQHQDWMSGK EFKCKVNNKD LPAPIERTIS KPKGSVRAPQ  780
VYVLPPPEEE MTKKQVTLTC MVTDFMPEDI YVEWTNNGKT ELNYKNTEPV LDSDGSYFMY  840
SKLRVEKKNW VERNSYSCSV VHEGLHNHHT TKSFSRTPGK                    880

SEQ ID NO: 327             moltype = AA  length = 876
FEATURE                    Location/Qualifiers
REGION                     1..876
                           note = hST2-hL1RAcP-hFc
source                     1..876
                           mol_type = protein
                           organism = synthetic construct
SEQUENCE: 327
KFSKQSWGLE NEALIVRCPR QGKPSYTVDW YYSQTNKSIP TQERNRVFAS GQLLKFLPAA  60
VADSGIYTCI VRSPTFNRTG YANVTIYKKQ SDCNVPDYLM YSTVSGSEKN SKIYCPTIDL  120
YNWTAPLEWF KNCQALQGSR YRAHKSFLVI DNVMTEDAGD YTCKFIHNEN GANYSVTATR  180
SFTVKDEQGF SLFPVIGAPA QNEIKEVEIG KNANLTCSAC FGKGTQFLAA VLWQLNGTKI  240
TDFGEPRIQQ EEGQNQSFSN GLACLDMVLR IADVKEEDLL LQYDCLALNL HGLRRHTVRL  300
SRKNPIDHHS SERCDDWGLD TMRQIQVFED EPARIKCPLF EHFLKFNYST AHSAGLTLIW  360
YWTRQDRDLE EPINFRLPEN RISKEKDVLW FRPTLLNDTG NYTCMLRNTT YCSKVAFPLE  420
VVQKDSCFNS PMKLPVHKLY IEYGIQRITC PNVDGYFPSS VKPTITWYMG CYKIQNFNNV  480
IPEGMNLSFL IALISNNGNY TCVVTYPENG RTFHLTRTLT VKVVGSPKNA VPPVIHSPND  540
HVVYEKEPGE ELLIPCTVYF SFLMDSRNEV WWTIDGKKPD DITIDVTINE SISHSRTEDE  600
TRTQILSIKK VTSEDLKRSY VCHARSAKGE VAKAAKVKQK VPAPRYTVED KTHTCPPCPA  660
PELLGGPSVF LFPPKPKDTL MISRTPEVTC VVVDVSHEDP EVKFNWYVDG VEVHNAKTKP  720
REEQYNSTYR VVSVLTVLHQ DWLNGKEYKC KVSNKALPAP IEKTISKAKG QPREPQVYTL  780
PPSRDELTKN QVSLTCLVKG FYPSDIAVEW ESNGQPENNY KTTPPVLDSD GSFFLYSKLT  840
VDKSRWQQGN VFSCSVMHEA LHNHYTQKSL SLSPGK                        876

SEQ ID NO: 328             moltype = AA  length = 310
FEATURE                    Location/Qualifiers
REGION                     1..310
                           note = human ST2 extracellular domain
source                     1..310
                           mol_type = protein
                           organism = synthetic construct
SEQUENCE: 328
KFSKQSWGLE NEALIVRCPR QGKPSYTVDW YYSQTNKSIP TQERNRVFAS GQLLKFLPAA  60
VADSGIYTCI VRSPTFNRTG YANVTIYKKQ SDCNVPDYLM YSTVSGSEKN SKIYCPTIDL  120
YNWTAPLEWF KNCQALQGSR YRAHKSFLVI DNVMTEDAGD YTCKFIHNEN GANYSVTATR  180
SFTVKDEQGF SLFPVIGAPA QNEIKEVEIG KNANLTCSAC FGKGTQFLAA VLWQLNGTKI  240
TDFGEPRIQQ EEGQNQSFSN GLACLDMVLR IADVKEEDLL LQYDCLALNL HGLRRHTVRL  300
SRKNPIDHHS                                                     310

SEQ ID NO: 329             moltype = AA  length = 306
FEATURE                    Location/Qualifiers
REGION                     1..306
                           note = mouse ST2 extracellular domain
source                     1..306
                           mol_type = protein
                           organism = synthetic construct
SEQUENCE: 329
```

```
SKSSWGLENE ALIVRCPQRG RSTYPVEWYY SDTNESIPTQ KRNRIFVSRD RLKFLPARVE   60
DSGIYACVIR SPNLNKTGYL NVTIHKKPPS CNIPDYLMYS TVRGSDKNFK ITCPTIDLYN  120
WTAPVQWFKN CKALQEPRFR AHRSYLFIDN VTHDDEGDYT CQFTHAENGT NYIVTATRSF  180
TVEEKGFSMF PVITNPPYNH TMEVEIGKPA SIACSACFGK GSHFLADVLW QINKTVVGNF  240
GEARIQEEEG RNESSSNDMD CLTSVLRITG VTEKDLSLEY DCLALNLHGM IRHTIRLRRK  300
QPIDHR                                                            306

SEQ ID NO: 330          moltype = AA  length = 339
FEATURE                 Location/Qualifiers
REGION                  1..339
                        note = human IL1RAcP extracellular domain
source                  1..339
                        mol_type = protein
                        organism = synthetic construct
SEQUENCE: 330
SERCDDWGLD TMRQIQVFED EPARIKCPLF EHFLKFNYST AHSAGLTLIW YWTRQDRDLE   60
EPINFRLPEN RISKEKDVLW FRPTLLNDTG NYTCMLRNTT YCSKVAFPLE VVQKDSCFNS  120
PMKLPVHKLY IEYGIQRITC PNVDGYFPSS VKPTITWYMG CYKIQNFNNV IPEGMNLSFL  180
IALISNNGNY TCVVTYPENG RTFHLTRTLT VKVVGSPKNA VPPVIHSPND HVVYEKEPGE  240
ELLIPCTVYF SFLMDSRNEV WWTIDGKKPD DITIDVTINE SISHSRTEDE TRTQILSIKK  300
VTSEDLKRSY VCHARSAKGE VAKAAKVKQK VPAPRYTVE                         339

SEQ ID NO: 331          moltype = AA  length = 339
FEATURE                 Location/Qualifiers
REGION                  1..339
                        note = mouse IL1RAcP extracellular domain
source                  1..339
                        mol_type = protein
                        organism = synthetic construct
SEQUENCE: 331
SERCDDWGLD TMRQIQVFED EPARIKCPLF EHFLKYNYST AHSSGLTLIW YWTRQDRDLE   60
EPINFRLPEN RISKEKDVLW FRPTLLNDTG NYTCMLRNTT YCSKVAFPLE VVQKDSCFNS  120
AMRFPVHKMY IEHGIHKITC PNVDGYFPSS VKPSVTWYKG CTEIVDFHNV LPEGMNLSFF  180
IPLVSNNGNY TCVVTYPENG RLFHLTRTVT VKVVGSPKDA LPPQIYSPND RVVYEKEPGE  240
ELVIPCKVYF SFIMDSHNEV WWTIDGKKPD DVTVDITINE SVSYSSTEDE TRTQILSIKK  300
VTPEDLRRNY VCHARNTKGE AEQAAKVKQK VIPPRYTVE                         339

SEQ ID NO: 332          moltype = AA  length = 227
FEATURE                 Location/Qualifiers
REGION                  1..227
                        note = human IgG1 Fc
source                  1..227
                        mol_type = protein
                        organism = synthetic construct
SEQUENCE: 332
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 333          moltype = AA  length = 233
FEATURE                 Location/Qualifiers
REGION                  1..233
                        note = mouse IgG2a Fc
source                  1..233
                        mol_type = protein
                        organism = synthetic construct
SEQUENCE: 333
EPRGPTIKPC PPCKCPAPNL LGGPSVFIFP PKIKDVLMIS LSPIVTCVVV DVSEDDPDVQ   60
ISWFVNNVEV HTAQTQTHRE DYNSTLRVVS ALPIQHQDWM SGKEFKCKVN NKDLPAPIER  120
TISKPKGSVR APQVYVLPPP EEEMTKKQVT LTCMVTDFMP EDIYVEWTNN GKTELNYKNT  180
EPVLDSDGSY FMYSKLRVEK KNWVERNSYS CSVVHEGLHN HHTTKSFSRT PGK         233

SEQ ID NO: 334          moltype = AA  length = 167
FEATURE                 Location/Qualifiers
REGION                  1..167
                        note = M.fascicularis IL-33-6His
source                  1..167
                        mol_type = protein
                        organism = synthetic construct
SEQUENCE: 334
SITGISPITE SLASLSTYND QSITFALEDE SYEIYVEDLK KDKKKDKVLL SYYESQHPSS   60
ESGDGVDGKM LMVTLSPTKD FWLQANNKEH SVELHKCEKP LPDQAFFVLH NRSFNCVSFE  120
CKTDPGVFIG VKDNHLALIK VDYSENLGSE NILFKLSEIL EHHHHHH                167

SEQ ID NO: 335          moltype = AA  length = 117
FEATURE                 Location/Qualifiers
REGION                  1..117
                        note = HCVR-mouse surrogate IL-4R Ab
```

```
source                   1..117
                         mol_type = protein
                         organism = synthetic construct
SEQUENCE: 335
EVQLQQSGPE LVKPGASVRM SCKASGYTFT DYNIHWVKQS HGKSLEWIGY IYPNNGDNGY  60
NQKFRGKATL TVDKSSSTAY MELRSLTSDD SAVYYCARGR LRYFDVWGTG TTVTVSS     117

SEQ ID NO: 336           moltype = AA  length = 111
FEATURE                  Location/Qualifiers
REGION                   1..111
                         note = LCVR-mouse surrogate IL-4R Ab
source                   1..111
                         mol_type = protein
                         organism = synthetic construct
SEQUENCE: 336
NIVLTQSPAS LAVSLGQRAT ISCRASESVD NYGHSFMHWY QQKPGQPPKL LIYLASNLES  60
GVPARFSGSG SRTDFTLTLD PVEADDAATY YCQQYNEDPP TFGSGTKLEI K           111

SEQ ID NO: 337           moltype = AA  length = 124
FEATURE                  Location/Qualifiers
REGION                   1..124
                         note = Dupilumab HCVR
source                   1..124
                         mol_type = protein
                         organism = synthetic construct
SEQUENCE: 337
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVS                                                               124

SEQ ID NO: 338           moltype = AA  length = 112
FEATURE                  Location/Qualifiers
REGION                   1..112
                         note = Dupilumab LCVR
source                   1..112
                         mol_type = protein
                         organism = synthetic construct
SEQUENCE: 338
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IK          112

SEQ ID NO: 339           moltype = AA  length = 8
FEATURE                  Location/Qualifiers
REGION                   1..8
                         note = Dupilumab HCDR1
source                   1..8
                         mol_type = protein
                         organism = synthetic construct
SEQUENCE: 339
GFTFRDYA                                                           8

SEQ ID NO: 340           moltype = AA  length = 8
FEATURE                  Location/Qualifiers
REGION                   1..8
                         note = Dupilumab HCDR2
source                   1..8
                         mol_type = protein
                         organism = synthetic construct
SEQUENCE: 340
ISGSGGNT                                                           8

SEQ ID NO: 341           moltype = AA  length = 18
FEATURE                  Location/Qualifiers
REGION                   1..18
                         note = Dupilumab HCDR3
source                   1..18
                         mol_type = protein
                         organism = synthetic construct
SEQUENCE: 341
AKDRLSITIR PRYYGLDV                                                18

SEQ ID NO: 342           moltype = AA  length = 11
FEATURE                  Location/Qualifiers
REGION                   1..11
                         note = Dupilumab LCDR1
source                   1..11
                         mol_type = protein
                         organism = synthetic construct
SEQUENCE: 342
```

-continued

```
QSLLYSIGYN Y                                                         11

SEQ ID NO: 343          moltype =    length =
SEQUENCE: 343
000

SEQ ID NO: 344          moltype = AA   length = 9
FEATURE                 Location/Qualifiers
REGION                  1..9
                        note = Dupilumab LCDR3
source                  1..9
                        mol_type = protein
                        organism = synthetic construct
SEQUENCE: 344
MQALQTPYT                                                           9

SEQ ID NO: 345          moltype = AA   length = 451
FEATURE                 Location/Qualifiers
REGION                  1..451
                        note = Dupilumab heavy chain
source                  1..451
                        mol_type = protein
                        organism = synthetic construct
SEQUENCE: 345
EVQLVESGGG LEQPGGSLRL SCAGSGFTFR DYAMTWVRQA PGKGLEWVSS ISGSGGNTYY    60
ADSVKGRFTI SRDNSKNTLY LQMNSLRAED TAVYYCAKDR LSITIRPRYY GLDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                  451

SEQ ID NO: 346          moltype = AA   length = 219
FEATURE                 Location/Qualifiers
REGION                  1..219
                        note = Dupilumab light chain
source                  1..219
                        mol_type = protein
                        organism = synthetic construct
SEQUENCE: 346
DIVMTQSPLS LPVTPGEPAS ISCRSSQSLL YSIGYNYLDW YLQKSGQSPQ LLIYLGSNRA    60
SGVPDRFSGS GSGTDFTLKI SRVEAEDVGF YYCMQALQTP YTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 347          moltype = AA   length = 207
FEATURE                 Location/Qualifiers
REGION                  1..207
                        note = human IL-4Ralpha
source                  1..207
                        mol_type = protein
                        organism = synthetic construct
SEQUENCE: 347
MKVLQEPTCV SDYMSISTCE WKMNGPTNCS TELRLLYQLV FLLSEAHTCI PENNGGAGCV    60
CHLLMDDVVS ADNYTLDLWA GQQLLWKGSF KPSEHVKPRA PGNLTVHTNV SDTLLLTWSN   120
PYPPDNYLYN HLTYAVNIWS ENDPADFRIY NVTYLEPSLR IAASTLKSGI SYRARVRAWA   180
QCYNTTWSEW SPSTKWHNSY REPFEQH                                       207

SEQ ID NO: 348          moltype = AA   length = 270
FEATURE                 Location/Qualifiers
REGION                  1..270
                        note = hIL33_O95760 (prior to proteolytic processing)
source                  1..270
                        mol_type = protein
                        organism = synthetic construct
SEQUENCE: 348
MKPKMKYSTN KISTAKWKNT ASKALCFKLG KSQQKAKEVC PMYFMKLRSG LMIKKEACYF    60
RRETTKRPSL KTGRKHKRHL VLAACQQQST VECFAFGISG VQKYTRALHD SSITGISPIT   120
EYLASLSTYN DQSITFALED ESYEIYVEDL KKDEKKDKVL LSYYESQHPS NESGDGVDGK   180
MLMVTLSPTK DFWLHANNKE HSVELHKCEK PLPDQAFFVL HNMHSNCVSF ECKTDPGVFI   240
GVKDNHLALI KVDSSENLCT ENILFKLSET                                    270

SEQ ID NO: 349          moltype = AA   length = 159
FEATURE                 Location/Qualifiers
REGION                  1..159
                        note = hIL33_mature_PEPTIDE (after proteolytic processing)
source                  1..159
                        mol_type = protein
```

-continued

```
                         organism = synthetic construct
SEQUENCE: 349
SITGISPITE YLASLSTYND QSITFALEDE SYEIYVEDLK KDEKKDKVLL SYYESQHPSN  60
ESGDGVDGKM LMVTLSPTKD FWLHANNKEH SVELHKCEKP LPDQAFFVLH NMHSNCVSFE  120
CKTDPGVFIG VKDNHLALIK VDSSENLCTE NILFKLSET                        159

SEQ ID NO: 350          moltype = AA   length = 12
FEATURE                 Location/Qualifiers
REGION                  1..12
                        note = Amino Acid residues 1-12 of SEQ ID NO: 349; also
                         corresponds to residues 112-123 of SEQ ID NO: 348 (Uniprot
                         O95760)
source                  1..12
                        mol_type = protein
                        organism = synthetic construct
SEQUENCE: 350
SITGISPITE YL                                                     12

SEQ ID NO: 351          moltype = AA   length = 87
FEATURE                 Location/Qualifiers
REGION                  1..87
                        note = Amino Acid residues 50-94 of SEQ ID NO: 349; also
                         corresponds to residues 161-205 of SEQ ID NO: 348 (Uniprot
                         O95760)
source                  1..87
                        mol_type = protein
                        organism = synthetic construct
SEQUENCE: 351
ITEYLASLST YNDQSITFAL EDESYEIYVE DLKKDEKKDK VLLSYYESQH PSNESGDGVD  60
GKMLMVTLSP TKDFWLHANN KEHSVEL                                     87

SEQ ID NO: 352          moltype = AA   length = 556
FEATURE                 Location/Qualifiers
REGION                  1..556
                        note = Human ST2 (See GenBank accession number NP_057316)
source                  1..556
                        mol_type = protein
                        organism = synthetic construct
SEQUENCE: 352
MGFWILAILT ILMYSTAAKF SKQSWGLENE ALIVRCPRQG KPSYTVDWYY SQTNKSIPTQ  60
ERNRVFASGQ LLKFLPAAVA DSGIYTCIVR SPTFNRTGYA NVTIYKKQSD CNVPDYLMYS  120
TVSGSEKNSK IYCPTIDLYN WTAPLEWFKN CQALQGSRYR AHKSFLVIDN VMTEDAGDYT  180
CKFIHNENGA NYSVTATRSF TVKDEQGFSL FPVIGAPAQN EIKEVEIGKN ANLTCSACFG  240
KGTQFLAAVL WQLNGTKITD FGEPRIQQEE GQNQSFSNGL ACLDMVLRIA DVKEEDLLLQ  300
YDCLALNLHG LRRHTVRLSR KNPIDHHSIY CIIAVCSVFL MLINVLVIIL KMFWIEATLL  360
WRDIAKPYKT RNDGKLYDAY VVYPRNYKSS TDGASRVEHF VHQILPDVLE NKCGYTLCIY  420
GRDMLPGEDV VTAVETNIRK SRRHIFILTP QITHNKEFAY EQEVALHCAL IQNDAKVILI  480
EMEALSELDM LQAEALQDSL QHLMKVQGTI KWREDHIANK RSLNSKFWKH VRYQMPVPSK  540
IPRKASSLTP LAAQKQ                                                 556

SEQ ID NO: 353          moltype = AA   length = 570
FEATURE                 Location/Qualifiers
REGION                  1..570
                        note = Human IL-1RAcP (See GenBank accession number Q9NPH3)
source                  1..570
                        mol_type = protein
                        organism = synthetic construct
SEQUENCE: 353
MTLLWCVVSL YFYGILQSDA SERCDDWGLD TMRQIQVFED EPARIKCPLF EHFLKFNYST  60
AHSAGLTLIW YWTRQDRDLE EPINFRLPEN RISKEKDVLW FRPTLLNDTG NYTCMLRNTT  120
YCSKVAFPLE VVQKDSCFNS PMKLPVHKLY IEYGIQRITC PNVDGYFPSS VKPTITWYMG  180
CYKIQNFNNV IPEGMNLSFL IALISNNGNY TCVVTYPENG RTFHLTRTLT VKVVGSPKNA  240
VPPVIHSPND HVVYEKEPGE ELLIPCTVYF SFLMDSRNEV WWTIDGKKPD DITIDVTINE  300
SISHSRTEDE TRTQILSIKK VTSEDLKRSY VCHARSAKGE VAKAAKVKQK VPAPRYTVEL  360
ACGFGATVLL VVILIVVYHV YWLEMVLFYR AHFGTDETIL DGKEYDIYVS YARNAEEEEF  420
VLLTLRGVLE NEFGYKLCIF DRDSLPGGIV TDETLSFIQK SRRLLVVLSP NYVLQGTQAL  480
LELKAGLENM ASRGNINVIL VQYKAVKETK VKELKRAKTV LTVIKWKGEK SKYPQGRFWK  540
QLQVAMPVKK SPRRSSSDEQ GLSYSSLKNV                                  570

SEQ ID NO: 354          moltype = AA   length = 449
FEATURE                 Location/Qualifiers
REGION                  1..449
                        note = HC OF H4H9675P
source                  1..449
                        mol_type = protein
                        organism = synthetic construct
SEQUENCE: 354
EVQLVESGGG LEQPGGSLRL SCTASGFTFS RSAMNWVRRA PGKGLEWVSG ISGSGGRTYY  60
ADSVKGRFTI SRDNSKNTLY LQMNSLSAED TAAYYCAKDS YTTSWYGGMD VWGHGTTVTV  120
```

```
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                     449

SEQ ID NO: 355         moltype = AA  length = 214
FEATURE                Location/Qualifiers
REGION                 1..214
                       note = LC OF H4H9675P
source                 1..214
                       mol_type = protein
                       organism = synthetic construct
SEQUENCE: 355
DIQMTQSPSS VSASVGDRVT ITCRASQGIF SWLAWYQQKP GKAPKLLIYA ASSLQSGVPS  60
RFSGSGSGTD FTLTISSLQP EDFAIYYCQQ ANSVPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 356         moltype = AA  length = 166
FEATURE                Location/Qualifiers
REGION                 1..166
                       note = HUMAN IL-33 WITH HEXA-HIS TAG (AMINO ACIDS 112-270
                        OF GENBANK ACCESSION NO. O95760)
source                 1..166
                       mol_type = protein
                       organism = synthetic construct
SEQUENCE: 356
MSITGISPIT EYLASLSTYN DQSITFALED ESYEIYVEDL KKDEKKDKVL LSYYESQHPS  60
NESGDGVDGK MLMVTLSPTK DFWLHANNKE HSVELHKCEK PLPDQAFFVL HNMHSNCVSF  120
ECKTDPGVFI GVKDNHLALI KVDSSENLCT ENILFKLSET HHHHHH                 166

SEQ ID NO: 357         moltype = DNA  length = 51
FEATURE                Location/Qualifiers
misc_feature           1..51
                       note = Synthetic
misc_feature           26
                       note = n is g or a
source                 1..51
                       mol_type = other DNA
                       organism = synthetic construct
SEQUENCE: 357
tataccatca caaagcctct cattanactt tgaatccaat gagtattact a            51

SEQ ID NO: 358         moltype = DNA  length = 51
FEATURE                Location/Qualifiers
misc_feature           1..51
                       note = Synthetic
misc_feature           26
                       note = n is g or t
source                 1..51
                       mol_type = other DNA
                       organism = synthetic construct
SEQUENCE: 358
ccaatctttt ctcatgaaga caccancatg acctcttatt cttatttata t            51
```

TREATMENT AND INHIBITION OF INFLAMMATORY LUNG DISEASES IN PATIENTS HAVING RISK ALLELES IN THE GENES ENCODING IL33 AND IL1RL1

REFERENCE TO A SEQUENCE LISTING

This application includes a Sequence Listing filed electronically as an XML file named 381203758SEQ, created on Jun. 7, 2023, with a size of 423,000 bytes. The Sequence Listing is incorporated herein by reference.

FIELD

This disclosure relates generally to the field of precision medicine. More particularly, the disclosure relates to the detection of risk alleles in genes encoding IL33 and IL1RL1, which risk alleles can be used to stratify inflammatory lung disease patients as having a high risk of developing one or more of these conditions and their eosinophilic subtypes.

BACKGROUND

Various publications, including patents, published applications, accession numbers, technical articles and scholarly articles are cited throughout the specification. Each of these cited publications is incorporated by reference, in its entirety and for all purposes, in this document.

Asthma and Chronic Obstructive Pulmonary Disease (COPD) are highly prevalent obstructive lung diseases with substantial unmet clinical need and significant diagnostic overlap, and there is increasing interest in the intersection of these conditions, termed asthma-COPD overlap syndrome (ACOS). There is a long-standing debate as to whether the two diseases have a shared etiology (the so-called "Dutch Hypothesis") or have independent mechanistic causes (the so-called "British Hypothesis). Despite recent progress in elucidating genetic contribution to common complex disease risk, including obstructive lung diseases, there is no well-established genetic finding linking asthma to COPD.

Genome-wide association studies (GWAS) have identified common genetic variants at interleukin-33 (IL33) and/or IL1RL1 that are associated with asthma. IL33, a pro-inflammatory cytokine and member of the interleukin-1 (IL-1) cytokine family, is expressed in subsets of cells in barrier tissues, including the lung epithelium. IL33 signals via a heterodimeric receptor complex composed of the IL33-specific receptor IL1RL1 (also known as ST2 or IL33R) and the IL-1RAcP co-receptor, common to several receptors of the IL-1 family.

In damaged tissues, previously sequestered IL33 is passively released into the extracellular compartment by necrotic cells and functions as an endogenous "danger signal" (alarmin) that activates inflammatory and repair pathways. Cigarette smoke induces IL33 expression in lung epithelial cells in mice, and IL33 expression is elevated in the bronchial epithelium of both asthma and COPD patients. In disease states in which inflammatory infiltrate and inflammatory cytokines are already present, the pool of IL33-responsive cells is increased and IL33 signaling further amplifies immune responses, resulting in pathologic inflammation and exaggerated immune responses, potentially driving chronic inflammatory diseases such as COPD.

There is also an asthma-COPD overlap syndrome (ACOS), characterized by symptoms common to both asthma and COPD. Nevertheless, clinical challenges remain in the capacity to diagnose ACOS, given the difficulty in separating asthma from COPD owing to the overlapping features in common.

Treatment challenges for asthma, COPD, and ACOS also remain, with resistance to corticosteroids (the standard of care) fairly commonplace. As well, other treatments such as IL-5 therapy has not worked well for the eosinophilic subsets of asthma and COPD.

Accordingly, there remains a need in the art to distinguish among asthma, COPD, and ACOS, as well as to more accurately identify patients who have the eosinophilic subsets of these disorders. Proper diagnoses can better direct a therapeutic regimen and improve patient outcomes.

SUMMARY

In a first aspect of the disclosure, a method for treating or inhibiting eosinophilic asthma comprises administering an IL33 antagonist or administering an IL33 antagonist and an IL-4R antagonist to a subject having one or more risk alleles associated with eosinophilic asthma in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that eosinophilic asthma is treated or inhibited in the subject.

In a second aspect of the disclosure, a method for treating or inhibiting eosinophilic Chronic Obstructive Pulmonary Disease (COPD) comprises administering an IL33 antagonist or administering an IL33 antagonist and an IL-4R antagonist to a subject having one or more risk alleles associated with eosinophilic COPD in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that eosinophilic COPD is treated or inhibited in the subject.

In a third aspect of the disclosure, a method for treating or inhibiting eosinophilic asthma-Chronic Obstructive Pulmonary Disease (COPD) overlap syndrome (ACOS), comprising administering an IL33 antagonist or administering an IL33 antagonist and an IL-4R antagonist to a subject having one or more risk alleles associated with eosinophilic asthma in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that eosinophilic COPD is treated or inhibited in the subject.

In a fourth aspect of the disclosure, a method for treating or inhibiting nasal polyps comprises administering an IL33 antagonist or administering an IL33 antagonist and an IL-4R antagonist to a subject having one or more risk alleles associated with nasal polyps in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that nasal polyps are treated or inhibited in the subject.

In a fifth aspect of the disclosure, a method for assessing risk of development of eosinophilic asthma, eosinophilic Chronic Obstructive Pulmonary Disease (COPD), or eosinophilic asthma COPD overlap syndrome (ACOS) comprises the steps of:

(A) detecting one or more risk alleles associated with eosinophilic asthma, eosinophilic COPD, or eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof in a sample obtained from a subject;

(B) (i) assigning a risk score of 1 to the subject when the subject has a risk allele in the intronic IL1RL1 variant rs1420101 (SEQ ID NO: 357) or variant in linkage disequilibrium thereof in one of the chromosome 2 homologs or a risk allele in the IL33 variant rs1342326 (SEQ ID NO: 358) or variant in linkage disequilibrium thereof in one of the chromosome 9 homologs, (B) (ii) assigning a risk score of 2 to the subject when the subject has a risk allele in the intronic IL1RL1 variant rs1420101 (SEQ ID NO: 357) or variant in linkage disequilibrium thereof in both of the chromosome 2 homologs, when the subject has a risk allele in the IL33 variant rs1342326 (SEQ ID NO: 358) or variant in linkage disequilibrium thereof in both of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in one of the chromosome 9 homologs, (B) (iii) assigning a risk score of 3 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in one of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in both of the chromosome 9 homologs, or (B) (iv) assigning a risk score of 4 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in both of the chromosome 9 homologs; and (C) categorizing the subject's risk of development of eosinophilic asthma, eosinophilic COPD, or eosinophilic ACOS, wherein a risk score of 1 indicates that the subject has a risk of developing the high-eosinophilic subset of eosinophilic asthma, high-eosinophilic subset of eosinophilic COPD, or high-eosinophilic subset of eosinophilic ACOS, a risk score of 2 indicates that the subject has an elevated risk of developing the high-eosinophilic subset of eosinophilic asthma, high-eosinophilic subset of eosinophilic COPD, or high-eosinophilic subset of eosinophilic ACOS, a risk score of 3 indicates that the subject has a high risk of developing the high-eosinophilic subset of eosinophilic asthma, high-eosinophilic subset of eosinophilic COPD, or high-eosinophilic subset of eosinophilic ACOS, and a risk score of 4 indicates that the subject has a very high risk of developing the high-eosinophilic subset of eosinophilic asthma, high-eosinophilic subset of eosinophilic COPD, or high-eosinophilic subset of eosinophilic ACOS. The method may further comprise treating or inhibiting one or more of the eosinophilic asthma, eosinophilic COPD, or eosinophilic ACOS, including the high eosinophilic subset thereof, in the subject by administering to the subject an IL33 antagonist or an IL33 antagonist and an IL-4R antagonist.

In a sixth aspect of the disclosure, an IL33 antagonist or a combination of an IL33 antagonist and an IL-4R antagonist is for use in the treatment or inhibition of, or in the manufacture of a medicament for the treatment or inhibition of any one of eosinophilic asthma, eosinophilic Chronic Obstructive Pulmonary Disease (COPD), eosinophilic asthma-Chronic Obstructive Pulmonary Disease overlap syndrome (ACOS), high-eosinophil eosinophilic asthma, high-eosinophil eosinophilic COPD, high-eosinophil eosinophilic ACOS, or nasal polyps when a patient thereof has one or more risk alleles associated with eosinophilic asthma, eosinophilic COPD, or eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof.

According to any one of these aspects, the subject may have at least one risk allele associated with eosinophilic asthma in the intronic IL1RL1 variant rs1420101 (SEQ ID NO: 357) or variant in linkage disequilibrium thereof, may have two risk alleles associated with eosinophilic asthma in the intronic IL1RL1 variant rs1420101 (SEQ ID NO: 357) or variant in linkage disequilibrium thereof, may have at least one risk allele associated with eosinophilic asthma in the IL33 variant rs1342326 (SEQ ID NO: 358) or variant in linkage disequilibrium thereof, or may have two risk alleles associated with eosinophilic asthma in the IL33 variant rs1342326 (SEQ ID NO: 358) or variant in linkage disequilibrium thereof, and may have further at least one risk allele associated with eosinophilic asthma in the IL33 variant rs1342326 (SEQ ID NO: 358) or variant in linkage disequilibrium thereof, and/or may further have two risk alleles associated with eosinophilic asthma in the IL33 variant rs1342326 (SEQ ID NO: 358) or variant in linkage disequilibrium thereof.

According to any one of these aspects, the method may comprise or the use may be for administering an IL33 antagonist to the subject or the method may comprise or the use may be for administering an IL33 antagonist and an IL-4R antagonist to the subject. The IL33 antagonist may comprise an IL33 trap or an antibody that specifically binds to IL33. The IL-4R antagonist may comprise an antibody that specifically binds to IL-4R.

According to any of these aspects, the IL33 trap may comprise a first IL33 binding domain comprising an IL33 binding portion of IL1RL1 and a second IL33 binding domain comprising an extracellular portion of IL-1RAcP. According to any of these aspects, the antibody or antigen-binding fragment thereof that specifically binds to IL33 may comprise the H1, H2, and H3 domains of SEQ ID NO: 274 and the L1, L2, and L3 domains of SEQ ID NO: 282. According to any of these aspects, the antibody or antigen-binding fragment thereof that specifically binds to IL-4R may comprise the H1, H2, and H3 domains of SEQ ID NO: 337 and the L1, L2, and L3 domains of SEQ ID NO: 338.

BRIEF DESCRIPTION OF THE DRAWINGS

FIG. 8 (Panels A, B, C, and D) shows the clinical characteristics of study participants stratified by capture reagent (Panel A) VCRome and (Panel B) xGEN, and chip platform (Panel C) OMNI and (Panel D) GSA.

FIG. 9 (Panels A and B) shows rs1420101 (IL1RL1, also known as ST2), s1342326 (IL33), rs146597587 (IL33-pLoF) and genetic score (total burden of rs1420101 and rs1342326 risk alleles) associations with (Panel A) Allergic Rhinitis and (Panel B) Nasal Polyps. Odds ratios for disease were calculated using logistic regression, with adjustment for age, $age^2$, sex, smoking status and principal components of ancestry. To test the burden of common risk variants, p-values and odds ratios were estimated for each individual score; in each case the comparison was to individuals with zero risk alleles. Additionally, overall trend test p-values are shown.

DETAILED DESCRIPTION

Figure 1:
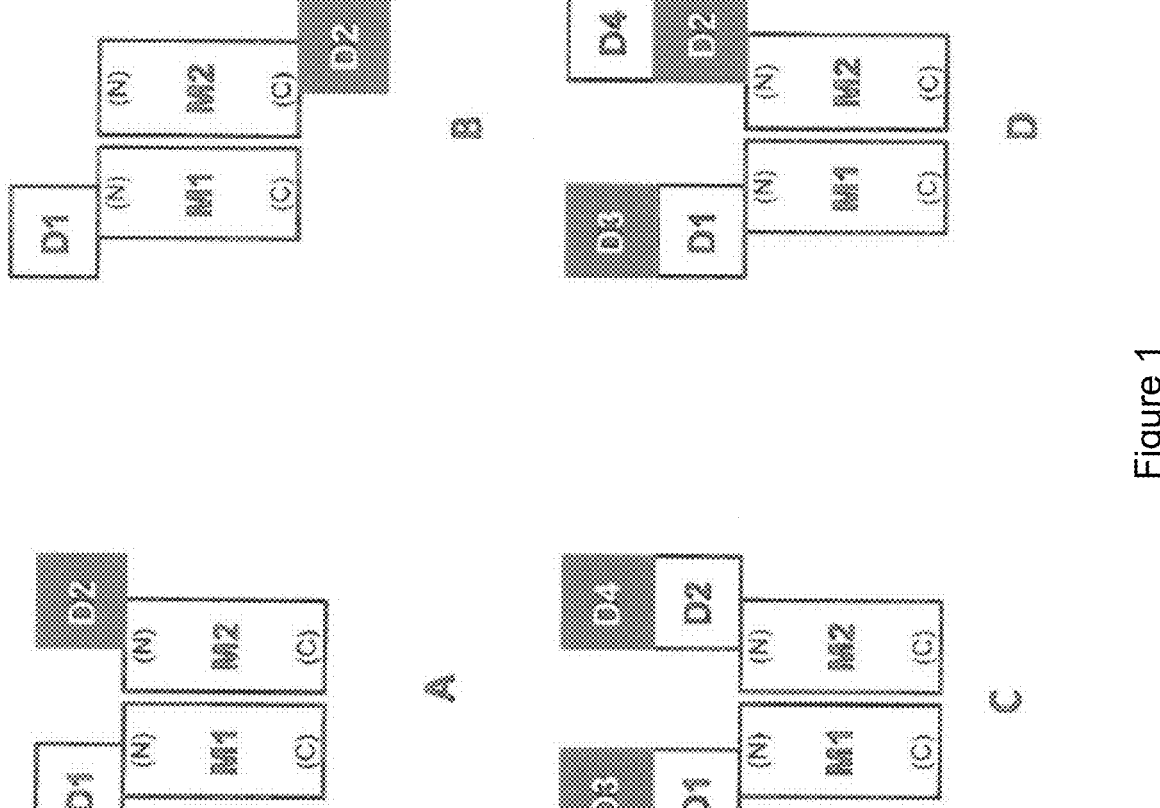
FIG. 1 (Panels A, B, C, and D) shows four exemplary arrangements of the individual components of the IL33 antagonists relative to one another. Panel A shows an arrangement in which a first IL33-binding domain (D1) is attached to the N-terminus of a first multimerizing domain (M1), and a second IL33-binding domain (D2) is attached to the N-terminus of a second multimerizing domain (M2). D1 is shown as a white box and D2 is shown as a black box to indicate that D1 and D2 are derived from different IL33 binding proteins. Panel B shows an arrangement in which a first IL33-binding domain (D1) is attached to the N-terminus of a first multimerizing domain (M1), and a second IL33-binding domain (D2) is attached to the C-terminus of a second multimerizing domain (M2). D1 is shown as a white box and D2 is shown as a black box to indicate that D1 and D2 are derived from different IL33 binding proteins. Panels C and D show arrangements comprising four IL33-binding domains, D1, D2, D3 and D4. In these arrangements, D3-D1-M1 and D4-D2-M2 are attached in tandem, wherein D3 is attached to the N-terminus of D1, and D1 is attached to the N-terminus of M1; and D4 is attached to the N-terminus of D2, and D2 is attached to the N-terminus of M2. In Panel C, D3 and D4 are identical or substantially identical to one another, and D1 and D2 are identical or substantially identical to one another. In Panel D, D1 and D4 are identical or substantially identical to one another, and D3 and D2 are identical or substantially identical to one another.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" and "patient" are used interchangeably and include any animal. Mammals are preferred, including companion (e.g., cat, dog) and farm mammals (e.g., pig, horse, cow), as well as rodents, including mice, rabbits, and rats, guinea pigs, and other rodents. Non-human primates are more preferred, and human beings are highly preferred.

The term "isolated" means removed and/or altered from the natural environment by the hand of a human being.

A "risk allele" includes alternative polymorphisms at a particular position that associate with a risk of developing a disease, disorder, or condition.

"Linkage disequilibrium" refers to a nonrandom association of alleles at two or more loci.

It has been observed in accordance with the disclosure that single nucleotide polymorphisms in IL1R rs1420101 (SEQ ID NO: 357) and IL33 rs1342326 (SEQ ID NO: 358) associate with increased risk of asthma, as well as high-eosinophil subsets of asthma, COPD, and ACOS. In addition, it was observed that individuals carrying a larger burden of these risk alleles across both loci have an attendant larger disease risk and, heterozygous carriers of rare pLOF variants in IL33 had lower median lifetime eosinophil counts and trends reflecting decreased risk of asthma, as well as trends reflecting decreased risks high-eosinophil subsets of asthma, COPD, and ACOS. It is believed that IL33 pathway genetic variants have not been previously associated with COPD and, it is further believed that there have not been any reported genetic links between asthma and COPD or genetic links between the IL33 pathway the risk of high-eosinophil subsets of asthma, COPD and ACOS. Furthermore, it was observed that single nucleotide polymorphisms in IL1R rs1420101 and IL33 rs1342326, considered individually and in aggregate, associate with increased risk of nasal polyps and allergic rhinitis. These data indicate a role for interleukin-33 blockade in the treatment of high-eosinophil forms of obstructive lung diseases such as asthma, COPD, and ACOS, as well as other upper airways diseases such as nasal polyps and their high-eosinophil subsets. Accordingly, the disclosure features methods for identifying risk, diagnosing, treating, and inhibiting asthma, COPD, and ACOS, especially the high-eosinophil subsets thereof.

In a first aspect, the disclosure features methods for assessing risk of development of an inflammatory lung disease. The inflammatory lung disease may be one or more of asthma, COPD, ACOS, or nasal polyps. The asthma may be eosinophilic asthma or high-eosinophil eosinophilic asthma. The COPD may be eosinophilic COPD or high-eosinophil eosinophilic COPD. The ACOS may be eosinophilic ACOS or high-eosinophil eosinophilic ACOS. In general, the methods comprise detecting one or more risk alleles associated with risk of development of such inflammatory lung diseases.

In some embodiments, the methods comprise detecting one or more risk alleles associated with eosinophilic asthma, eosinophilic COPD, eosinophilic ACOS, or nasal polyps in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof in a sample obtained from a subject, then assigning a risk score of 1 to the subject when the subject has a risk allele in the intronic IL1RL1 variant rs1420101 (SEQ ID NO: 357) or variant in linkage disequilibrium thereof in one of the chromosome 2 homologs or a risk allele in the IL33 variant rs1342326 (SEQ ID NO: 358) or variant in linkage disequilibrium thereof in one of the chromosome 9 homologs, assigning a risk score of 2 to the subject when the subject has a risk allele in the intronic IL1RL1 variant rs1420101 (SEQ ID NO: 357) or variant in linkage disequilibrium thereof in both of the chromosome 2 homologs, when the subject has a risk allele in the IL33 variant rs1342326 (SEQ ID NO: 358) or variant in linkage disequilibrium thereof in both of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in one of the chromosome 9 homologs, assigning a risk score of 3 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in one of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in both of the chromosome 9 homologs, or assigning a risk score of 4 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in both of the chromosome 9 homologs.

In some embodiments, the risk allele in the IL33 variant rs1342326 comprises a single nucleotide polymorphism (SNP). In some detailed embodiments, the IL33 variant comprises the SNP 9:6190076:A:C. (Human Genome GRCh38) The variant rs1342326 comprises the following nucleic acid sequence: CCAATCTTTTCTCATGAA-GACACCA[G/T]CATGACCTCTTATTCTTA TTTATAT (SEQ ID NO: 358).

In some embodiments, the risk allele in the IL1RL1 variant rs1420101 comprises an SNP. In some detailed embodiments, the IL1RL1 variant comprises the SNP 2:102341256:C:T (Human Genome GRCh38). The variant rs1342326 comprises the following nucleic acid sequence: TATACCATCACAAAGCCTCTCATTA[A/G]ACTTT-GAATCCAATGAGTATTACTA (SEQ ID NO: 357).

Detection may be according to any suitable methodology. The risk alleles may be detected, for example, by way of sequencing, genotyping, imputation, probing with complementary nucleic acid probes.

The methods may further comprise categorizing the subject's risk of development of eosinophilic asthma, eosinophilic COPD, or eosinophilic ACOS, wherein a risk score of 1 indicates that the subject has a risk of developing the high-eosinophil subset of eosinophilic asthma, high-eosinophil subset of eosinophilic COPD, or high-eosinophil subset of eosinophilic ACOS, a risk score of 2 indicates that the subject has an elevated risk of developing the high-eosinophil subset of eosinophilic asthma, high-eosinophil subset of eosinophilic COPD, or high-eosinophil subset of eosinophilic ACOS, a risk score of 3 indicates that the subject has a high risk of developing the high-eosinophil subset of eosinophilic asthma, high-eosinophil subset of eosinophilic COPD, or high-eosinophil subset of eosinophilic ACOS, and a risk score of 4 indicates that the subject has a very high risk of developing the high-eosinophil subset of eosinophilic asthma, high-eosinophil subset of eosinophilic COPD, or high-eosinophil subset of eosinophilic ACOS. In this scale, an elevated risk is greater than a risk but lesser than a high risk, and a very high risk is greater than a high risk. Thus, in terms of patient risk of developing disease, risk<elevated risk<high risk<very high risk, or risk score of 1<risk score of 2<risk score of 3<risk score of 4.

The methods may further comprise obtaining a sample from the subject. In general, the sample may comprise any sample from which the risk alleles may be detected. The sample may comprise a tissue sample or sputum. A tissue sample may include peripheral blood, airway or lung tissue.

The methods may further comprise identifying the subject as a candidate for treatment with an IL33 antagonist or a combination of an IL33 antagonist and an IL-4R antagonist. Based on the categorization of the subject's risk as a risk score of 1, risk score of 2, risk score of 3, or risk score of 4, the subject may benefit from a therapeutic regimen that inhibits eosinophilic asthma, eosinophilic COPD, eosinophilic ACOS, or the high eosinophil subsets thereof, or nasal polyps. An inhibitory therapeutic regimen may comprise adjustments in type, dose, dosing frequency, etc. for the IL33 antagonist, as well as whether or not to combine with an IL-4R antagonist and, if so, the type, dose, and dosing frequency, etc. for the IL-4R antagonist, for example, depending on the level of risk.

The methods may further comprise detecting increased levels in eosinophil counts from blood or sputum isolated from the subject. Increased levels are those that are considered above normal levels or above levels typically observed in subjects that have the non-eosinophilic subset of asthma, COPD, or ACOS. The methods may further comprise isolating the blood or sputum from the subject for this purpose.

The methods may further comprise administering an IL33 antagonist or administering an IL33 antagonist and an IL-4R antagonist to the subject. Such administration may be according to an amount effective to inhibit eosinophilic asthma, eosinophilic COPD, or eosinophilic ACOS, or the high-eosinophil subset thereof. In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In a second aspect, the disclosure features methods for treating or inhibiting eosinophilic asthma in a subject in need thereof. The eosinophilic asthma may be the low-eosinophil subset of eosinophilic asthma or may be the high eosinophil subset of eosinophilic asthma.

In some embodiments, the methods comprise administering an IL33 antagonist or administering an IL33 antagonist and an IL-4R antagonist to a subject having one or more risk alleles associated with eosinophilic asthma in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof, such that eosinophilic asthma is treated or inhibited in the subject.

In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In a third aspect, the disclosure features methods for treating or inhibiting eosinophilic COPD in a subject in need thereof. The eosinophilic COPD may be the low-eosinophil subset of eosinophilic COPD or may be the high eosinophil subset of eosinophilic COPD.

In some embodiments, the methods comprise administering an IL33 antagonist or administering an IL33 antagonist and an IL-4R antagonist to a subject having one or more risk alleles associated with eosinophilic COPD in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof, such that eosinophilic COPD is treated or inhibited in the subject.

In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In a fourth aspect, the disclosure features methods for treating or inhibiting eosinophilic ACOS in a subject in need thereof. The eosinophilic ACOS may be the low-eosinophil subset of eosinophilic ACOS or may be the high eosinophil subset of eosinophilic ACOS.

In some embodiments, the methods comprise administering an IL33 antagonist or administering an IL33 antagonist and an IL-4R antagonist to a subject having one or more risk alleles associated with eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof, such that eosinophilic ACOS is treated or inhibited in the subject.

In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In any of the methods described or exemplified herein, an IL33 antagonist may be administered as part of a therapeutic regimen. An IL33 antagonist may comprise any agent that inhibits the interaction of IL33 with one or more of its binding partners and, in so doing, inhibit IL33-mediated signaling. For example, an IL33 antagonist may bind to and/or interact with IL33, or with the IL33 receptor referred to as "suppression of tumorigenicity" (aka ST2), or with the IL33 co-receptor Interleukin-1 Receptor Accessory Protein (IL-1RAcP), or with a complex of any of the following: IL33/ST2, or ST2/IL-1RAcP.

Non-limiting examples of categories of IL33 antagonists include small molecule IL33 inhibitors, or receptor antagonists, or nucleic acids that hybridize under stringent conditions to nucleic acid sequences encoding either IL33, or an IL33 receptor or co-receptor (e.g., short interfering RNAs (siRNA) or clustered regularly interspaced short palindromic repeat RNAs (CRISPR-RNA or crRNA), including single guide RNAs (sgRNAs) having a crRNA and tracrRNA sequence. Other IL33 antagonists include proteins comprising a ligand-binding portion of an IL33 receptor (e.g., ST2), IL33-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, and anti-IL33 aptamers or portions thereof.

In preferred embodiments, an IL33 antagonist comprises an antibody that specifically binds to human IL33 (IL33 antibodies), or antigen-binding fragments thereof. The amino acid sequence identifiers for exemplary anti-IL33 antibodies for use in the methods described herein are shown in Table 1. Anti-IL33 antibodies may comprise any antibody described in U.S. Pat. No. 9,453,072, which is incorporated by reference in its entirety.

82, 98, 114, 130, 146, 162, 178, 194, 210, 226, 242, 258, 274, 290, and 308; and comprises three light chain CDRs (LCDR1, LCDR2 and LCDR3) contained within a light chain variable region (LCVR) amino acid sequence selected from the group consisting of SEQ ID NOs: 10, 26, 42, 58, 74, 90, 106, 122, 138, 154, 170, 186, 202, 218, 234, 250, 266, 282, 298, and 316.

In some embodiments, the anti-IL33 antibodies, or antigen-binding fragments thereof comprise a HCVR and LCVR (HCVR/LCVR) sequence pair of SEQ ID NO: 2/10, 18/26, 34/42, 50/58, 66/74, 82/90, 98/106, 114/122, 130/

TABLE 1

| IL33 Antibodies Amino Acid Sequence Identifiers | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| H1M9559N | 2 | 4 | 6 | 8 | 10 | 12 | 14 | 16 |
| H1M9566N | 18 | 20 | 22 | 24 | 26 | 28 | 30 | 32 |
| H1M9568N | 34 | 36 | 38 | 40 | 42 | 44 | 46 | 48 |
| H4H9629P | 50 | 52 | 54 | 56 | 58 | 60 | 62 | 64 |
| H4H9633P | 66 | 68 | 70 | 72 | 74 | 76 | 78 | 80 |
| H4H9640P | 82 | 84 | 86 | 88 | 90 | 92 | 94 | 96 |
| H4H9659P | 98 | 100 | 102 | 104 | 106 | 108 | 110 | 112 |
| H4H9660P | 114 | 116 | 118 | 120 | 122 | 124 | 126 | 128 |
| H4H9662P | 130 | 132 | 134 | 136 | 138 | 140 | 142 | 144 |
| H4H9663P | 146 | 148 | 150 | 152 | 154 | 156 | 158 | 160 |
| H4H9664P | 162 | 164 | 166 | 168 | 170 | 172 | 174 | 176 |
| H4H9665P | 178 | 180 | 182 | 184 | 186 | 188 | 190 | 192 |
| H4H9666P | 194 | 196 | 198 | 200 | 202 | 204 | 206 | 208 |
| H4H9667P | 210 | 212 | 214 | 216 | 218 | 220 | 222 | 224 |
| H4H9670P | 226 | 228 | 230 | 232 | 234 | 236 | 238 | 240 |
| H4H9671P | 242 | 244 | 246 | 248 | 250 | 252 | 254 | 256 |
| H4H9672P | 258 | 260 | 262 | 264 | 266 | 268 | 270 | 272 |
| H4H9675P | 274 | 276 | 278 | 280 | 282 | 284 | 286 | 288 |
| H4H9676P | 290 | 292 | 294 | 296 | 298 | 300 | 302 | 304 |
| H1M9565N | 308 | 310 | 312 | 314 | 316 | 318 | 320 | 322 |

In some embodiments, the IL33 antagonist comprises an anti-IL33 antibody, or antigen-binding fragment thereof, comprising a heavy chain variable region (HCVR), light chain variable region (LCVR), and/or complementarity determining regions (CDRs) of the amino acid sequences of the anti-IL33 antibodies as set forth in U.S. Pat. No. 9,453, 072 and in Table 1 herein. In some embodiments, the IL33 antagonist comprises the heavy chain complementarity determining regions (CDR; e.g., H1, H2, H3) of the heavy chain variable region comprising the amino acid sequence of SEQ ID NO: 274 and the light chain CDRs (e.g., L1, L2, L3) of the light chain variable region comprising the amino acid sequence of SEQ ID NO: 282. In some embodiments, the H1 comprises the amino acid sequence of SEQ ID NO: 276, the H2 comprises the amino acid sequence of SEQ ID NO: 278, and the H3 comprises the amino acid sequence of SEQ ID NO: 280. In some embodiments, the L1 comprises the amino acid sequence of SEQ ID NO: 284, the L2 comprises the amino acid sequence of SEQ ID NO: 286, and the L3 comprises the amino acid sequence of SEQ ID NO: 288. In yet other embodiments, the anti-IL33 antibody or antigen-binding fragment thereof comprises an HCVR comprising SEQ ID NO: 274 and an LCVR comprising SEQ ID NO: 282.

In some embodiments, the IL33 antibodies or antigen-binding fragments thereof comprise three heavy chain CDRs (HCDR1, HCDR2 and HCDR3) contained within a heavy chain variable region (HCVR) amino acid sequence selected from the group consisting of SEQ ID NO: 2, 18, 34, 50, 66, 138, 146/154, 162/170, 178/186, 194/202, 210/218, 226/ 234, 242/250, 258/266, 274/282, 290/298, or 308/316.

In some embodiments, the anti-IL33 antibodies, or antigen-binding fragments thereof comprise a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, and 310, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, and 312, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, and 318, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, and 320, or a substantially similar sequence thereof having at least 90%, at least 95%, at least 98% or at least 99% sequence identity.

In some preferred embodiments, the anti-IL33 antibodies or antigen-binding fragments thereof comprise HCDR1-

HCDR2-HCDR3-LCDR1-LCDR2-LCDR3 domains, respectively, having the amino acid sequences selected from the group consisting of: SEQ ID NOs: 4-6-8-12-14-16 (e.g. H1M9559N); 20-22-24-28-30-32 (e.g., H1M9566N); 36-38-40-44-46-48 (e.g., H1M9568N); 52-54-56-60-62-64 (e.g. H4H9629P); 68-70-72-76-78-80 (e.g., H4H9633P); 84-86-88-92-94-96 (e.g. H4H9640P); 100-102-104-108-110-112 (e.g., H4H9659P); 116-118-120-124-126-128 (e.g., H4H9660P); 132-134-136-140-142-144 (e.g., H4H9662P); 148-150-152-156-158-160 (e.g., H4H9663P); 164-166-168-172-174-176 (e.g., H4H9664P); 180-182-184-188-190-192 (e.g., H4H9665P); 196-198-200-204-206-208 (e.g., H4H9666P); 212-214-216-220-222-224 (e.g., H4H9667P); 228-230-232-236-238-240 (e.g., H4H9670P); 244-246-248-252-254-256 (e.g., H4H9671P); 260-262-264-268-270-272 (e.g., H4H9672P); 276-278-280-284-286-288 (e.g., H4H9675P); 292-294-296-300-302-304 (e.g., H4H9676P); and 310-312-314-318-320-322 (H1M9565N).

In some embodiments, the anti-IL33 antibodies, or antigen-binding fragments thereof, comprise the heavy and light chain CDR domains contained within heavy and light chain variable region (HCVR/LCVR) sequences of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, or308/316. The boundaries of CDRs may be according to the Kabat definition, the Chothia definition, or the AbM definition.

Other anti-IL33 antibodies and antigen-binding fragments thereof that may be used in the methods described herein are disclosed in European Publ. No. EP 1725261, PCT Publ. Nos. WO 2011/031600, WO 2015/099175, WO 2015/106080 (ANB020), WO 2016/077381, WO 2016/077366, or WO2016/156440, U.S. Pat. No. 8,187,596, and U.S. Publ. No. 2016/0168242, which are each incorporated herein by reference in their entirety.

In alternative preferred embodiments, an IL33 antagonist comprises an IL33 trap. IL33 traps comprise at least one IL33 binding domain, which comprises an IL33 binding portion of an IL33 receptor protein, designated ST2. In some embodiments, an IL33 trap further comprises an extracellular portion of an IL33 co-receptor, designated IL-1 receptor accessory protein, or IL-1RAcP. The IL33 trap may also comprise at least one multimerizing component, which functions to connect the various components of the trap with one another. The various components of the IL33 traps are described below and shown in FIG. 1. IL33 traps may comprise any trap described in U.S. Publ. No. 2014/0271642 and PCT Publ. No. WO 2014/152195, which are each incorporated herein by reference in their entirety.

The IL33 trap may comprise a first IL33 binding domain (D1) attached to a multimerizing domain (M). In some embodiments, the IL33 trap comprises a second IL33 binding domain (D2) attached to D1 and/or M. In some preferred embodiments, D1 comprises an IL33-binding portion of an ST2 protein. In some preferred embodiments, D2 comprises an extracellular portion of an IL-1RAcP protein.

The individual components of the IL33 traps may be arranged relative to one another in a variety of ways that result in functional antagonist molecules capable of binding IL33. For example, D1 and/or D2 may be attached to the N-terminus of M. In some embodiments, D1 and/or D2 is attached to the C-terminus of M. In other embodiments, D1 is attached to the N-terminus of D2, and D2 is attached to the N-terminus of M, resulting in an in-line fusion, from N- to C-terminus, of an antagonist molecule represented by the formula D1-D2-M. Other orientations of the individual components are disclosed elsewhere herein in FIG. 1.

The IL33 traps comprise at least one IL33 binding domain (sometimes referred to herein by the designation "D," or "D1," "D2," etc.). In some embodiments, the IL33 binding domain comprises an IL33-binding portion of an ST2 protein. An IL33-binding portion of an ST2 protein can comprise or consist of all or part of the extracellular domain of an ST2 protein. In preferred embodiments, an ST2 protein is a human ST2 protein, including the ST2 protein of amino acids 1-556 of accession number NP_057316.3 (SEQ ID NO: 352). In some alternative embodiments, the ST2 protein comprises an ST2 protein from a non-human species (e.g., mouse ST2, non-human primate ST2, etc.). An preferred IL33-binding portion of an ST2 protein is set forth herein as the amino acid sequence of SEQ ID NO: 328 (corresponding to the extracellular domain of human ST2 [K19-S328 of NCBI Accession No. NP_057316.3]). Other examples of an IL33-binding portion of an ST2 protein is set forth herein as the amino acid sequence of SEQ ID NO: 329 (corresponding to the extracellular domain of mouse ST2 [S27-R332 of NCBI Accession No. P14719]).

In some embodiments, the IL33 binding domain of the trap comprises an extracellular portion of an IL-1RAcP protein. In certain embodiments, an IL-1RAcP protein comprises a human IL-1RAcP protein, including an IL-1RAcP protein having the amino acid sequence of SEQ ID NO: 353. In some alternative embodiments, the IL-1RAcP protein comprises an IL-1RAcP protein from a non-human species (e.g., mouse IL-1RAcP, non-human primate IL-1RAcP, etc.). An exemplary extracellular portion of an IL-1RAcP protein is set forth herein as the amino acid sequence of SEQ ID NO: 330 (corresponding to the extracellular domain of human IL-1RAcP [S21-E359 of NCBI Accession No. Q9NPH3]). Another example of an extracellular portion of an IL-1RAcP protein is set forth herein as the amino acid sequence of SEQ ID NO: 331 (corresponding to the extracellular domain of mouse IL-1RAcP [S21-E359 of NCBI Accession No. Q61730]).

Non-limiting examples of IL33 traps for use in the methods are shown in Table 2, and include the IL33 traps designated "hST2-hFc," "hST2-mFc," "hST2-hIL1RAcP-mFc," "hST2-hIL1RAcP-hFc" and "mST2-mIL1RAcP-mFc." These correspond to SEQ ID NOs: 323, 324, 325, 326 and 327, respectively. IL33 receptor based traps may comprise an amino acid sequence that is at least about 80%, 85%, 90%, 91%, 92%, 93%, 94%, 95%, 96%, 97%, 98% or 99% identical to any of the exemplary IL33 receptor based traps set forth herein (e.g., SEQ ID NOs: 323, 324, 325, 326 and 327). IL33 traps may comprise D1 and/or D2 components having an amino acid sequence that is at least about 80%, 85%, 90%, 91%, 92%, 93%, 94%, 95%, 96%, 97%, 98% or 99% identical to any of the exemplary IL33 binding domain component amino acid sequences set forth herein (e.g., SEQ ID NOs: 328, 329, 330 and 331).

Five different exemplary IL33 traps were constructed. The first IL33 antagonist (hST2-hFc, SEQ ID NO: 323) includes the soluble extracellular region of human ST2 (SEQ ID NO: 328) fused at its C-terminus to the N-terminus of a human IgG1 Fc region (SEQ ID NO:332). The second IL33 antagonist (hST2-mFc, SEQ ID NO:324) consists of the soluble extracellular region of human ST2 (SEQ ID NO:328) fused at its C-terminus to the N-terminus of a mouse IgG2a Fc region (SEQ ID NO:333). The third IL33 antagonist (hST2-hIL1RAcP-mFc, SEQ ID NO: 325) consists of an in-line fusion having human ST2 (SEQ ID NO:328) at its N-terminus, followed by the extracellular region of human IL-1RAcP (SEQ ID NO:330), followed by a mouse IgG2a Fc (SEQ ID NO:333) at its C-terminus. The fourth IL33 antagonist (mST2-mIL1RAcP-mFc, SEQ ID NO: 326) consists of an in-line fusion having mouse ST2 (SEQ ID NO:329) at its N-terminus, followed by the extracellular region of mouse IL-1RAcP (SEQ ID NO:331), followed by a mouse IgG2a Fc (SEQ ID NO:333) at its C-terminus. The fifth IL33 antagonist (hST2-hIL1RAcP-hFc, SEQ ID NO:327) consists of an in line fusion having human ST2 of SEQ ID NO: 328 at its N-terminus, followed by the extracellular region of human IL-1RAcP (SEQ ID NO: 330) followed by a human IgG1 Fc (SEQ ID NO: 332) at its C terminus. See, Table 2.

four IL33 binding domains (D1, D2, D3 and D4,) are illustrated schematically in FIG. 1.

The individual components of the IL33 traps (e.g., D1, D2, M1, M2, etc.) may be attached to one another directly (e.g., D1 and/or D2 may be directly attached to M, etc.); alternatively, the individual components may be attached to one another via a linker component (e.g., D1 and/or D2 may be attached to M via a linker oriented between the individual components; D1 may be attached to D2 via a linker; etc.).

Polypeptides that bind IL33 and/or its receptor (ST2 and/or IL-1 RAcP) and block ligand-receptor interaction are

TABLE 2

| | | Summary of IL33 Antagonists and the Component Parts | | |
|---|---|---|---|---|
| IL33 Antagonist | Amino Acid Sequence of Full Antagonist Molecule | D1 Component | D2 Component | M Component |
| hST2-hFc | SEQ ID NO: 323 | human ST2 extracellular (SEQ ID NO: 328) | Absent | human IgG1 Fc (SEQ ID NO: 332) |
| hST2-mFc | SEQ ID NO: 324 | human ST2 extracellular (SEQ ID NO: 328) | Absent | mouse IgG2a Fc (SEQ ID NO: 333) |
| hST2-hIL1RAcP-mFc | SEQ ID NO: 325 | human ST2 extracellular (SEQ ID NO: 328) | human IL-1RAcP extracellular (SEQ ID NO: 330) | mouse IgG2a Fc (SEQ ID NO: 333) |
| mST2-mIL1RAcP-mFc | SEQ ID NO: 326 | mouse ST2 extracellular (SEQ ID NO: 329) | mouse IL-1RAcP extracellular (SEQ ID NO: 331) | mouse IgG2a Fc (SEQ ID NO: 333) |
| hST2-hIL1RAcP-hFc | SEQ ID NO: 327 | human ST2 extracellular (SEQ ID NO: 328) | human IL-1RAcP extracellular (SEQ ID NO: 330) | human IgG1 Fc (SEQ ID NO: 332) |

The IL33 traps may comprise at least one multimerizing domain (sometimes referred to herein by the abbreviation "M," "M1," "M2," etc.). In general terms, the multimerizing domain(s) function to connect the various components of the IL33 antagonists (e.g., the IL33-binding domain(s)) with one another. A multimerizing domain may comprise any macromolecule that has the ability to associate (covalently or non-covalently) with a second macromolecule of the same or similar structure or constitution. For example, a multimerizing domain may comprise a polypeptide comprising an immunoglobulin CH3 domain. A non-limiting example of a multimerizing domain is an Fc portion of an immunoglobulin, e.g., an Fc domain of an IgG selected from the isotypes IgG1, IgG2, IgG3, and IgG4, as well as any allotype within each isotype group.

Non-limiting exemplary multimerizing domains that can be used in the IL33 traps include human IgG1 Fc (SEQ ID NO: 332) or mouse IgG2a Fc (SEQ ID NO: 333). IL33 traps may comprise M components having an amino acid sequence that is at least about 80%, 85%, 90%, 91%, 92%, 93%, 94%, 95%, 96%, 97%, 98% or 99% identical to any of the exemplary M component amino acid sequences set forth herein (e.g., SEQ ID NOs: 332 or 333).

In some embodiments, the IL33 traps comprise two multimerizing domains, M1 and M2, wherein M1 and M2 are identical to one another. For example, M1 can be an Fc domain having a particular amino acid sequence, and M2 is an Fc domain with the same amino acid sequence as M1. The individual components of the IL33 antagonists (e.g., D1, D2, M, etc.) can be arranged relative to one another in a variety of ways. Non-limiting examples of all of the above noted arrangements, including an example of an IL33 trap comprising two multimerizing domains (M1 and M2) and considered as IL33 antagonists and are disclosed in PCT Publ. No. WO 2014/152195, which is incorporated by reference in its entirety. The biological characteristics of the IL33 traps are described in U.S. Publ. No. 2014/0271642, which is incorporated by reference herein in their entirety.

Other agents that may act as IL33 antagonists and which may be used in the methods include immunoadhesins, peptibodies, and soluble ST2, or derivatives thereof; anti-IL33 receptor antibodies (e.g., anti-ST2 antibodies, for example, AMG-282 (Amgen) or STLM15 (Janssen) or any of the anti-ST2 antibodies described in PCT Publ. Nos. WO 2012/113813, WO 2013/173761, and WO 2013/165894, as well as U.S. Pat. Nos. 8,444,987 and 7,452,980, which are each incorporated herein by reference in their entirety. Other IL33 antagonists include ST2-Fc proteins, such as those described in PCT Publ. Nos. WO 2013/173761 and WO 2013/165894, which are each incorporated herein by reference in their entirety.

In any of the methods described or exemplified herein, an IL-4R antagonist may be administered as part of a therapeutic regimen. The IL-4R antagonist is preferably administered in combination with the IL33 antagonist, though the IL-4R antagonist need not be administered at the same time as the IL33 antagonist. An IL-4R antagonist may comprise any agent that binds to or interacts with IL-4Rα or an IL-4R ligand, and inhibits or attenuates the normal biological signaling function of a type 1 and/or a type 2 IL-4 receptor. The IL-4R may comprise the amino acid sequence of SEQ ID NO: 347, or a biologically active fragment thereof. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists used in the methods may function by blocking IL-4-mediated signaling, IL-13-mediated signaling, or both IL-4- and IL-13-mediated signaling. The IL-4R antagonists may thus inhibit or prevent the interaction of IL-4 and/or IL-13 with a type 1 or type 2 receptor.

Non-limiting examples of categories of IL-4R antagonists include small molecule IL-4R antagonists, nucleic acid-based inhibitors of IL-4R expression or activity (e.g., siRNA or antisense), peptide-based molecules that specifically interact with IL-4R (e.g., peptibodies), "receptor-bodies" (e.g., engineered molecules comprising the ligand-binding domain of an IL-4R component), IL-4R-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, and anti-IL-4R aptamers or portions thereof.

In preferred embodiments, an IL-4R antagonist comprises an antibody that specifically binds to human IL-4R. Antibodies are typically referred to herein according to the following nomenclature: Fc prefix (e.g. "H1M," or "H4H"), followed by a numerical identifier (e.g., "9559," "9566," or "9629" as shown in Table 1), followed by a "P," or "N" suffix. According to this nomenclature, an antibody may be referred to herein as, e.g., "H1M9559N," "H1M9566N," "H4H9629P," etc. The H1M and H4H prefixes on the antibody designations used herein indicate the particular Fc region isotype of the antibody. For example, an "H1M" antibody has a mouse IgG1 Fc, whereas an "H4H" antibody has a human IgG4 Fc. An antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc In preferred embodiments, the anti-IL-4R antibody is dupilumab. See U.S. Pat. Nos. 7,605,237, 7,608,693, and 9,290,574, which are incorporated by reference.

Human anti-IL-4R antibodies can be generated as described in U.S. Pat. No. 7,608,693. One exemplary IL-4R antibody is a mouse antibody specific for mouse IL-4R, and has the following amino acid sequences: a heavy chain variable region (HCVR) comprising SEQ ID NO: 335 and a light chain variable domain (LCVR) comprising SEQ ID NO: 336. The human anti-IL-4R antibody, referred to as dupilumab, specifically binds to human IL-4Rα and comprises a heavy chain variable region (HCVR) comprising SEQ ID NO: 337 and a light chain variable region (LCVR) comprising SEQ ID NO: 338, a heavy chain complementarity determining region 1 (HCDR1) comprising SEQ ID NO: 339, a HCDR2 comprising SEQ ID NO: 340, a HCDR3 comprising SEQ ID NO: 341, a light chain complementarity determining region 1 (LCDR1) comprising SEQ ID NO: 342, a LCDR2 comprising SEQ ID NO: 343 and a LCDR3 comprising SEQ ID NO: 344. The full-length heavy chain of dupilumab is shown as SEQ ID NO: 345 and the full length light chain is shown as SEQ ID NO: 346.

In some embodiments, the IL-4R antagonist comprises an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. Nos. 7,605,237 and 7,608,693. In some embodiments, the IL-4R antagonist comprises an anti-IL-4R antibody having the binding characteristics of the reference antibody referred to herein as dupilumab (U.S. Pat. Nos. 7,605,237 and 7,608,693). In some embodiments, the anti-IL-4Rα antibody or antigen-binding fragment thereof comprises the heavy chain complementarity determining regions (HCDRs) of a heavy chain variable region (HCVR) comprising the amino acid sequence of SEQ ID NO: 337 and the light chain complementarity determining regions (LCDRs) of a light chain variable region (LCVR) comprising the amino acid sequence of SEQ ID NO: 338. In some embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 339; the HCDR2 comprises the amino acid sequence of SEQ ID NO: 340; the HCDR3 comprises the amino acid sequence of SEQ ID NO: 341; the LCDR1 comprises the amino acid sequence of SEQ ID NO: 342; the LCDR2 comprises the amino acid sequence of SEQ ID NO: 343; and the LCDR3 comprises the amino acid sequence of SEQ ID NO: 344. In yet other embodiments, the anti-IL-4R antibody or antigen-binding fragment thereof comprises an HCVR comprising SEQ ID NO: 337 and an LCVR comprising SEQ ID NO: 338. In yet other embodiments, the anti-IL-4R antibody or antigen-binding fragment thereof comprises an HCVR comprising SEQ ID NO: 335 and an LCVR comprising SEQ ID NO: 336. In some embodiments, the anti-IL-4R antibody or antigen-binding fragment thereof comprises a heavy chain (HC) amino acid sequence as set forth in SEQ ID NO: 345 and a light chain (LC) amino acid sequence as set forth in SEQ ID NO: 346.

In some embodiments, the IL-4R antibody or antigen-binding fragment thereof comprises the heavy chain complementarity determining regions (HCDRs) of a heavy chain variable region (HCVR) comprising the amino acid sequence of SEQ ID NO:335 or SEQ ID NO: 337 and the light chain complementarity determining regions (LCDRs) of a light chain variable region (LCVR) comprising the amino acid sequence of SEQ ID NO:336 or SEQ ID NO: 338.

In some embodiments, the IL-4R antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 339, the HCDR2 comprises the amino acid sequence of SEQ ID NO:340; the HCDR3 comprises the amino acid sequence of SEQ ID NO:341; the LCDR1 comprises the amino acid sequence of SEQ ID NO:342; the LCDR2 comprises the amino acid sequence of SEQ ID NO:343; and the LCDR3 comprises the amino acid sequence of SEQ ID NO:344.

In some embodiments, the IL-4R antibody or antigen-binding fragment thereof for use in the methods of the disclosure comprises an HCVR comprising the amino acid sequence of SEQ ID NO: 335 or SEQ ID NO: 337 and an LCVR comprising the amino acid sequence of SEQ ID NO: 336 or SEQ ID NO: 338.

In some embodiments, the IL-4R antibody or antigen-binding fragment thereof for use in the methods of the disclosure comprises an HCVR/LCVR amino acid sequence pair of SEQ ID NOs: 335/336 or SEQ ID NOs: 337/338.

Other anti-IL-4Rα antibodies include, for example, the antibody referred to and known in the art as AMG317 (Corren et al., 2010, Am J. Respir Crit Care Med., 181(8):

19                                                            20

788-796), or MEDI 9314, or any of the anti-IL-4Rα anti-bodies as set forth in any of U.S. Pat. Nos. 7,186,809, 7,605,237, 7,638,606, 8,092,804, 8,679,487, or 8,877,189.

The anti-IL-4Rα and the IL33 antibodies may have pH-dependent binding characteristics. For example, an anti-IL-4α antibody or an anti-IL33 antibody may exhibit reduced binding to IL-4Rα, or to IL33, respectively, at acidic pH as compared to neutral pH. Alternatively, an anti-IL-4Rα anti-body or an anti-IL33 antibody may exhibit enhanced binding to its antigen at acidic pH as compared to neutral pH. An "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. A "neutral pH" includes a pH of about 7.0 to about 7.4, as well as about 7.0, 7.05, 7.1, 7.15, 7.2, 7.25, 7.3, 7.35, and 7.4.

In another aspect, an IL33 antagonist is used alone or in combination with an IL-4R antagonist for treating or inhib-iting an inflammatory condition of the lungs. The IL33 antagonist or combination may be used for treating or inhibiting one or more of asthma, COPD, or ACOS. The IL33 antagonist or combination may be used for treating or inhibiting nasal polyps. The combination may be used for treating or inhibiting one or more of eosinophilic asthma, eosinophilic COPD, or eosinophilic ACOS. The IL33 antagonist or combination may be used for treating or inhibiting one or more of the high eosinophilic subset of eosinophilic asthma, eosinophilic COPD, or eosinophilic ACOS. The combination demonstrates enhanced efficacy, as compared to the treatment or inhibition obtained when each antibody is used alone as monotherapy.

In some embodiments, an IL33 antagonist or a combina-tion of an IL33 antagonist and an IL-4R antagonist is used in the manufacture of a medicament for the treatment or inhibition of any one of eosinophilic asthma, eosinophilic Chronic Obstructive Pulmonary Disease (COPD), eosino-philic asthma-Chronic Obstructive Pulmonary Disease over-lap syndrome (ACOS), high-eosinophil eosinophilic asthma, high-eosinophil eosinophilic COPD, high-eosinophil eosinophilic ACOS, or nasal polyps. In preferred embodi-ments, the IL33 antagonist or combination is used in the manufacture of a medicament for such treatment or inhibi-tion of any one of eosinophilic asthma, eosinophilic COPD, eosinophilic ACOS, high-eosinophil eosinophilic asthma, high-eosinophil eosinophilic COPD, high-eosinophil eosinophilic ACOS, or nasal polyps when a patient thereof has one or more risk alleles associated with eosinophilic asthma, eosinophilic COPD, or eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequi-librium thereof, or in both the intronic IL1RL1 variant rs1420101 (SEQ ID NO: 357) or variant in linkage disequi-librium thereof and the IL33 variant rs1342326 (SEQ ID NO: 358) or variant in linkage disequilibrium thereof.

According to such use, the IL33 antagonist may comprise an IL33 trap. The IL33 trap may comprise a first IL33 binding domain comprising an IL33 binding portion of IL1RL1 and a second IL33 binding domain comprising an extracellular portion of IL-1RAcP. The IL33 antagonist may alternatively comprise an antibody or antigen-binding frag-ment thereof that specifically binds to IL33. The antibody or antigen-binding fragment thereof that specifically binds to IL33 may comprise the H1, H2, and H3 domains of SEQ ID NO: 274 and the L1, L2, and L3 domains of SEQ ID NO: 282. The IL-4R antagonist may comprise an antibody or antigen-binding fragment thereof that specifically binds to IL-4R. The antibody or antigen-binding fragment thereof that specifically binds to IL-4R may comprise the H1, H2, and H3 domains of SEQ ID NO: 337 and the L1, L2, and L3 domains of SEQ ID NO: 338.

The following examples are provided to describe the disclosure in greater detail. They are intended to illustrate, not to limit, the disclosure.

EXAMPLE 1

Anti-IL33 Antibody, Anti-IL-4R Antibody, and a Combination of Both in a Chronic House Dust Mite-Induced Fibrosis and Severe Lung Inflammation Model Chronic inflammatory airway diseases are a consequence of recurrent episodes of airway inflammation predominantly due to repeated exposure to allergens or other pathogens. In humans, such chronic insults induce a vast array of patholo-gies that include pulmonary infiltration by immune cells, increased cytokine production, mucus production and col-lagen deposition. This increase in inflammatory cytokines and immune cell infiltrates, accompanied by intense airway remodeling leads to airway narrowing, hyperresponsiveness to inhaled triggers such as allergens or pathogens, airway obstruction and loss of lung function.

To determine the effect of anti-IL33 inhibition in a rel-evant in vivo model, a chronic house dust mite extract (HDM)-induced fibrosis and severe lung inflammation and remodeling study was conducted in mice that were homozy-gous for the expression of human IL33 in place of mouse IL33 (IL33 HumIn mice). See U.S. Publ. Nos. 2015/0320021 and 2015/0320022. Chronic HDM extract expo-sure induces severe lung inflammation, resulting in signifi-cant cellular infiltrate, cytokine expression, and remodeling. Efficacy of an anti-IL33 antibody, an anti-mouse IL-4Rα antibody or a combination of both was compared in this model. The anti-mouse IL-4Rα antibody used in this study is designated M1M1875N and comprises the HCVR/LCVR amino acid sequence pair of SEQ ID NOs: 335/336. The anti-IL33 antibody used in this study is designated H4H9675P and comprises the HCVR/LCVR amino acid sequence pair of SEQ ID NOs: 274/282.

IL33 HumIn mice were intranasally administered either 50 µg house dust mite extract (HDM; Greer, #XPB70D3A2.5) diluted in 20 µL of 1× phosphate buffered saline (PBS), or 20 µL of 1×PBS for 3 days per week for 15 weeks. A second control group of IL33 HumIn mice were administered 50 µg HDM extract diluted in 20 µL of 1×PBS for 3 days per week for 11 weeks, to assess the severity of the disease at the onset of antibody treatment. Four groups of HDM challenged mice were injected subcutaneously with 25 mg/kg of either the anti-IL33 antibody H4H9675P, the anti-mouse IL-4Rα antibody M1M1875N, a combination of both antibodies, or an isotype control antibody starting after 11 weeks of HDM challenge and then twice per week until the end of the HDM challenge (4 weeks of antibody treat-ment). On day 108 of the study, all mice were sacrificed and their lungs were harvested. Experimental dosing and treat-ment protocol for groups of mice are shown in Table 3.

TABLE 3

Experimental dosing and treatment protocol for groups of mice

| Group | Mice | Intranasal challenge | Length of intranasal challenge | Antibody |
|---|---|---|---|---|
| 1 | IL33 HumIn mice | 1X PBS | 15 weeks | None |
| 2 | IL33 HumIn mice | 50 µg HDM in 20 µL 1X PBS | 11 weeks | None |
| 3 | IL33 HumIn mice | 50 µg HDM in 20 µL 1X PBS | 15 weeks | None |
| 4 | IL33 HumIn mice | 50 µg HDM in 20 µL 1X PBS | 15 weeks | Isotype control antibody |
| 5 | IL33 HumIn mice | 50 µg HDM in 20 µL 1X PBS | 15 weeks | Anti-IL33 antibody (H4H9675P) |
| 6 | IL33 HumIn mice | 50 µg HDM in 20 µL 1X PBS | 15 weeks | Anti-IL-4Rα antibody (M1M1875N) |
| 7 | IL33 HumIn mice | 50 µg HDM in 20 µL 1X PBS | 15 weeks | Anti-IL33 (H4H9675P) antibody + Anti-IL-4Rα (M1M1875N) antibody |

Lung harvest for cytokine analysis. Elevated lung levels of key mediators such as the prototypic type 2 cytokines IL-4, IL-5, and IL-13, as well as cytokines more characteristic of type 1 immune responses, such as IL-1β or TNFα have been involved in human the development of lung diseases. Lung levels of these inflammatory cytokines were measured in the study.

After exsanguination, the cranial and middle lobes of the right lung from each mouse were removed and placed into tubes containing a solution of tissue protein extraction reagent (1×T-PER reagent; Pierce, #78510) supplemented with 1× Halt Protease inhibitor cocktail (Thermo Scientific, #87786). All further steps were performed on ice. The volume of T-PER Reagent (containing the protease inhibitor cocktail) was adjusted for each sample to match a 1:7 (w/v) tissue to T-PER ratio. Lung samples were mechanically disrupted using the TissueLyser II (Qiagen #85300). The resulting lysates were centrifuged to pellet debris. The supernatants containing the soluble protein extracts were transferred to fresh tubes and stored at 4° C. until further analysis.

Total protein content in the lung protein extracts was measured using a Bradford assay. For the assay, 10 µL of diluted extract samples were plated into 96 well plates in duplicates and mixed with 200 µL of 1× Dye Reagent (Biorad, #500-0006). Serial dilutions of bovine serum albumin (BSA; Sigma, #A7979), starting at 700 µg/mL in 1×T-Per reagent were used as a standard to determine the protein concentration of the extracts. After a 5-minute incubation at room temperature, absorbance at 595 nm was measured on a Molecular Devices SPECTRAMAX® M5 plate reader. Data analysis to determine total lung extract protein content based on the BSA standard was performed using GraphPad Prism™ software.

Cytokine concentrations in the lung protein extracts were measured using a Proinflammatory Panel 1 (mouse) multiplex immunoassay kit (MesoScale Discovery, # K15048G-2) and a custom mouse 6plex MULTI-SPOT® immunoassay kit (MesoScale Discovery, #K152A41-4), according to the manufacturer's instructions. Briefly, 50 µL/well of calibrators and samples (diluted in Diluent 41) were added to plates pre-coated with capture antibodies and incubated at room temperature while shaking at 700 rpm for 2 hours. The plates were then washed 3 times with 1×PBS containing 0.05% (w/v) TWEEN® -20 surfactant, followed by the addition of 25 µL of Detection Antibody Solution diluted in Diluent 45. After a 2 hour incubation at room temperature while shaking, the plate was washed 3 times, and 150 µL of 2× Read Buffer was added to each well. Electrochemiluminescence was immediately read on a MSD Spector instrument. Data analysis was performed using GraphPad Prism software.

Each cytokine concentration in lung total protein extracts from all mice in each group was normalized to the total protein content of the extracts measured by the Bradford assay, and expressed for each group as average pg of cytokine per mg of total lung proteins (pg/mg lung protein, ±SD) as shown in Table 4.

Lung cytokines analysis. As shown in Table 4, the level of the cytokines and chemokines IL-4, IL-5, IL-6, IL-1β and MCP-1 released in the lungs of IL33 HumIn mice receiving HDM for 15 weeks, with or without treatment with an isotype control antibody were significantly higher than in IL33 HumIn mice challenged with 1×PBS alone. Similarly, there was a trend towards an increased release of the cytokines IL-13 and TNFα in the lungs of IL33 HumIn mice receiving HDM for 15 weeks. In contrast, there was a significant reduction in the levels of IL-6, IL-13 and MCP-1 in the lungs of IL33 HumIn mice treated with a combination of anti-IL33 and anti-mouse IL-4Rα antibodies during the last four weeks of the chronic HDM challenge as compared to IL33 HumIn mice administered HDM with an isotype control antibody during this time period. There was a trend towards reduced IL-4, IL-5, IL-1β and TNFα lung levels in IL33 HumIn mice treated with a combination of anti-IL33 and anti-mouse IL-4Rα antibodies during the last four weeks of the chronic HDM challenge as compared to IL33 HumIn mice administered HDM with an isotype control antibody during this time period. The effects on lung cytokines observed with the combination anti-IL33 and anti-mouse IL-4Rα antibodies was greater than treatment with either individual antibodies alone.

TABLE 4

Cytokine concentration in lung protein extracts

| Experimental group | Mean [IL-4] in lung protein extracts (pg/mg lung protein) (±SD) | Mean [IL-5] in lung protein extracts (pg/mg lung protein) (±SD) | Mean [IL-13] in lung protein extracts (pg/mg lung protein) (±SD) | Mean [IL-6] in lung protein extracts (pg/mg lung protein) (±SD) | Mean [IL-1β] in lung protein extracts (pg/mg lung protein) (±SD) | Mean [TNFα] in lung protein extracts (pg/mg lung protein) (±SD) | Mean [MCP-1] in lung protein extracts (pg/mg lung protein) (±SD) |
|---|---|---|---|---|---|---|---|
| 1. 1X PBS challenge (n = 5) | 0.13 (±0.17) | 0.80 (±1.41) | ND | 4.75 (±3.39) | 1.97 (±1.67) | 2.86 (±1.01) | 4.12 (±1.12) |
| 2. HDM challenge 11 weeks (n = 4) | 5.71 (±3.76) * | 7.31 (±3.67) | 0.20 (±0.03) | 293.1 (±139.3) * | 181.8 (±131.0) * | 17.39 (±8.90) | 43.06 (±24.21) |

TABLE 4-continued

| | Cytokine concentration in lung protein extracts | | | | | | |
|---|---|---|---|---|---|---|---|
| Experimental group | Mean [IL-4] in lung protein extracts (pg/mg lung protein) (±SD) | Mean [IL-5] in lung protein extracts (pg/mg lung protein) (±SD) | Mean [IL-13] in lung protein extracts (pg/mg lung protein) (±SD) | Mean [IL-6] in lung protein extracts (pg/mg lung protein) (±SD) | Mean [IL-1β] in lung protein extracts (pg/mg lung protein) (±SD) | Mean [TNFα] in lung protein extracts (pg/mg lung protein) (±SD) | Mean [MCP-1] in lung protein extracts (pg/mg lung protein) (±SD) |
| 3. HDM challenge 15 weeks (n = 4) | 2.70 (±1.71) | 5.13 (±3.20) | 0.19 (±0.03) | 308.3 (±390.1) | 51.79 (±16.97) | 15.38 (±8.11) | 105.6 (±106.5) * |
| 4. HDM challenge 15 weeks + isotype control antibody (n = 4) | 5.46 (±3.38) ** | 7.00 (±4.50) * | 0.22 (±0.02) | 395.0 (±270.1) ** | 162.3 (±166.5) ** | 19.57 (±14.81) | 141.7 (±126.3) ** |
| 5. HDM challenge 15 weeks + anti-IL33 antibody (n = 5) | 1.15 (±1.38) | 1.93 (±1.90) | 0.20 (±0.02) | 136.8 (±164.1) | 122.9 (±194.1) | 17.05 (±4.48) * | 16.64 (±6.40) |
| 6. HDM challenge 15 weeks + anti-mouse IL-4Rα antibody (n = 5) | 2.88 (±2.43) | 13.13 (±12.81) ** | 0.16 (±0.03) | 18.24 (±12.43) | 26.73 (±20.94) | 7.85 (±4.89) | 11.63 (±8.69) |
| 7. HDM challenge 15 weeks + anti-IL33 + anti-mouse IL-4Rα antibodies (n = 5) | 0.47 (±0.13) | 0.73 (±0.37) | 0.10 (±0.05) †† | 7.46 (±2.52) † | 3.722 (±1.59) | 3.07 (±1.34) | 4.62 (±1.27) †† |

Note:
Statistical significance determined by Kruskal-Wallis One-way ANOVA with Dunn's multiple comparison post-hoc test is indicated
(* = $p < 0.05$,
** = $p < 0.01$, compared to groups 1: IL33 HumIn mice, Saline challenge;
† $p < 0.05$,
†† $p < 0.01$, compared to group 4: IL33 Humin mice, HDM challenge 15 weeks + Isotype control antibody).
ND: Not determined.

Lung harvest for gene expression analysis. After exsanguination, the accessory lobe of the right lung from each mouse was removed, placed into tubes containing 400 μL of RNA Later (Ambion, #AM7020) and stored at −20° C. until processing. Tissues were homogenized in TRIzol and chloroform was used for phase separation. The aqueous phase, containing total RNA, was purified using MagMAX™-96 for Microarrays Total RNA Isolation Kit (Ambion by Life Technologies, #AM1839) according to manufacturer's specifications. Genomic DNA was removed using Mag-MAX™Turbo™DNase Buffer and TURBO DNase from the MagMAX kit listed above. mRNA (up to 2.5 μg) was reverse-transcribed into cDNA using SuperScript® VILO™ Master Mix (Invitrogen by Life Technologies, #11755500). cDNA was diluted to 2 nd/μL and 10 ng cDNA was amplified with the TaqMan® Gene Expression Master Mix (Applied Biosystems by Life Technologies, #4369542) and the relevant probes (Life Technologies; mouse B2m: Mm00437762_m1; mouse Il4: Mm00445259_m1; mouse Il5: Mm00439646_m1; mouse Il13: Mm00434204_m1; mouse Il9: Mm00434305_m1; mouse Il6: Mm00446190_m1; mouse Ccl2: Mm00441242_m1; mouse Ccl11: Mm00441238_m1; mouse Ccl24: Mm00444701_m1; mouse Tnf: Mm00443258_m1; mouse Tgfb1: Mm01178820_m1; mouse Il1rl1: Mm00516117_m1; mouse Il13ra2: Mm00515166_m1; mouse Col15a1: Mm00456584_m1; mouse Col24a1: Mm01323744_m1;) using the ABI 7900HT Sequence Detection System (Applied Biosystems). B2m was used as the internal control genes to normalize any cDNA input differences. The reference group used for normalization of all samples was the average of Group 1 samples ('1×PBS Challenge'). Expression of each gene was normalized to B2m expression within the same sample and expressed relative to its normalized expression in the reference group (mean±SD), as shown in Table 5.

Lung gene expression analysis. As shown in Table 5, the level of expression of the cytokines, chemokines and collagen genes Il4, Il13, Il6, Ccl2, Tgfb1, Il13ra2 and Col24a1 in the lungs of IL33 HumIn mice receiving HDM for 15 weeks, with or without treatment with an isotype control antibody, were significantly increased compared to IL33 HumIn mice challenged with 1×PBS alone. Similarly, there was a trend towards an increase in expression of the genes Il5, Il9, Ccl11, Ccl24, Tnf, Il1rl1 and Col15a1 in the lungs of IL33 HumIn mice receiving HDM for 15 weeks.

In contrast, there was a significant reduction in the expression levels of Il6, Ccl2, Ccl11 and Ccl24 in the lungs of IL33 HumIn mice treated with a combination of anti-IL33 and anti-mouse IL-4Rα antibodies during the last four weeks of the chronic HDM challenge as compared to IL33 HumIn mice administered HDM with an isotype control antibody during this time period. There was a trend towards reduced Il4, Il5, Il13, Il9, Tnf, Tgfb1, Il1rl1, Il13ra2, Col15a1 and Col24a1 expression levels in mice treated with a combination of anti-IL33 and anti-mouse IL-4Rα antibodies during the last four weeks of the chronic HDM challenge as compared to IL33 HumIn mice administered HDM with an isotype control antibody during this time period. The effects on gene expression observed with the combination anti-IL33 and anti-mouse IL-4Rα antibodies was greater than treatment with either individual antibodies alone.

TABLE 5

| Experimental group | Mean Relative Il4 expression in lung (±SD) | Mean Relative Il5 expression in lung (±SD) | Mean Relative Il13 expression in lung (±SD) | Mean Relative Il9 expression in lung (±SD) | Mean Relative Il6 expression in lung (±SD) | Mean Relative Ccl2 expression in lung (±SD) | Mean Relative Ccl11 expression in lung (±SD) | Mean Relative Ccl24 expression in lung (±SD) |
|---|---|---|---|---|---|---|---|---|
| 1. 1X PBS challenge (n = 5) | 1.03 (±0.28) | 1.54 (±1.61) | 4.51 (±7.59) | 15.91 (±34.81) | 1.25 (±1.09) | 1.20 (±0.93) | 1.24 (±1.07) | 1.05 (±0.33) |
| 2. HDM challenge 11 weeks (n = 4) | 12.78 (±8.45) * | 7.13 (±3.49) | 114.1 (±68.3) * | 38.66 (±30.04) | 9.12 (±1.65) | 18.86 (±8.40) | 13.36 (±5.05) | 15.44 (±12.02) |
| 3. HDM challenge 15 weeks (n = 4) | 6.27 (±3.39) | 4.20 (±1.51) | 58.05 (±31.61) | 30.63 (±20.54) | 8.92 (±4.55) | 22.61 (±13.37) * | 8.65 (±3.20) | 4.58 (±1.91) |
| 4. HDM challenge 15 weeks + isotype control antibody (n = 4) | 10.98 (±5.46) * | 5.50 (±3.16) | 92.51 (±75.96) * | 19.51 (±10.29) | 13.80 (±6.98) ** | 24.53 (±9.13) ** | 12.14 (±7.82) | 12.41 (±8.73) |
| 5. HDM challenge 15 weeks + anti-IL33 antibody (n = 5) | 2.80 (±3.11) | 1.74 (±1.11) | 12.91 (±12.93) | 0.00 (±0.00) | 3.87 (±3.00) | 5.20 (±2.44) | 6.21 (±3.55) | 1.45 (±2.09) |
| 6. HDM challenge 15 weeks + anti-mouse IL-4Rα antibody (n = 5) | 1.87 (±1.03) | 7.98 (±6.52) | 69.56 (±66.86) * | 63.50 (±92.04) | 2.77 (±1.39) | 2.97 (±1.86) | 1.00 (±0.18) | 0.44 (±0.34) |
| 7. HDM challenge 15 weeks + anti-IL33 + anti-mouse IL-4Rα antibodies (n = 5) | 1.37 (±0.35) | 1.56 (±0.97) | 9.34 (±3.10) | 0.57 (±1.27) | 1.04 (±0.31) †† | 1.08 (±0.24) †† § | 0.72 (±0.28) † | 0.15 (±0.10) †† |

| Experimental group | Mean Relative Tnf expression in lung (±SD) | Mean Relative Tgfb1 expression in lung (±SD) | Mean Relative Il1rl1 expression in lung (±SD) | Mean Relative Il13rα2 expression in lung (±SD) | Mean Relative Col15α1 expression in lung (±SD) | Mean Relative Col24α1 expression in lung (±SD) |
|---|---|---|---|---|---|---|
| 1. 1X PBS challenge (n = 5) | 1.02 (±0.24) | 1.00 (±0.11) | 1.11 (±0.58) | 1.59 (±1.96) | 1.00 (±0.10) | 1.02 (±0.16) |
| 2. HDM challenge 11 weeks (n = 4) | 1.45 (±0.41) | 1.40 (±0.27) | 3.03 (±0.88) * | 48.43 (±34.21) | 2.75 (±0.96) | 24.55 (±7.97) ** |
| 3. HDM challenge 15 weeks (n = 4) | 1.58 (±0.43) | 1.32 (±0.33) | 2.53 (±0.79) * | 32.07 (±13.45) | 3.00 (±1.22) | 17.25 (±5.29) * |
| 4. HDM challenge 15 weeks + isotype control antibody (n = 4) | 1.59 (±0.78) | 1.37 (±0.12) * | 3.45 (±1.48) * | 52.02 (±40.63) | 3.80 (±0.96) * | 23.58 (±6.18) *** |
| 5. HDM challenge 15 weeks + anti-IL33 antibody (n = 5) | 1.38 (±0.27) | 1.22 (±0.24) | 0.99 (±0.47) | 13.54 (±12.25) | 1.64 (±0.30) | 10.58 (±5.42) |
| 6. HDM challenge 15 weeks + anti-mouse IL-4Rα antibody (n = 5) | 1.00 (±0.25) | 1.13 (±0.20) | 3.38 (±1.97) | 1.89 (±0.59) | 1.24 (±0.28) | 7.08 (±4.56) |
| 7. HDM challenge 15 weeks + anti-IL33 + anti-mouse IL-4Rα antibodies (n = 5) | 0.68 (±0.08) § | 1.09 (±0.12) | 1.12 (±0.57) | 1.89 (±0.27) | 0.74 (±0.21) †† § | 1.76 (±0.15) † |

Note:
Statistical significance determined by Kruskal-Wallis One-way ANOVA with Dunn's multiple comparison post-hoc test is indicated
(* = $p < 0.05$,
** = $p < 0.01$,
*** = $p < 0.01$ compared to groups 1: IL33 HumIn mice, Saline challenge;
§ $p < 0.05$,
§§ $p < 0.01$, compared to group 3: IL33 Humin mice, HDM challenge 15 weeks;
† $p < 0.05$,
†† $p < 0.01$, compared to group 4: IL33 Humin mice, HDM challenge 15 weeks + Isotype control antibody).

Lung harvest for pulmonary cell infiltrate analysis. Pulmonary infiltration by immune cells is observed in multiple airway inflammatory diseases, including asthma and COPD. Neutrophilic lung inflammation has been associated with lower lung function and severe tissue remodeling in asthma patients. Eosinophilic lung inflammation is a hallmark of type 2 inflammation usually seen in atopic diseases. In humans, high CD4/CD8 ratios are observed in patients with granulomatous lung diseases and other chronic inflammatory conditions. Flow cytometry was used in the study to determine the level of cellular infiltration in the lungs of HDM-exposed mice.

After exsanguination, the caudal lobe of the right lung from each mouse was removed, chopped into cubes that were approximately 2 to 3 mm in size, and then placed into a tube containing a solution of 20 μg/mL DNAse (Roche, #10104159001) and 0.7 U/mL Liberase TH (Roche, #05401151001) diluted in Hank's Balanced Salt Solution (HBSS) (Gibco, #14025), which was incubated in a 37' C. water bath for 20 minutes and vortexed every 5 minutes. The reaction was stopped by adding ethylenediaminetetraacetic acid (EDTA, Gibco, #15575) at a final concentration of 10 mM. Each lung was subsequently dissociated using a gen-tleMACS dissociator (Miltenyi Biotec, #130-095-937), then filtered through a 70 μm filter and centrifuged. The resulting lung pellet was resuspended in 1 mL of 1× red blood cell lysing buffer (Sigma, #R7757) to remove red blood cells. After incubation for 3 minutes at room temperature, 3 mL of 1×DMEM was added to deactivate the red blood cell lysing buffer. The cell suspensions were then centrifuged, and the resulting cell pellets were resuspended in 5 mL of MACS buffer (autoMACS Running Buffer; Miltenyi Biotec, #130-091-221). The resuspended samples were filtered through a 70 μm filter and $1 \times 10^6$ cells per well were plated in a 96-well V-bottom plate. Cells were then centrifuged and the pellets were washed in 1×PBS. After a second centrifugation, the cell pellets were resuspended in 100 μL of LIVE/DEAD Fixable Blue Dead Cell Stain (Life Technologies, #L23105) diluted at 1:500 in 1×PBS to determine cell viability and incubated for 20 minutes at room temperature while pro-tected from light. After one wash in 1×PBS, cells were incubated in a solution of MACS buffer containing 10 μg/mL of purified rat anti-mouse CD16/CD32 Fc Block, (Clone: 2.4G2; BD Biosciences, #553142) for 10 minutes at 4° C. The cells were then incubated in the appropriate 2× antibody mixture (described in Table 6) diluted in MACS buffer for 30 minutes at 4° C. while protected from light. After antibody incubation, the cells were washed twice in MACS buffer, resuspended in BD CytoFix (BD Biosciences, #554655) and then incubated for 15 minutes at 4° C. while protected from light. The cells were subsequently washed, resuspended in MACS buffer, and then transferred to BD FACS tubes (BD Biosciences, #352235) for analysis of cellular infiltrates by flow cytometry.

CD4 and CD8 T cells were defined as cells that were live, $CD45^+$, $SSC^{Lo}$, $FSC^{Lo}$, $CD3^+$, $CD19^-$, $CD4^+$, $CD8^-$ and live, $CD45^+$, $SSC^{Lo}$, $FSC^{Lo}$, $CD3^+$, $CD19^-$, $CD4^-$, $CD8^+$ respectively. Activated CD4 T cells were defined as cells that were live, $CD45^+$, $SSC^{Lo}$, $FSC^{Lo}$, $CD3^+$, $CD19^-$, $CD4^+$, $CD8^-$, and $CD69^+$. Activated CD8 T cells were defined as cells that were live, $CD45^+$, $SSC^{Lo}$, $FSC^{Lo}$, $CD3^+$, $CD19^-$, $CD4^-$, $CD8^+$, and $CD69^+$. Activated B cells were defined as cells that were live, $CD45^+$, $SSC^{Lo}$, $FSC^{Lo}$, $CD3^-$, $CD19^+$, and $CD69^+$. ST2+CD4+ T cells were defined as cells that were live, $CD45^+$, $SSC^{Lo}$, $FSC^{Lo}$, CD3+, CD19−, ST2+ and $CD4^+$. Eosinophils were defined as live, $CD45^+$, $GR1^-$, $CD11c^{lo}$, $SiglecF^{hi}$. Alveolar macrophages were defined as live, $CD45^+$, $GR1^-$, $CD11c^{Hi}$, $SiglecF^{hi}$. Data for activated cells is expressed as frequency of activated cells ($CD69^+$) within the parent population (CD4, ±SD). Data for ST2+

CD4+ T cells is expressed as frequency of T cells (defined as cells that were live, $CD45^+$, $SSC^{Lo}$, $FSC^{Lo}$, CD3+ and CD19−). Data for Eosinophils and Alveolar macrophages are expressed as frequency of live cells. CD4/CD8 T cells ratio is calculated as the ratio of the frequency of CD4 T to the frequency of CD8 T cells within the live population. All data are shown in Table 7.

TABLE 6

| Antibodies Used for Flow Cytometry Analysis | | | | |
|---|---|---|---|---|
| Antibody | Fluorochrome | Manufacturer | Catalogue Number | Final dilution |
| CD45.2 | PerCP-Cy5.5 | eBioscience | 45-0454 | 1/800 |
| Siglec-F | BV 421 | BD | 562681 | 1/200 |
| F4/80 | APC | eBioscience | 17-4801-82 | 1/200 |
| Ly6G | BUV395 | BD | 563978 | 1/200 |
| Ly6C | PE-Cy7 | BD | 560593 | 1/100 |
| CD11c | PE | eBioscience | 12-0114-82 | 1/200 |
| CD11b | FITC | eBioscience | 53-0112-82 | 1/200 |
| CD19 | BV650 | BD | 562701 | 1/400 |
| CD3 | PE-Cy7 | BD | 552774 | 1/200 |
| CD4 | BV421 | BioLegend | 100438 | 1/200 |
| CD8 | BUV 395 | BD | 563786 | 1/400 |
| NKp46 (CD335) | FITC | eBioscience | 11-3351 | 1/800 |
| CD69 | PE | eBioscience | 12-0691 | 1/200 |
| CD25 | BV510 | BioLegend | 102042 | 1/200 |
| ST2 | APC | BioLegend | 145306 | 1/200 |

Pulmonary cell infiltrate analysis. As shown in Table 7, the frequency of eosinophils, activated B cells, activated CD8 cells, ST2+Cd4+ T cells and CD4/CD8 T cells ratio in the lungs of IL33 HumIn mice receiving HDM for 15 weeks, with or without treatment with an isotype control antibody were significantly higher than in IL33 HumIn mice chal-lenged with 1×PBS alone. Similarly, there was a trend towards an increased frequency of activated CD4 T cells in the lungs of IL33 HumIn mice receiving HDM for 15 weeks. There was a trend towards a decreased frequency of alveolar macrophages detected by flow cytometry in the lungs of IL33 HumIn mice receiving HDM for 15 weeks, in the absence or presence of an isotype control antibody treat-ment. The frequency of alveolar macrophages was signifi-cantly increased in the lungs of IL33 HumIn mice treated with a combination of anti-IL33 and anti-mouse IL-4Rα antibodies during the last four weeks of the chronic HDM challenge as compared to IL33 HumIn mice administered HDM with an isotype control antibody during this time period. Similarly, there was a trend towards reduced fre-quency of eosinophils, activated CD4 and CD8 T cells, activated B cells, ST2+CD4+ T cells as well as CD4/CD8 T cells ratio in the lungs of mice treated with a combination of anti-IL33 and anti-mouse IL-4Rα antibodies during the last four weeks of the chronic HDM challenge as compared to IL33 HumIn mice administered HDM with an isotype control antibody during this time period. The effects on frequency of eosinophils, alveolar macrophages, activated CD8 T cells, ST2+CD4+ T cells and CD4/CD8 ratio in the lung observed for the combination anti-IL33 and anti-mouse IL-4Rα antibodies shows a trend towards greater efficacy than treatment with either individual antibodies alone.

TABLE 7

| | Mean Frequency of Eosinophils in the live population (±SD) | Mean Frequency of Alveolar Macrophages in the live population (±SD) | Mean CD4/CD8 T cells ratio (±SD) | Mean Frequency of Activated cells in CD4 T cells population (±SD) | Mean Frequency of Activated cells in CD8 T cells population (±SD) | Mean Frequency of Activated cells in B cells population (±SD) | Mean Frequency of ST2+ CD4+ cells in T cells population (±SD) |
|---|---|---|---|---|---|---|---|
| Experimental group | | | | | | | |
| 1. 1X PBS challenge (n = 5) | 1.45 (±0.92) | 5.05 (±1.64) | 3.00 (±1.48) | 13.12 (±9.89) | 3.26 (±1.64) | 0.39 (±1.17) | 3.25 (±4.15) |
| 2. HDM challenge 11 weeks (n = 4) | 17.08 (±3.94) * | 2.34 (±0.93) | 6.42 (±2.71) | 49.95 (±8.76) | 9.58 (±7.44) | 4.67 (±1.47) ** | 32.60 (±12.23) |
| 3. HDM challenge 15 weeks (n = 4) | 15.40 (±3.99) * | 4.92 (±1.55) | 6.95 (±0.71) ** | 58.53 (±5.76) | 15.68 (±3.03) * | 3.70 (±1.44) * | 37.33 (±8.98) * |
| 4. HDM challenge 15 weeks + isotype control antibody (n = 4) | 15.00 (±3.35) * | 2.33 (±1.60) | 7.49 (±1.28) * | 57.75 (±7.64) | 14.59 (±3.82) | 3.90 (±1.48) * | 37.96 (±16.71) * |
| 5. HDM challenge 15 weeks + anti-IL33 antibody (n = 5) | 8.51 (±7.52) | 7.44 (±4.18) | 4.03 (±1.28) | 48.22 (±5.66) | 13.86 (±5.21) | 1.72 (±0.72) | 19.24 (±5.72) |
| 6. HDM challenge 15 weeks + anti-mouse IL-4Rα antibody (n = 5) | 12.30 (±7.83) | 9.93 (±5.18) | 5.56 (±2.22) | 53.42 (±6.52) | 13.11 (±6.26) | 2.14 (±1.23) | 35.01 (±9.83) * |
| 7. HDM challenge 15 weeks + anti-IL33 + anti-mouse IL-4Rα antibodies (n = 5) | 3.78 (±1.60) | 14.64 (±3.86) † | 2.96 (±0.93) | 42.52 (±9.79) | 7.90 (±1.30) | 1.74 (±0.91) | 11.78 (±3.73) |

Note:
Statistical significance determined by Kruskal-Wallis One-way ANOVA with Dunn's multiple comparison post-hoc test is indicated
(* = $p < 0.05$,
** = $p < 0.01$, compared to groups 1: IL33 HumIn mice, Saline challenge;
† $p < 0.05$, compared to group 4: IL33 Humin mice, HDM challenge 15 weeks + Isotype control antibody).

Lung harvest for quantification of histopathology. The inflammatory pattern observed in this model is accompanied by widespread and severe structural changes in HDM-exposed lungs, with evidence of goblet cell metaplasia, increases in sub-epithelial collagen deposition and significant pulmonary consolidation. These pathologies are known features of human inflammatory respiratory diseases that contribute to decline of lung function and airway hyperreactivity.

After exsanguination, the left lungs were removed and placed into plates containing a 3 mL solution of 4% (w/v) paraformaldehyde (Boston Bioproducts, # BM-155) in 1× phosphate buffered saline and stored at room temperature for 3 days. Lung samples were then blotted dry and transferred to tubes containing 70% ethanol for histological analysis. The samples were sent to Histoserv, Inc (Germantown, MD) for paraffin embedding, sectioning and periodic acid Schiff (PAS) or Hematoxylin and Eosin (H&E) staining.

Quantification of Goblet cell metaplasia. Goblet cell metaplasia and mucus hyper-secretion are hallmarks of many pulmonary diseases including asthma, chronic obstructive pulmonary disease, and cystic fibrosis. Excessive mucus production leads to airway obstruction and affects several important outcomes such as lung function, health-related quality of life, exacerbations, hospitalizations, and mortality in humans. PAS-positive goblet cells and total epithelial cells were counted in a millimeter length of the primary bronchus. Goblet cell metaplasia is expressed as the frequency of PAS-positive cells in a millimeter of bronchial epithelium (%, ±SD) as shown in Table 8.

Quantification of lung consolidation. Lung consolidation includes the accumulation of solid or liquid material in the alveolar space. Lung consolidation is a compound endpoint likely reflecting the combination of cellular infiltrate, hyperplasia, and mucus production, used here as a measurement of gross pathology. The fraction of lung area occupied by the crystal bodies was quantified on Movat pentachrome stained paraffin-embedded lung sections using Image) software (NIH, Bethesda, MD). Using the particle analysis function, total lung area in the section, as well as consolidated area in the section were measured. The fraction of consolidated lung area is given by the ratio of both measurements, as shown in Table 8.

Quantification of sub-epithelial fibrosis. Sub-epithelial fibrosis includes an excess of interstitial collagen deposition beneath the pulmonary epithelium. Increased sub-epithelial fibrosis has been reported to be specifically associated with asthma in humans. In the model, sub-epithelial fibrosis was measured on Masson's trichrome stained paraffin-embedded lung sections using HaLo software (Indica Labs, NM). Using the Layer thickness tool, the thickness of the collagen layer beneath the bronchial epithelium was recorded multiple times, with about 30 µm intervals, across a millimeter of the primary bronchus. Sub-epithelial fibrosis is expressed as the mean thickness of the collagen layer beneath the epithelium (µm, ±SD) as shown in Table 8.

Analysis of lung histopathology. As shown in table 9, there was a trend towards an increase in goblet cell metaplasia in the lungs of IL33 HumIn mice receiving HDM for 15 weeks, with or without treatment with an isotype control antibody compared to IL33 HumIn mice challenged with 1×PBS alone. Similarly, there was a significant increase in lung consolidation, as well as in sub-epithelial collagen thickness, in IL33 HumIn mice receiving HDM for 15 weeks.

In contrast, there was trend towards a reduction in goblet cell metaplasia and sub-epithelial collagen thickness, and a significant reduction in lung consolidation in IL33 HumIn mice treated with a combination of anti-IL33 and anti-mouse IL-4Rα antibodies during the last four weeks of the chronic HDM challenge as compared to IL33 HumIn mice administered HDM with an isotype control antibody during this time period. The effects on goblet cell metaplasia, lung consolidation and sub-epithelial collagen thickness observed for the combination anti-IL33 and anti-mouse IL-4Rα antibodies showed a trend towards greater efficacy than treatment with either individual antibodies alone.

mean circulating HDM-specific IgG1 levels in serum for each experimental group are expressed as titer×10$^6$ (±SD) as shown in Table 9.

Analysis of the circulation levels of IgE and HDM-specific IgG1. As shown in Table 9, there was a significant increase in circulating levels of IgE in the serum of IL33 HumIn mice receiving HDM for 15 weeks, with or without treatment with an isotype control antibody in IL33 HumIn mice challenged with 1×PBS alone. Similarly, there was a trend towards an increased level of circulating HDM-specific IgG1 in the serum of IL33 HumIn mice receiving HDM for 15 weeks. In contrast, there was a significant decrease in

TABLE 8

Quantification of histopathology in mouse lungs

| Experimental group | Mean Goblet cell metaplasia (% PAS-positive cells) (±SD) | Mean lung consolidation (% ± SD) | Mean sub-epithelial collagen thickness (μm) (±SD) |
|---|---|---|---|
| 1. 1X PBS challenge (n = 5) | 32.94 (±43.61) | 6.97 (±3.72) | 25.90 (±4.00) |
| 2. HDM challenge 11 weeks (n = 4) | 59.98 (±39.01) | 70.70 (±12.94) | 81.76 (±25.37) * |
| 3. HDM challenge 15 weeks (n = 4) | 92.15 (±10.16) | 83.21 (±3.65) ** | 82.12 (±23.04) * |
| 4. HDM challenge 15 weeks + isotype control antibody (n = 4) | 81.60 (±17.56) | 84.16 (±5.85) ** | 63.11 (±11.87) |
| 5. HDM challenge 15 weeks + anti-IL33 antibody (n = 5) | 39.22 (±18.93) | 58.82 (±18.26) | 70.99 (±23.85) |
| 6. HDM challenge 15 weeks + anti-mouse IL-4Rα antibody (n = 5) | 79.82 (±25.02) | 57.79 (±18.72) | 57.62 (±15.34) |
| 7. HDM challenge 15 weeks + anti-IL33 + anti-mouse IL-4Rα antibodies (n = 5) | 19.69 (±8.80) | 35.01 (±20.68) | 48.19 (±18.58) |

Note:
Statistical significance determined by Kruskal-Wallis One-way ANOVA with Dunn's multiple comparison post-hoc test is indicated (** = p < 0.01, compared to groups 1: IL33 HumIn mice, Saline challenge).

Serum collection for IgE and HDM-specific IgG1 levels measurement. To determine the total IgE concentration in the serum samples for each mouse, a sandwich ELISA OPTEIA kit (BD Biosciences, #555248) was used according to the manufacturer's instructions. Serum samples were diluted and incubated with anti-IgE capture antibody coated on 96-well plates. Total IgE was detected by biotinylated anti-mouse IgE secondary antibody. Purified horseradish peroxidase (HRP)-labeled mouse IgE was used as a standard. The chromagen 3,3',5,5'-tetramethylbenzidine (TMB) (BD OPTEIA substrate reagent set, BD, #555214) was used to detect HRP activity. A stop solution of 1 M sulfuric acid was then added, and absorbance at 450 nm was measured on a Molecular Devices SpectraMax M5 plate reader. Data analysis was performed using Prism™ software. The mean amounts of circulating IgE levels in serum for each experimental group are expressed as ng/mL (±SD) as shown in Table 9.

To determine the HDM specific IgG1 levels in the serum samples from each mouse, an ELISA was utilized. HDM (Greer, #XPB70D3A2.5) coated plates were incubated with serially diluted mouse serum samples, followed by incubation with a rat anti-mouse IgG1-HRP conjugated antibody (BD Biosciences, #559626). All samples were developed with a TMB solution and analyzed as described above. Relative levels of circulating IgG1 in serum were represented as titer units (titer units were calculated by multiplying the measured OD by a dilution factor required to achieve OD450 that was greater than two times background). The circulating levels of IgE and a trend towards a decrease in circulating levels of HDM-specific IgG1 in the serum of IL33 HumIn mice treated with a combination of anti-IL33 and anti-mouse IL-4Rα antibodies during the last four weeks of the chronic HDM challenge as compared to IL33 HumIn mice administered HDM with an isotype control antibody.

TABLE 9

Circulating levels of IgE and HDM-specific IgG1 in mouse serum.

| Experimental group | Mean circulating IgE levels (μg/mL) (±SD) | Mean circulating HDM-specific IgG1 levels (Titer × 10$^6$) (±SD) |
|---|---|---|
| 1. 1X PBS challenge (n = 5) | 2.16 (±2.02) | ND |
| 2. HDM challenge 11 weeks (n = 4) | 50.16 (±8.35) | 1.18 (±0.15) |
| 3. HDM challenge 15 weeks (n = 4) | 131.38 (±106.84) * | 1.88 (±0.81) |
| 4. HDM challenge 15 weeks + isotype control antibody (n = 4) | 193.07 (±78.96) *** | 1.62 (±0.62) |
| 5. HDM challenge 15 weeks + anti-IL33 antibody (n = 5) | 45.74 (±45.74) | 1.76 (±0.98) |

TABLE 9-continued

Circulating levels of IgE and HDM-specific IgG1 in mouse serum.

| Experimental group | Mean circulating IgE levels (µg/mL) (±SD) | Mean circulating HDM-specific IgG1 levels (Titer × 10^6) (±SD) |
| --- | --- | --- |
| 6. HDM challenge 15 weeks + anti-mouse IL-4Rα antibody (n = 5) | 11.12 (±8.65) | 0.99 (±0.56) |
| 7. HDM challenge 15 weeks + anti-IL33 + anti-mouse IL-4Rα antibodies (n = 5) | 6.45 (±5.79) † | 0.75 (±0.30) |

Note:
Statistical significance determined by Kruskal-Wallis One-way ANOVA with Dunn's multiple comparison post-hoc test is indicated (* = p < 0.05,  = p < 0.01, * = p < 0.001, compared to groups 1: IL33 HumIn mice, Saline challenge; †p < 0.05, compared to group 4: IL33 Humin mice, HDM challenge 15 weeks + Isotype control antibody).
ND: Not determined.

A combination of H4H9675P and anti-mIL-4Rα treatment initiated in the context of severe, mixed inflammation improves all inflammatory parameters measured, reducing most to baseline levels. Additionally, additive effects are observed on some of the most pernicious endpoints, including composite lung gross pathology, goblet cell metaplasia, lung cellular infiltration, and cytokine levels. Therefore, blocking both pathways simultaneously has the potential to impact multiple inflammatory mediators in the context of severe mixed inflammation and tissue pathology, and normalize multiple parameters to baseline.

Example 2

Genetic Variants in IL33 and its Receptor Associate with Both Eosinophilic Asthma and COPD In this Example, the relationship between previously identified asthma risk variants at IL33 and IL1RL1 with risk of asthma, COPD, and ACOS was examined in the largest combined collection of such cases yet assembled, in which genetic data is linked to electronic health records. The importance of these variants to eosinophilic subtypes of asthma, COPD, and ACOS, as well as to related upper airway diseases such as nasal polyps was examined. In addition, the association between predicted loss-of-function variants (pLOF) in IL1RL1 and IL33 with these diseases was evaluated.

Human Genetics Study Oversight. The human genetics studies were conducted as part of the DiscovEHR study of the Regeneron Genetics Center (RGC) and the Geisinger Health System (GHS).

DiscovEHR Participants and Disease Definitions. At the time of this study, the DiscovEHR study comprised a total of 92,323 adult individuals enrolled in the MyCode® Community Health Initiative of the GHS. For this study 86,004 and 83,339 individuals of European ancestry had phenotype, and exome sequencing and genotype data, respectively for analysis. Participants were recruited from outpatient primary care and specialty clinics. Eosinophil counts and disease diagnosis codes (the International Classification of Diseases, Ninth Revision [ICD-9]) were extracted from EHRs, which covered a median of 14 years of clinical care. Median EHR-documented eosinophil count measurements were derived from complete blood counts following removal of likely spurious values that were >3 standard deviations from the intra-individual median value. Case status was assigned on the basis of ICD-9 codes if at least one of the following criteria were met: (1) a problem-list entry of the diagnosis code; or (2) an encounter diagnosis code entered for 2 separate clinical encounters on separate calendar days. Individuals were assigned one or more of the three case classifications (asthma, COPD and ACOS) based on ICD-9 diagnosis codes.

Control patients for all binary trait analyses were defined as individuals without a single ICD-9 diagnosis code of asthma or COPD.

Sequencing and Genotyping. Sample preparation and whole exome sequencing were performed. In brief, exome capture was performed using either NimbleGen probes (Roche, SeqCap VCRome) or Integrated DNA Technologies probes (IDT, xGEN Exome Research panel) with additional content according the respective manufacturer's recommended protocol. Captured DNA was PCR amplified and quantified by qRT-PCR (Kapa Biosystems). Multiplexed samples were sequenced using 75 bp paired-end sequencing on Illumina v4 HiSeq 2500 or HiSeq X sequencers to a coverage depth sufficient to provide greater than 20× haploid read depth of over 85% of targeted bases in 96% of samples (approximately 80× mean haploid read depth of targeted bases). Raw sequence data from each Illumina HiSeq 2500 run were uploaded to the DNAnexus platform for sequence read alignment and variant identification. Raw sequence data were converted from BCL files to sample-specific FASTQ-files, which were aligned to the human reference build GRCh38 with BWA-mem. Single nucleotide variants (SNV) and insertion/deletion (indel) sequence variants were identified using the Genome Analysis Toolkit. Samples with genotype rate less than 10% were excluded. For final analyses, exome data was available for 59,082 and 29,504 individuals of European Ancestry captured using VCRome xGEN probe sets, respectively.

Aliquots of DNA were genotyped using the Human OmniExpress Exome Beadchip or the Global Screening Array (Illumina Corp.). For final analyses, Chip data was available for 56,239 and 28,500 individuals of European ancestry assayed on the Omni and GSA BeadChips respectively Study Design and Statistical Analysis. OMNI and GSA Chip data was used to evaluate two previously identified asthma risk variants (IL33 (rs1342326) and IL1RL1 (rs1420101)) for association with obstructive lung diseases, other airway diseases, and circulating eosinophil counts. These variants were tested for association with disease under an additive model using logistic regression in PLINK or R, including age, age², sex, smoking status, and the first four principal components of ancestry as covariates. Median EHR-documented eosinophil counts were log-transformed and tested for association with genotypes under an additive genetic model using linear (PLINK, R) models controlling for the same covariates as above. All p-values correspond to additive genetic models. Resulting summary statistics from analyses on both platforms were combined by meta-analysis.

Under the same statistical framework, exome data was used to identify associations between pLOF variants aggregated within IL1RL1 or IL33 and obstructive lung disease outcomes and eosinophil counts. At each gene, individuals were coded 0 if they did not carry any pLOF, and 1 if they were heterozygous carriers of at least one pLOF; No homozygous pLOF carriers for either IL1RL1 or IL33 were observed in this study. Resulting summary statistics from analyses on both platforms were combined by meta-analysis.

A genetic risk score, reflecting the sum of risk alleles for two independent variants (IL33 (rs1342326) and IL1RL1 (rs1420101)), was also used as a predictor of obstructive lung disease outcomes and eosinophil counts using logistic and linear regression models and the same covariates described above. Individuals missing genotype data for either or both variants were excluded. The effects of carrying one, two, three, or four risk alleles were determined separately relative to individuals carrying no risk allele at either variant. Trends between increasing score and increasing eosinophil counts or disease risk were tested using the linear regression and the Cochran-Armitage test, respectively.

All statistical analyses were performed with the use of PLINK software (v1.90p) or R version 3.2.1.

Confirmation of previously identified asthma risk variants in IL33 and IL1RL1 with DiscovEHR eosinophil counts and EHR-defined asthma. Clinical characteristics of MyCode® participants in the DiscovEHR study are described in FIG. 8. Among 86,004 patients of European ancestry exome sequenced in this study, 13267 (15.4%) patients were diagnosed with asthma, 9783 (11.4%) patients with COPD, and 2993 (3.4%) patients with both asthma and COPD (referred to here as asthma-COPD overlap syndrome, or ACOS). Among 83,339 patients of European ancestry with available Chip data for this study, 12832 (15.4%) patients were diagnosed with asthma, 9536 (11.4%) patients with COPD, and 2909 (3.5%) patients with ACOS.

Figure 3:
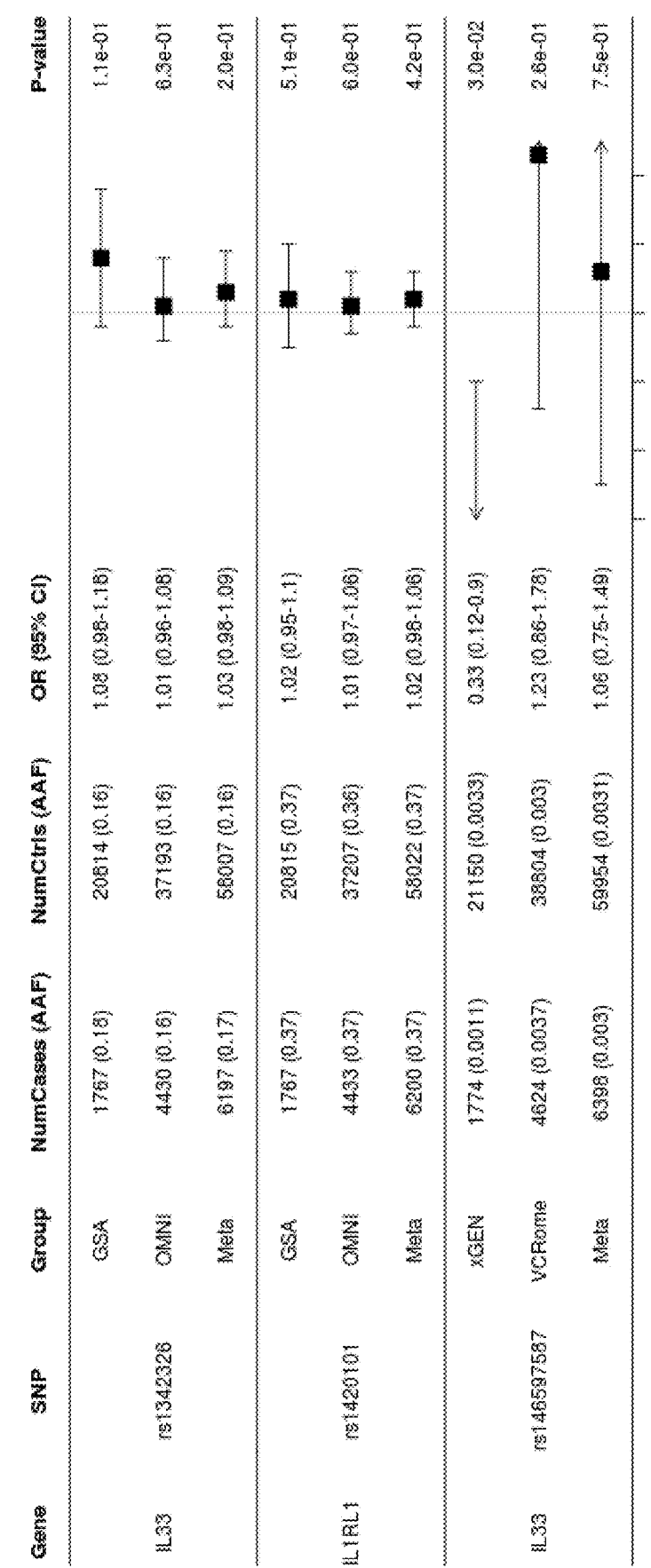
FIG. 3 (Panels A, B, and C) shows rs1420101 (IL1RL1, also known as ST2), s1342326 (IL33) and rs146597587 (IL33-pLoF) associations with (Panel A) Asthma, (Panel B) High Eosinophil Asthma Subset and (Panel C) Low Eosinophil Asthma Subset. Odds ratios for disease were calculated using logistic regression, with adjustment for age, $age^2$, sex, smoking status and principal components of ancestry.

The first large GWAS of asthma identified an intronic IL1RL1 variant (rs1420101) that was associated with both asthma and circulating eosinophil counts, and a subsequent GWAS identified an upstream IL33 variant (rs1342326) that was associated with asthma. In this study, association of rs1420101 (IL1RL1) and rs1342326 (IL33) with asthma (meta allelic odds ratio ($OR_{allelic}$) was confirmed (95% confidence interval) 1.07 (1.04-1.11), P=$8.2\times10^{-7}$ and Meta-$OR_{allelic}$ 1.09 (1.05-1.16), P=$6.0\times10^{-6}$, respectively) (FIG. 3).

Additionally, both variants were associated with lifetime median circulating eosinophil counts (n=66,776 individuals) (Meta-beta=0.0066 (0.0054-0.0079) eos/ml, P=$2.0\times10^{-23}$ and Meta-beta=0.0061 (0.0045-0.0078) eos/ml, P=$2.0\times10^{-13}$, respectively IL33 and IL1RL1 associations with asthma are specific to eosinophilic subset. Eosinophilic asthma is recognized as an important subset of asthma, and seems to be associated with increased asthma severity and steroid refractoriness, as well as differential responsiveness to biologic therapies. Having confirmed the previously described associations between the IL33 and IL1RL1 variants and eosinophil counts as well as asthma, independently assessed as distinct phenotypes, the study next assessed whether these risks are connected through a specific association with the eosinophilic subset of asthma, and therefore associations in asthma patient subgroups stratified by high (>200 eos/µL) and low (≤200 eos/µL) median lifetime eosinophil counts were assessed (FIG. 3). Both the IL33 (rs1342326) and IL1RL1 (rs1420101) variants were significantly associated only with the eosinophilic asthma subset (for IL33, the allelic meta odds ratio was 1.12 (1.06-1.18) in the high eosinophil group vs. 1.04 (0.98-1.09) in the low eosinophil group; for IL1RL1, the allelic odds ratio was 1.07 (1.04-1.1) in the high eosinophil group vs. 1.02 (0.98-1.06) in the low eosinophil group) (FIG. 3).

Novel associations between asthma risk variants in IL33 and IL1RL1 and increased risk of COPD and ACOS, specifically in eosinophilic subsets. In addition to the above associations with eosinophilic asthma, it was further discovered that the IL33 (rs1342326) and IL1RL1 (rs1420101) variants are suggestively or marginally significantly associated with COPD (FIG. 4, for IL33, Meta $OR_{allelic}$=1.04 (0.99-1.09), P=$8.9\times10^{-2}$, and for IL1RL1, Meta-$OR_{allelic}$=1.04 (1-1.07), P=$3.9\times10^{-2}$) and ACOS (FIG. 5 for IL33, Meta $OR_{allelic}$ 1.08 (1.0-1.16), P=$3.8\times10^{-2}$, and for IL1RL1, 1.06 (1.0-1.12), P=$4.8\times10^{-2}$).

Figure 4:
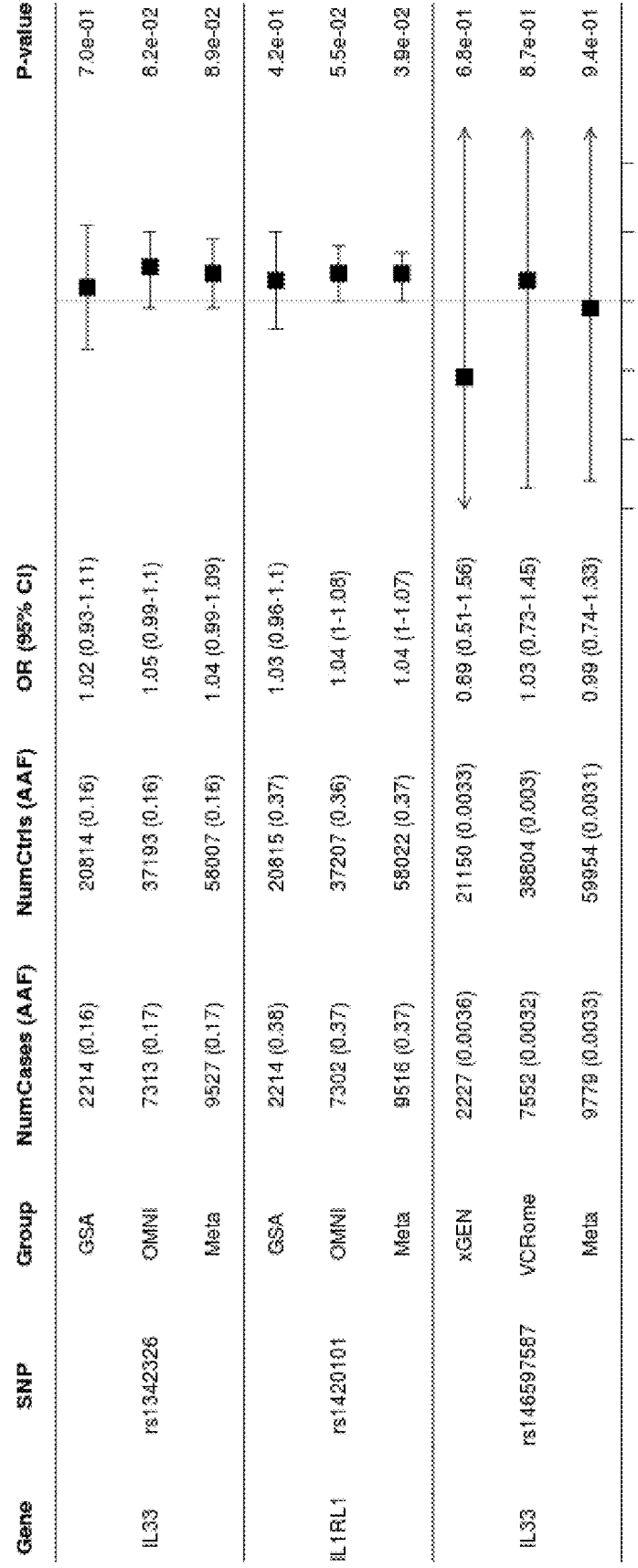
FIG. 4 (Panels A, B, and C) shows rs1420101 (IL1RL1, also known as ST2), s1342326 (IL33) and rs146597587 (IL33-pLoF) associations with (Panel A) COPD, (Panel B) High Eosinophil COPD Subset and (Panel C) Low Eosinophil COPD Subset. Odds ratios for disease were calculated using logistic regression, with adjustment for age, $age^2$, sex, smoking status and principal components of ancestry.
Figure 4:
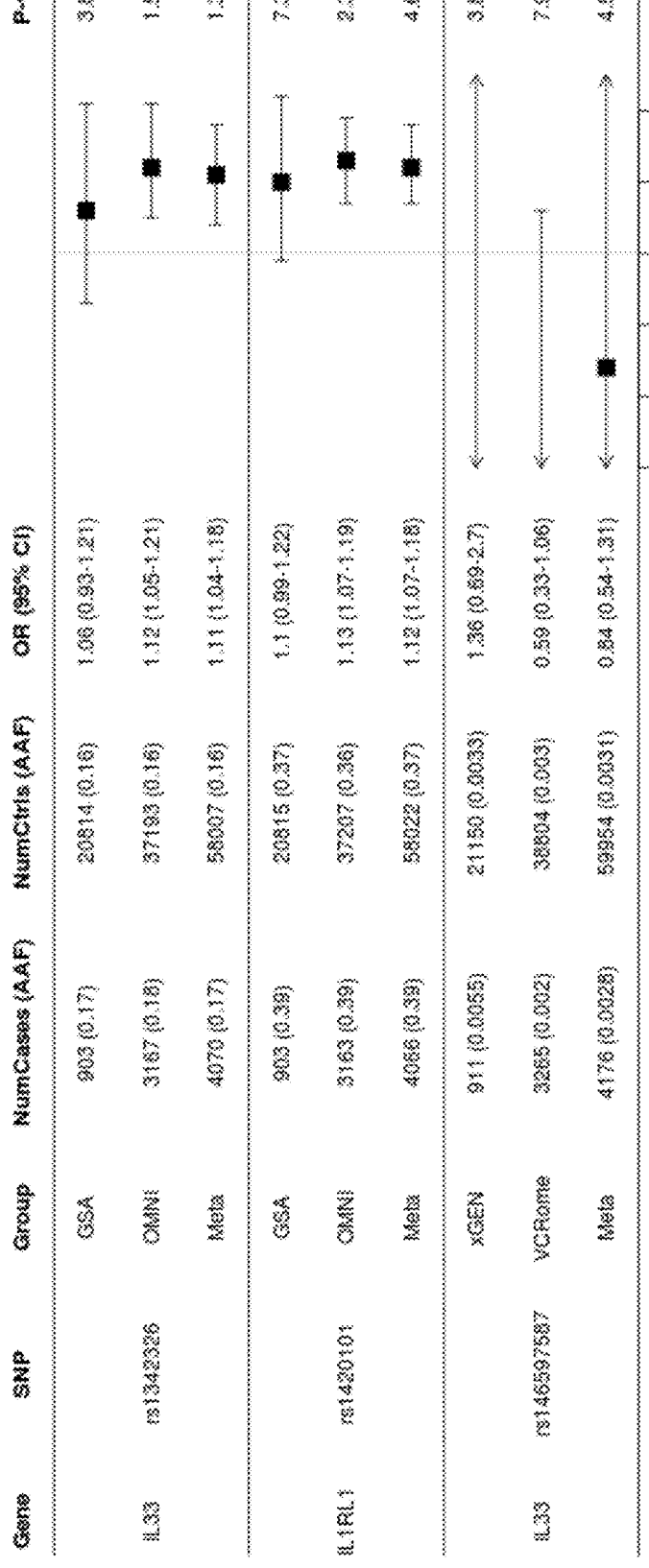
Figure 4:
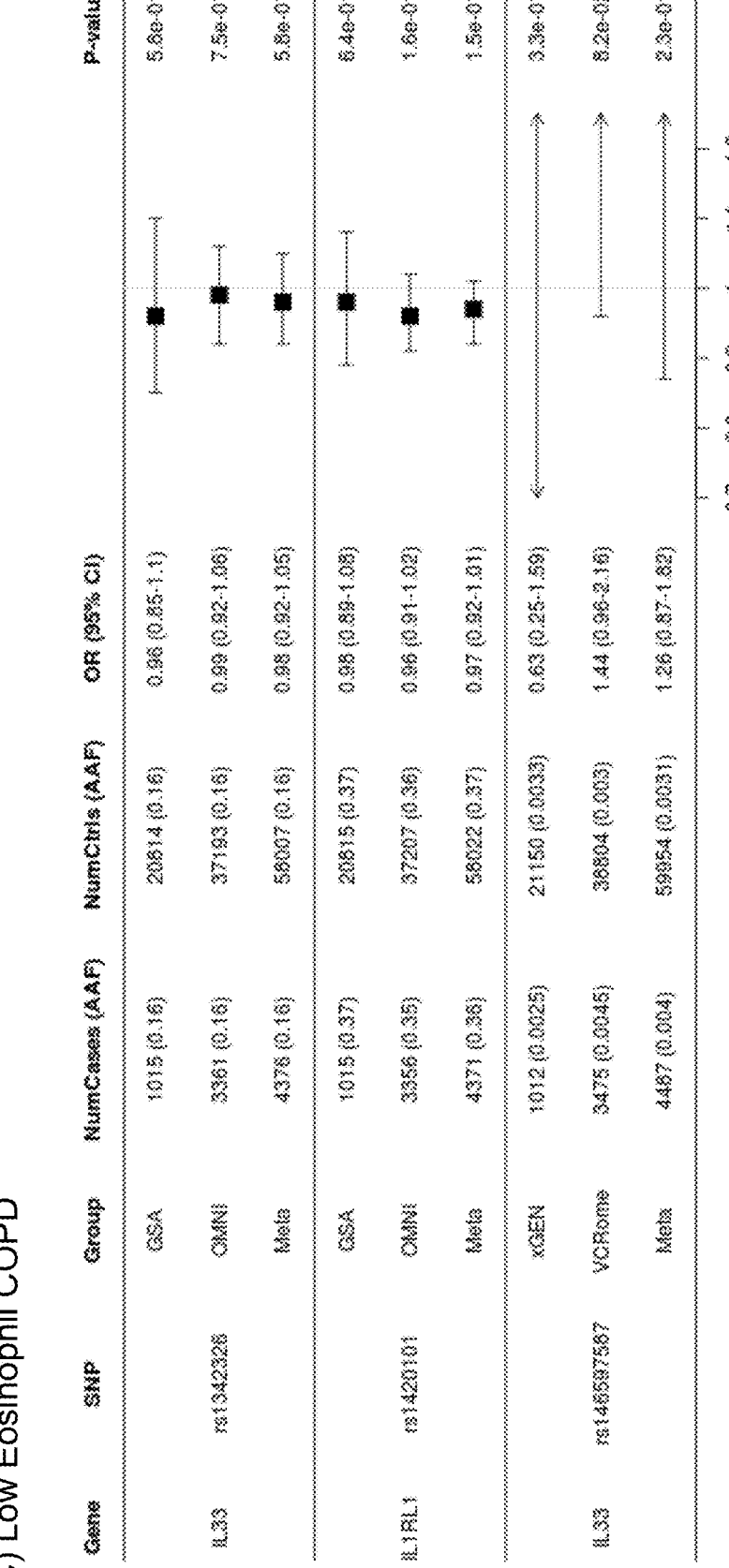
Figure 5:
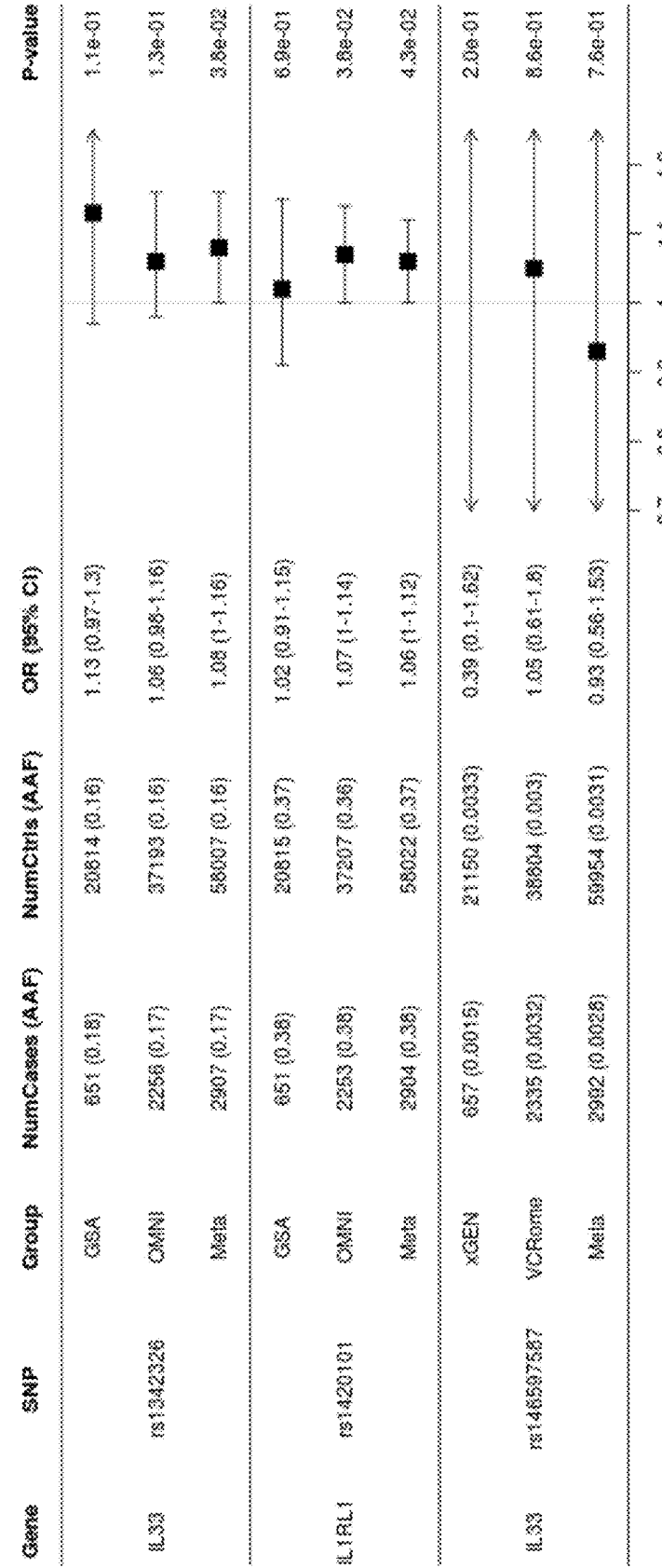
FIG. 5 (Panels A, B, and C) shows rs1420101 (IL1RL1, also known as ST2), s1342326 (IL33) and rs146597587 (IL33-pLoF) associations with (Panel A) ACOS, (Panel B) High Eosinophil ACOS Subset and (Panel C) Low Eosinophil ACOS Subset. Odds ratios for disease were calculated using logistic regression, with adjustment for age, $age^2$, sex, smoking status and principal components of ancestry.
Figure 5:
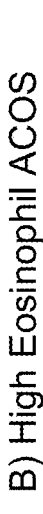

As with asthma, eosinophilic subsets of COPD and ACOS are associated with more severe disease. To determine whether the IL33 and IL1RL1 associations with COPD and ACOS were also specific to eosinophilic subtypes, as we had seen in asthma, associations between IL33 (rs1342326) and IL1RL1 (rs1420101) in COPD and ACOS subgroups stratified by high (>200 eos/µL) and low (≤200 eos/µL) median lifetime eosinophil count were assessed (FIGS. 4 and 5). Both variants were suggestively associated with COPD and ACOS only in the disease subgroups characterized by high circulating eosinophils.

Figure 2:
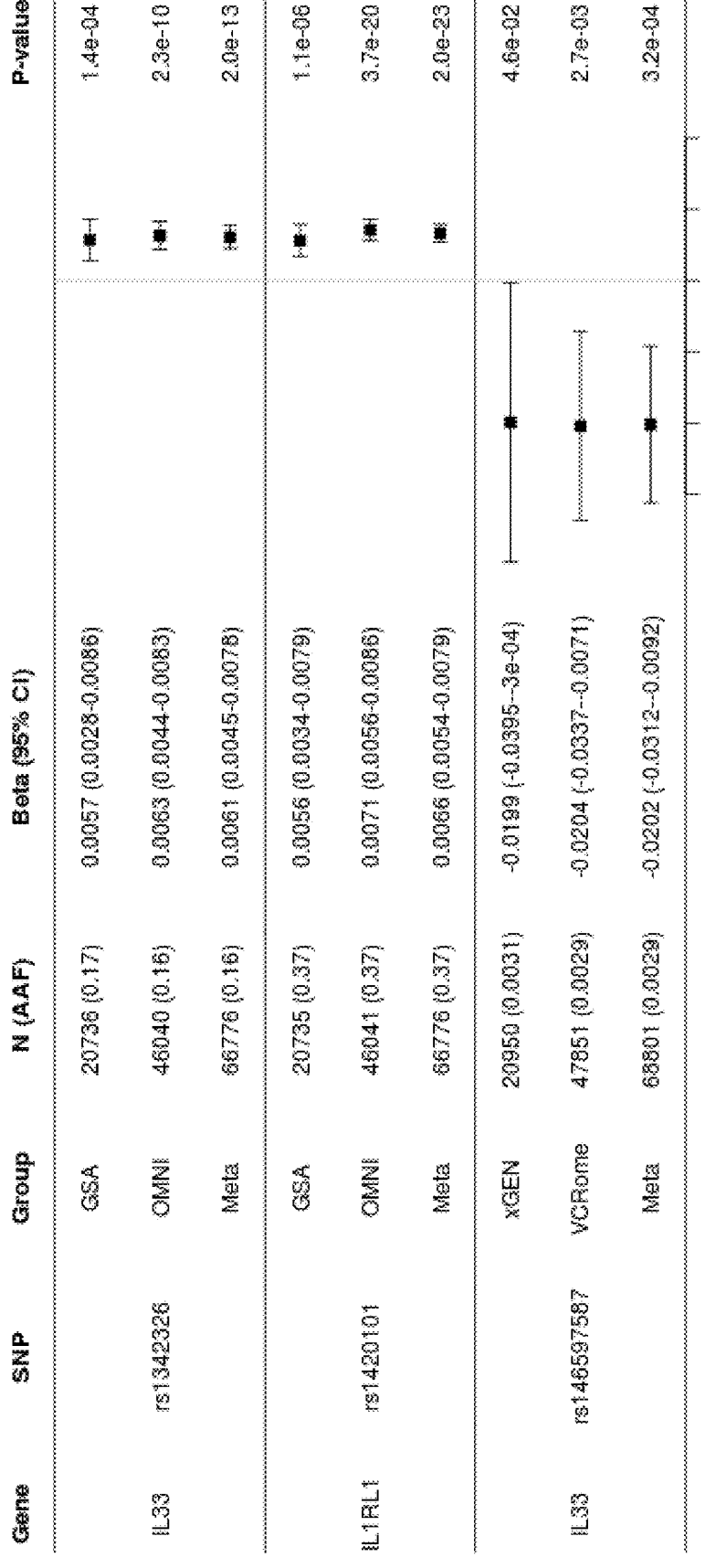
FIG. 2 (Panels A, B, C, and D) shows rs1420101 (IL1RL1, also known as ST2), s1342326 (IL33) and rs146597587 (IL33-pLoF) associations with (Panel A) eosinophil counts (Panel B) login eosinophil counts. The associations between the total burden of rs1420101 and rs1342326 risk alleles, and (Panel C) eosinophil counts (Panel D) $\log_{10}$ eosinophil counts is also shown. Effect sizes and P-values for eosinophil counts and $\log_{10}$ eosinophil counts, were calculated using linear regression, with adjustment for age, $age^2$, sex, smoking status and principal components of ancestry. P-values and effect sizes/odds ratios were estimated for individual scores; in each case the comparison was to individuals with zero risk alleles. Additionally, overall allelic effects p-values are shown.
Figure 2:
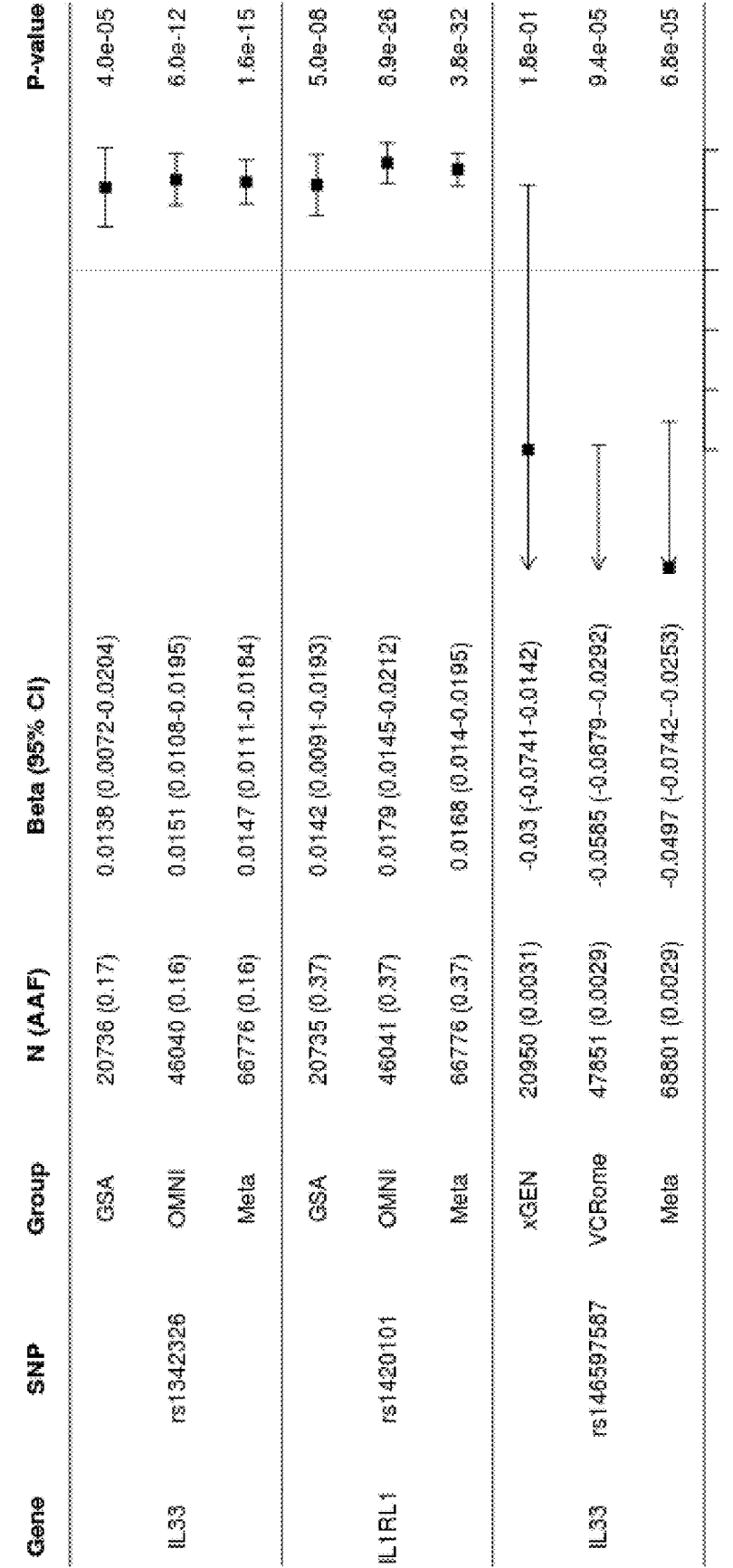
Figure 2:
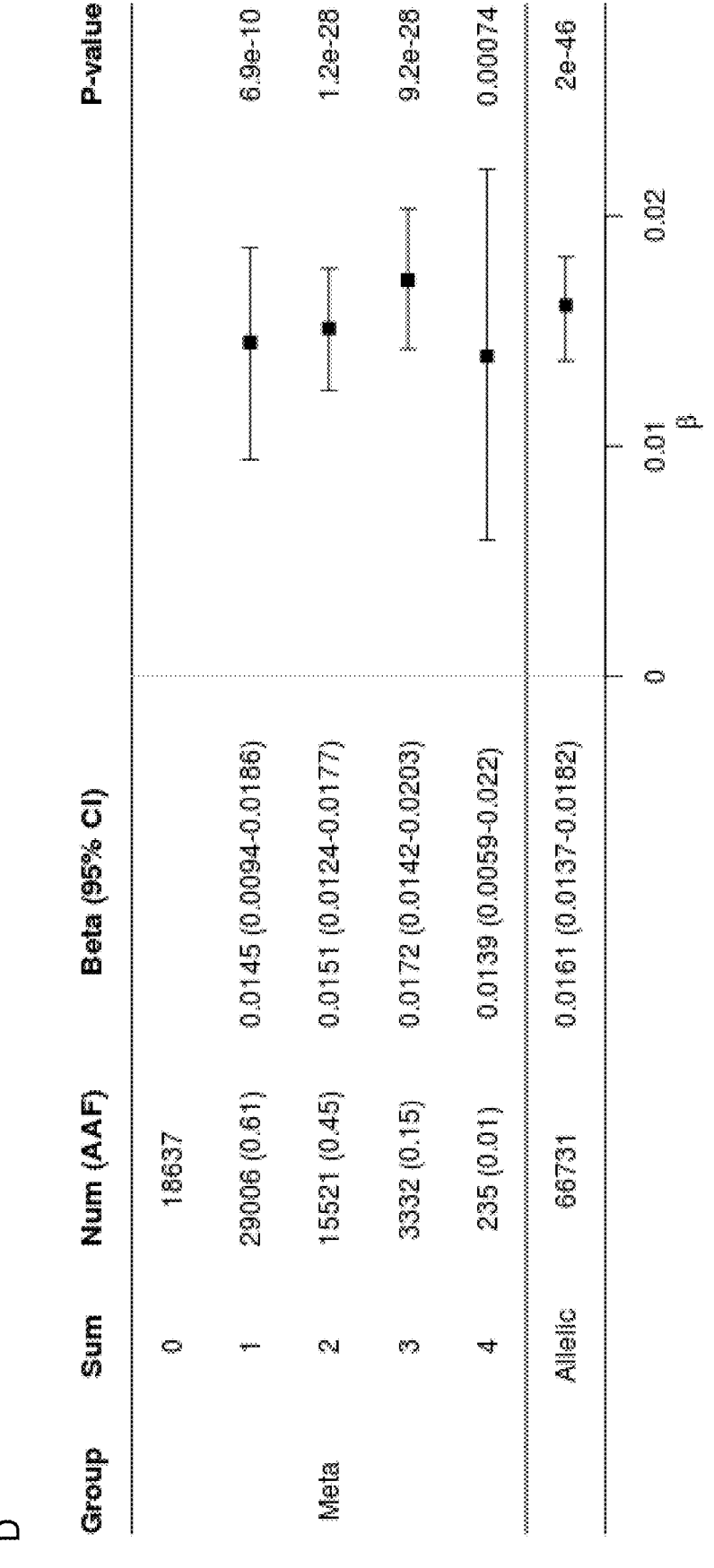
Figure 6:
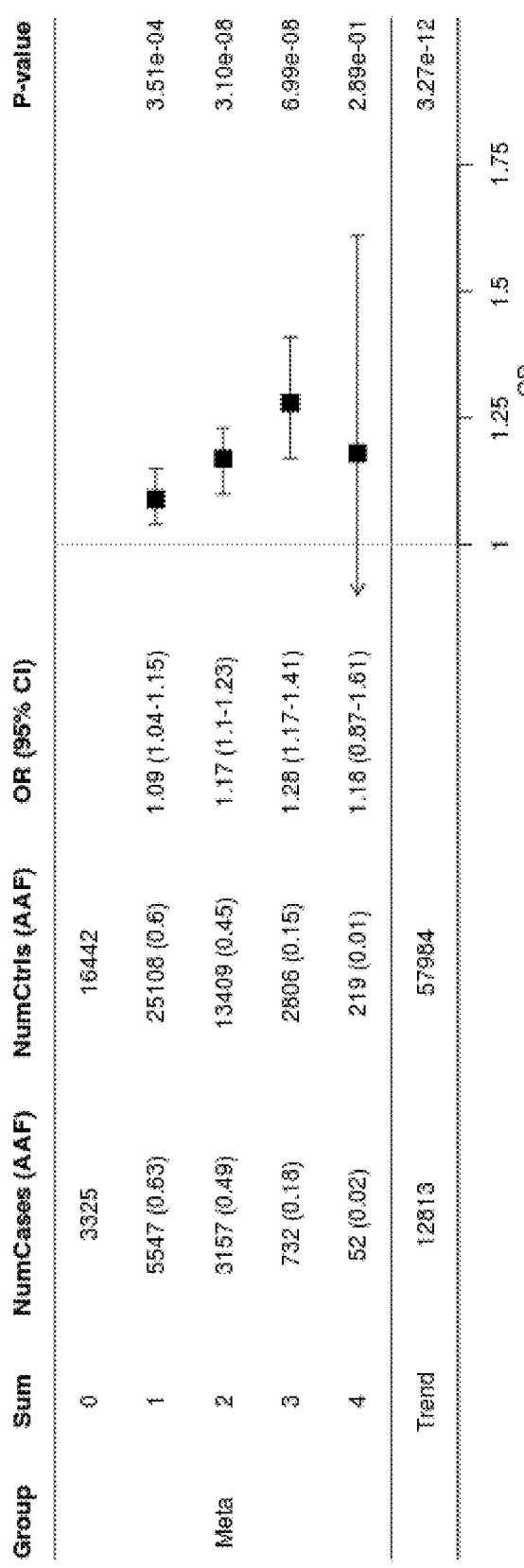
FIG. 6 (Panels A, B, and C) shows genetic score (total burden of rs1420101 and rs1342326 risk alleles) associations with (Panel A) Asthma (Panel B) COPD and (Panel C) ACOS. P-values odds ratios were estimated for individual scores; in each case the comparison was to individuals with zero risk alleles. Additionally, overall trend test p-values are shown.
Figure 6:
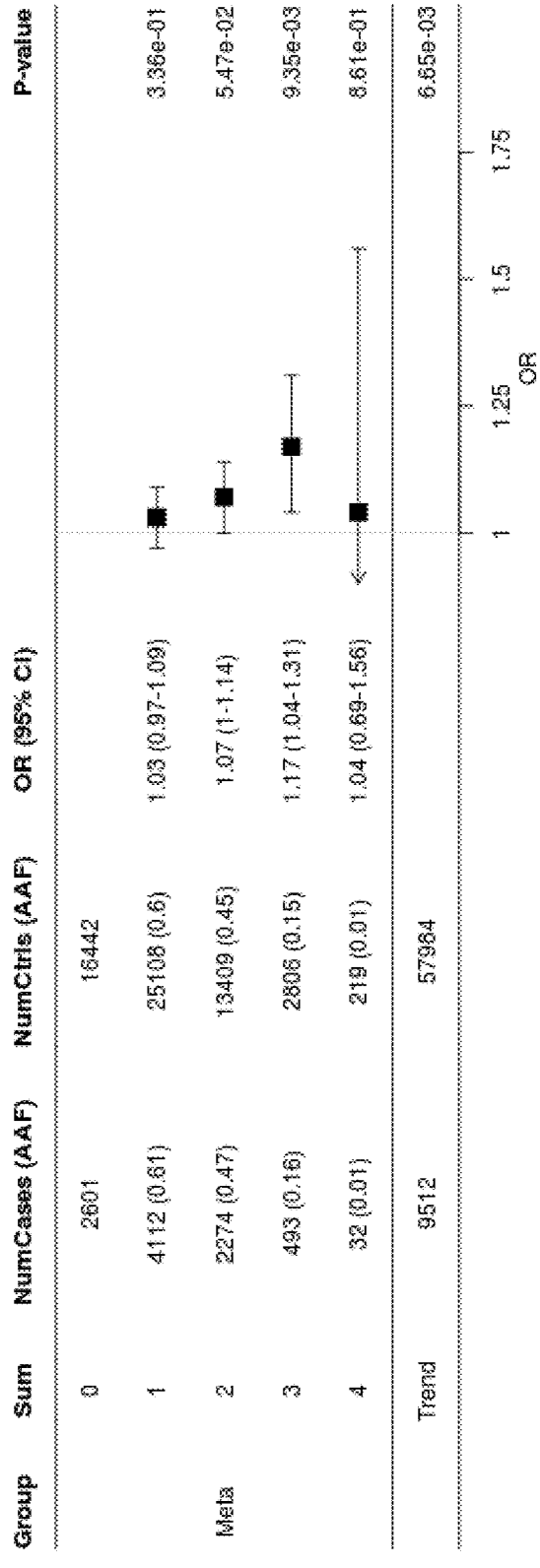
Figure 6:
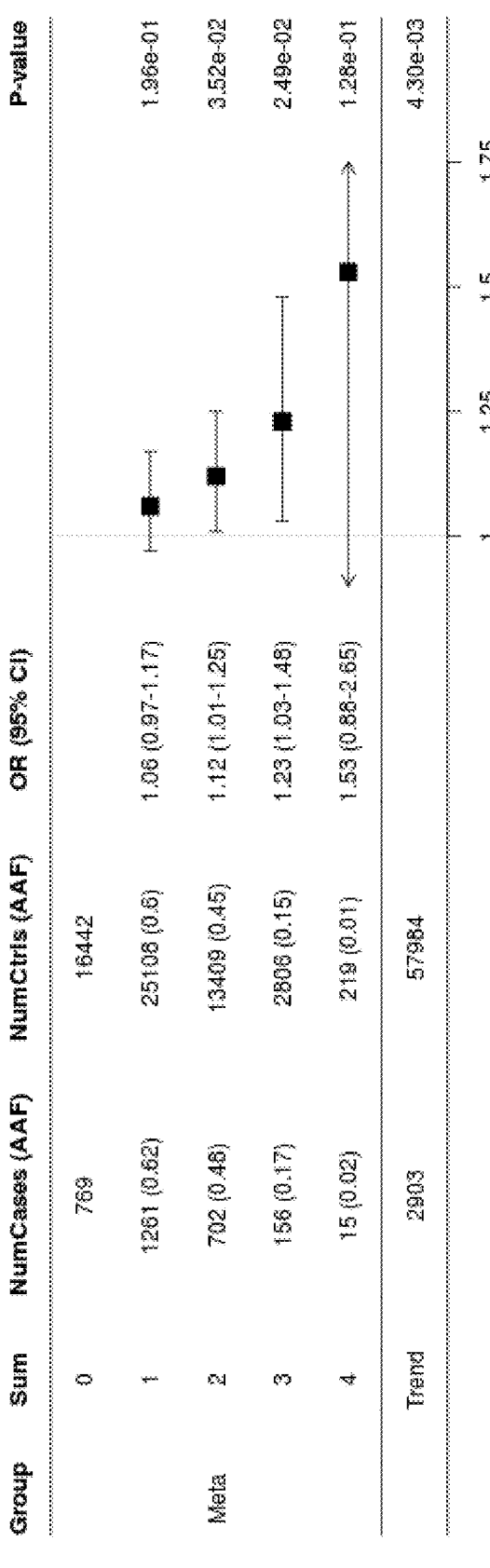

Higher burden of risk-increasing alleles in the IL33 signaling pathway leads to larger increases in asthma, COPD and ACOS risk. Since IL33 and IL1RL1 are part of the same signaling complex, and since these variants display notable allele-dosage dependence in their risk associations when analyzed individually, a two-variant genetic risk score was constructed by summing the number of risk alleles at IL33 (rs1342326) and IL1RL1 (rs1420101) (each individual had a score ranging from 0-4), and the association between the score and eosinophil counts and risk of asthma, COPD and ACOS was tested. Groups of individuals carrying each genetic risk score were compared to the group with zero risk alleles. In tests for trend, increasing genetic risk score was significantly associated with increasing eosinophil counts (FIG. 2, P=$1\times10^{-39}$) and increasing risk of asthma (FIG. 6, P=$3.27\times10^{-12}$), COPD (FIG. 6, P=$6.65\times10^{-3}$), and ACOS (P=$4.3\times10^{-3}$). The largest effects (exceeding nominal significance) were observed for patients carrying three risk alleles (FIG. 2, for eosinophil counts, Meta beta=0.0071 (0.0057-0.0085) eos/ml, P=$8.8\times10^{-24}$; for asthma (FIG. 6), Meta OR=1.28 (1.17-1.41), P=$6.99\times10^{-8}$; for COPD (FIG. 6), OR=1.17 (1.04-1.31), P=$9.35\times10^{-3}$); and for ACOS (FIG. 6), OR=1.23 (1.03-1.48), P=$2.49\times10^{-2}$ (FIG. 2). Few individuals carried 4 risk alleles, and consequently effect size estimates had wide confidence intervals.

Figure 7:
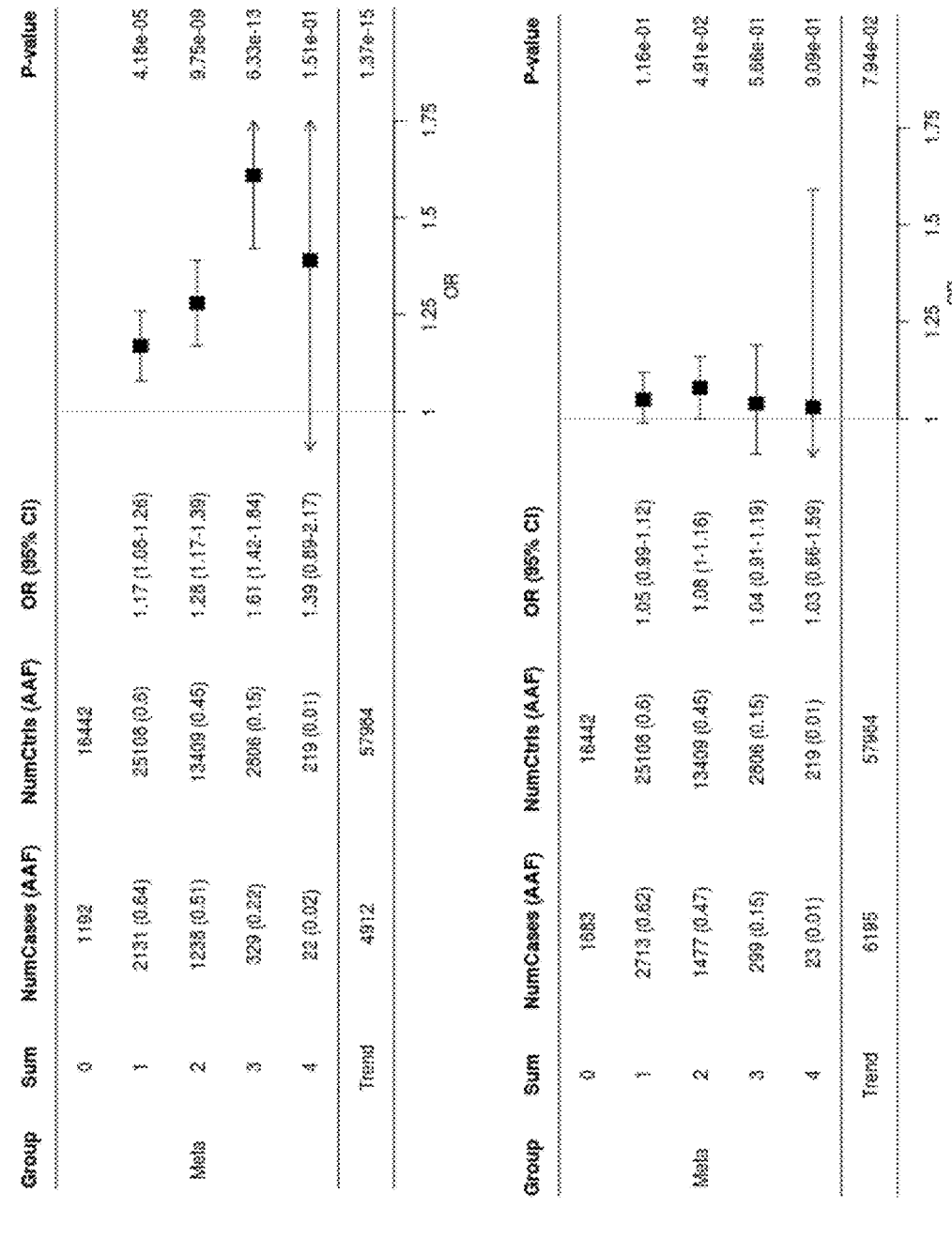
FIG. 7 (Panels A, B, and C) shows genetic score (total burden of rs1420101 and rs1342326 risk alleles) associations with (Panel A) High and Low Eosinophil Asthma (Panel B) High and Low Eosinophil COPD and (Panel C) High and Low Eosinophil ACOS. P-values odds ratios were estimated for individual scores; in each case the comparison was to individuals with zero risk alleles. Additionally, overall trend test p-values are shown.
Figure 7:
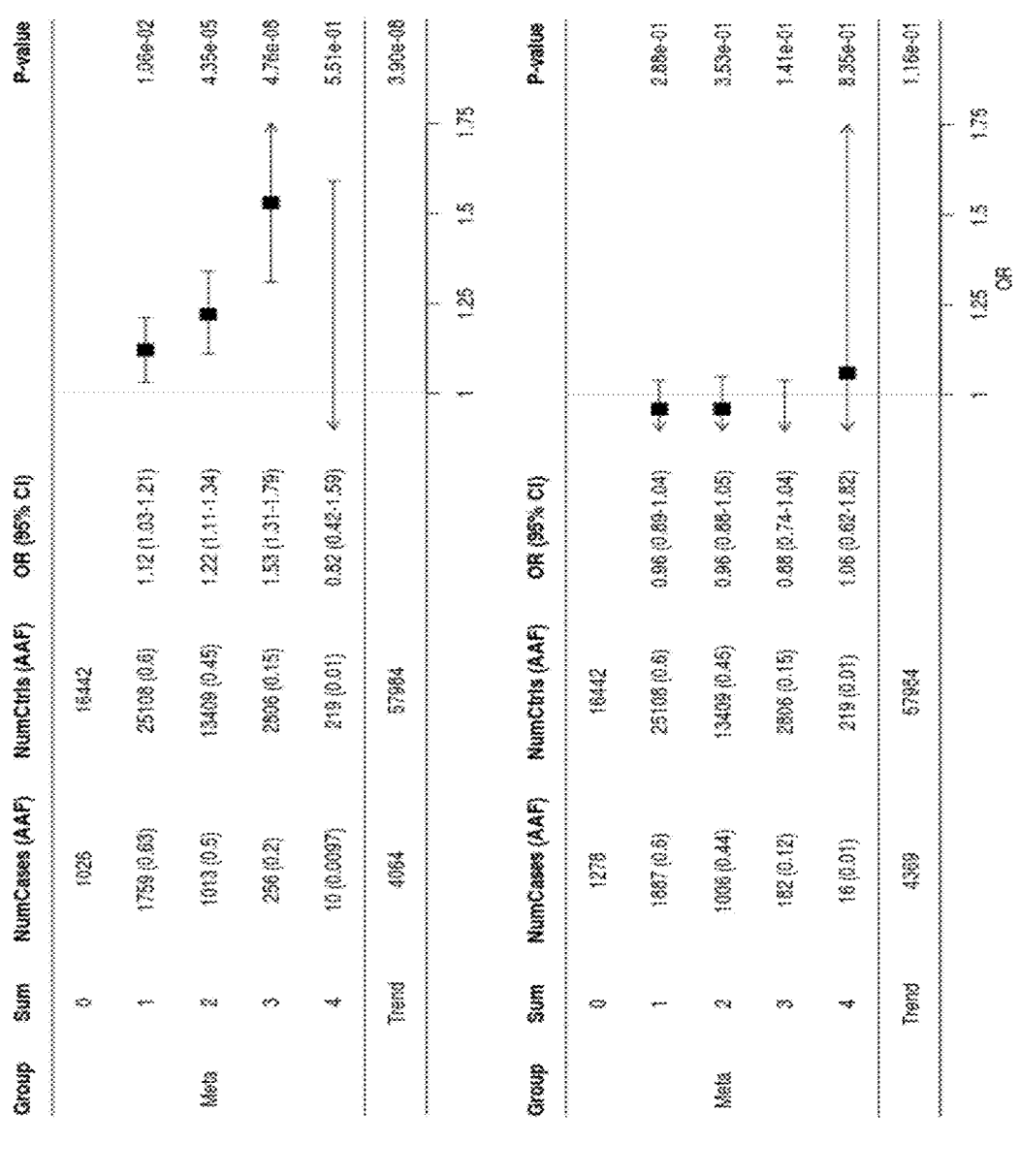
Figure 7:
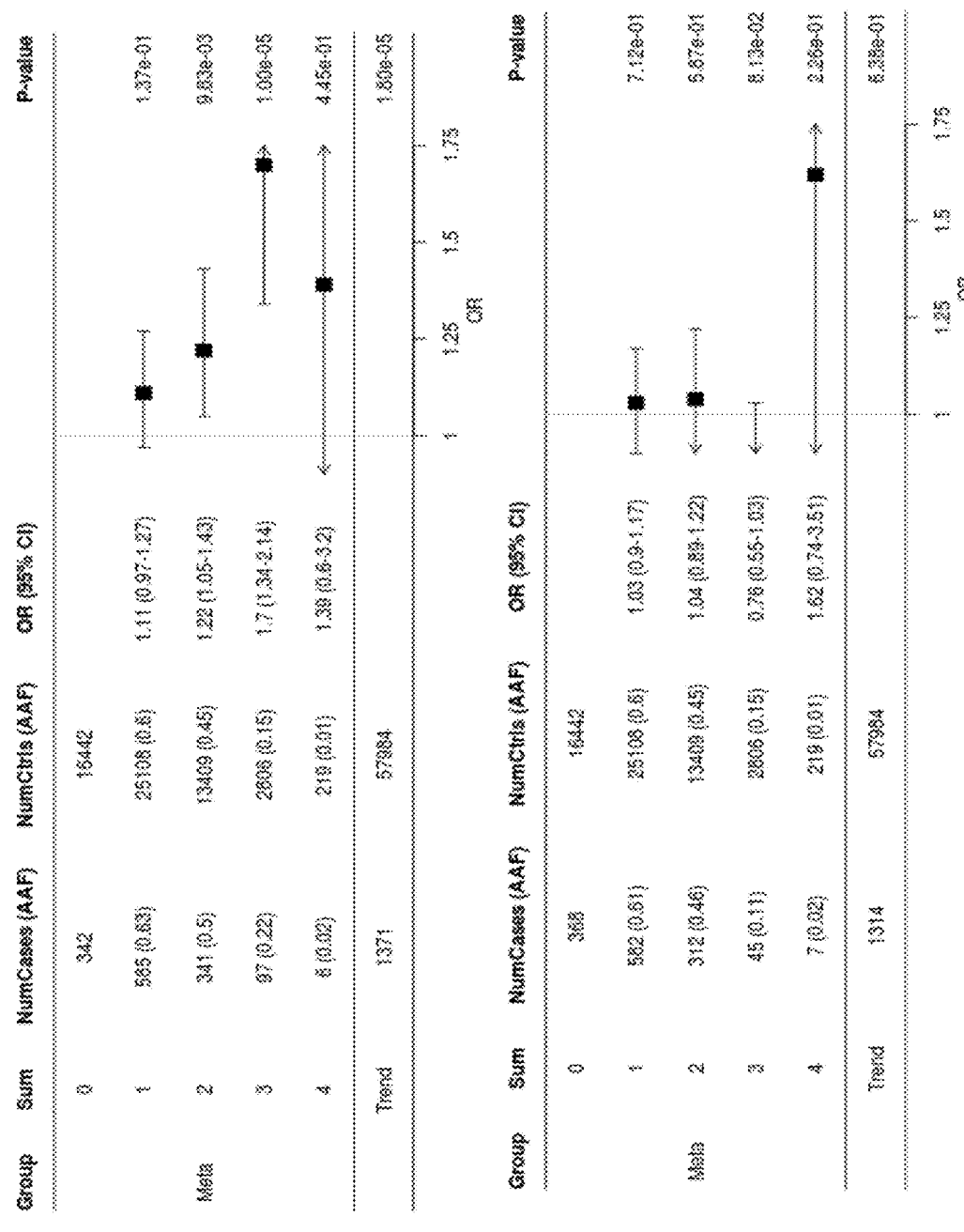

Associations between the two-variant score and high and low eosinophil patient subgroups was also assessed (FIG. 7). In trend tests, the score was significantly associated with high-eosinophil subsets of asthma (P=$1.37\times10^{-15}$), COPD (P=$3.9\times10^{-8}$), and ACOS (P=$1.8\times10^{-5}$), but not with low-eosinophil subsets of asthma, COPD, or ACOS (P>0.05 for each disease). The largest score-specific effects were observed for patients carrying three risk alleles (for high eosinophil asthma, Meta-OR=1.61 (1.42-1.84), P=$6.33\times10^{-13}$; for high eosinophil COPD, Meta-OR=1.53 (1.31-1.79), P=$4.76\times10^{-8}$); and for high eosinophil ACOS, OR=1.7 (1.34-2.14), P=$1\times10^{-5}$. As previously noted, there were relatively few individuals carrying 4 risk alleles, and respective effect size estimates had wide confidence intervals.

Predicted loss-of-function (pLOF) variants in IL33 are associated with decreased circulating eosinophil counts and obstructive lung disease risk. In analyses of IL33 pLOF variant rs146597587, IL33 inactivation is associated with reduced eosinophil counts (Meta-Beta=−0.02 (−0.03-0.0092,P=$7.3\times10^{-5}$) but not significantly with a reduced risk of eosinophilic asthma, COPD and ACOS (OR=0.82 (0.63-1.07), P=0.15, OR=0.99 (0.74-1.33), P=0.94,and OR=0.93

(0.56-1.53), P=0.76, respectively) (FIG. 7). IL1RL1 pLOF variation was not associated with risk of obstructive lung disease.

Analysis of IL1RL1 variant rs1420101 and IL33 variant rs1342326 with other airway diseases. The unified airway theory posits that asthma may co-occur with other airway disease due to common mechanisms. Therefore, other EHR-documented diseases of the airway for association with rs1420101 and rs1342326 were tested (FIG. 9). The IL33 variant rs1342326 and IL1RL1 variant rs1420101 was associated with an increased risk of allergic rhinitis (Meta-OR 1.04 (1.01-1.08), P=0.02; Meta-OR 1.04 (1.01-1.06), P=$2.4 \times 10^{-3}$) as well as an increased risk for nasal polyps (Meta-OR 1.48 (1.28-1.72), P=$1.2 \times 10^{-7}$, Meta-OR 1.17 (1.04-1.33), P=$1.2 \times 10^{-2}$). Furthermore, the burden of these common risk variants also significantly increased the risk for allergic rhinitis and nasal polys (P=$1.45 \times 10^{-4}$, P=$2.48 \times 10^{-7}$). These results are consistent with a previous report implicating IL33 common genetic variation in nasal polyps risk.

Summary. IL33 is thought to be involved in barrier defense in epithelial tissues, including the lung epithelium, and has been implicated in asthma pathogenesis. The two variants described in this Example, IL33 (rs1342326) and IL1RL1 (rs1420101), have been previously associated with asthma in several studies. These reproducible and independent associations (IL33 is located on chromosome 9; IL1RL1 is located on chromosome 2) with both the ligand (IL33) and its specific receptor (IL1R1) suggest a role for IL33 signaling in asthma risk.

The current study significantly extends those previous findings. By performing whole exome sequencing and genotyping in over 83,000 adult participants of the DiscovEHR study associations were confirmed between IL33 and IL1RL1 and eosinophil counts as well as asthma, independently assessed as distinct phenotypes. Furthermore, a suggestive association of the IL33 and IL1RL1 variants with increased risk of COPD and ACOS was demonstrated—providing a genetic link supporting possibility of a shared mechanistic etiology between all three of these highly prevalent lung diseases. Associations of these variants with nasal polyps and allergic rhinitis were also demonstrated. In addition, it was found that in individuals carrying a larger burden of these risk alleles across both loci, larger effects on disease risk were observed. Furthermore, heterozygous carriers of a rare pLOF variants in IL33 had lower median lifetime eosinophil counts and trends reflecting about 20% decreased risk of asthma. It is believed that these data provide genetic evidence linking the IL33 pathway to asthma and possibly to COPD through an allelic series that includes both risk-increasing common alleles and risk-decreasing rare pLOF alleles.

It is believed that prior to this study, genetic variants in the IL33 pathway had not been previously associated with COPD. Similarly, it is believed that there was no prior genetic data linking the any pathway to the risk of the eosinophilic subsets of asthma, COPD and ACOS. The results of this Example suggest a link between enhanced IL33 signaling for increased risk of the eosinophilic subtypes of asthma and COPD and, the numerically higher risk associations seen with ACOS patients suggests that this entity at the intersection of these conditions may indeed have special features. In addition to providing a unifying genetic and mechanistic link between eosinophilic subsets of heretofore distinctly labeled obstructive lung diseases, the data also support the tenets of the "unified airway theory" that posits that eosinophilic lung diseases may represent a continuum with related upper airway diseases. In this respect, a markedly increased risk for the IL33 variant in allergic rhinitis and nasal polyps was observed.

Although not statistically significant, the protective associations with IL33 pLOF variants described in this Example are consistent with a recent study that demonstrated that a rare loss-of-function variant in IL33 was protective in asthma, supporting the possibility that inhibition of IL33 signaling may be an important therapeutic strategy for obstructive lung diseases. The data, in particular, suggest a role for interleukin-33 blockade in the eosinophilic forms of obstructive lung diseases such as asthma and COPD, as well as for eosinophilic upper airway diseases such as allergic rhinitis and nasal polyps.

Relatedly, recent progress with biologics in the treatment of severe and steroid-resistant asthma seems to distinguish eosinophilic disease. Multiple therapies that target interleukin-5 and interleukin-13 seem to only benefit the eosinophilic subset of asthma patients, while an antibody (Dupilumab) that blocks both the interleukin-4 and interleukin-13 pathways has numerically greater benefits in the eosinophilic patients, but also seems to have profound activity in the low-eosinophil subset. These therapies also seem to have benefit in nasal polyps and allergic rhinitis. Consistent with these previously described differences in the responses of eosinophilic asthma patients to biologics therapies, the data from this Example suggests that interleukin-33 blockade might best target the eosinophilic subsets of asthma, ACOS and COPD.

Although this study has certain limitations, it nonetheless represents a real-world clinical care setting, and in this population IL33 and IL1RL1 genetic variation is associated with increased risk of diagnosis of both asthma and COPD. For the purposes of personalized treatment of patients, whether one arrives at a diagnostic label of asthma, COPD, or ACOS is perhaps less important than identifying the mechanistic pathology that is occurring in a particular patient or group of patients, and these data suggest that subsets of asthma, COPD and ACOS patients may in part be driven by excess IL33 activity. Mitigating against various limitations of these data is the remarkable consistency of the findings using genetic variants in two different genes within the same pathway—parallel results were seen for variants in the gene for IL33 as well as for its receptor. For variants in both genes, consistent risk associations were seen across multiple related EHR-defined disease settings, and within these disease settings, consistent results were also repeatedly noted specific to the eosinophilic subsets of these diseases. Another convincing aspect of the data involves the consistent and notable allele-dependence of most of the risk associations, as well as the added power resulting from the two-variant risk score analyses. Finally, the reciprocal findings with the IL33 pLOF variants is also supportive.

These data suggest that genetic variation that enhances IL33 signaling contributes to increased risk of the eosinophilic forms of asthma, COPD and ACOS, and that pLOF genetic variants in IL33 may contribute to reduced risk of these diseases; risk of upper airway diseases such as nasal polyps also appears to be linked to IL33 signaling. Individuals carrying genetic variants that enhance IL33 signaling may represent an opportunity for precision medicine, as those particular asthma and COPD patients may benefit most from therapeutic blockade of IL33. The data also raise the possibility that patients suffering from eosinophilic airway disease, regardless of subtype and variant status, may benefit from inhibition of IL33.

The disclosure is not limited to the embodiments described and exemplified above, but is capable of variation and modification within the scope of the appended claims.

U.S. application Ser. No. 15/827,357 filed Nov. 30, 2017 is incorporated herein by reference in its entirety for all purposes.

We claim:

1. A method for treating or inhibiting eosinophilic asthma-Chronic Obstructive Pulmonary Disease (COPD) overlap syndrome (ACOS), the method comprising administering an IL33 antagonist or a combination of an IL33 antagonist and an IL-4R antagonist to a subject having: i) the IL33 variant rs1342326 but not having the intronic IL1RL1 variant rs1420101; or ii) both the intronic IL1RL1 variant rs1420101 and the IL33 variant rs1342326, wherein the IL33 antagonist comprises an IL33 trap or an antibody, or antigen-binding fragment thereof, that specifically binds to IL33;

wherein the IL33 trap comprises a first IL33 binding domain comprising an IL33 binding portion of IL1RL1 and a second IL33 binding domain comprising an extracellular portion of IL-1RAcP;

wherein the IL33 antibody, or antigen-binding fragment thereof, that specifically binds to IL33 comprises the complementarity determining regions of a heavy chain comprising the amino acid sequence of SEQ ID NO:274 and the complementarity determining regions of a light chain comprising the amino acid sequence of SEQ ID NO:282;

wherein the IL-4R antagonist comprises an antibody, or antigen-binding fragment thereof, that specifically binds to IL-4R and comprises the complementarity determining regions of a heavy chain comprising the amino acid sequence of SEQ ID NO:337 and the complementarity determining regions of a light chain comprising the amino acid sequence of SEQ ID NO:338; and wherein eosinophilic ACOS is treated or inhibited in the subject.

2. The method according to claim 1, wherein the subject has the intronic IL1RL1 variant rs1420101.

3. The method according to claim 1, wherein the subject has the IL33 variant rs1342326.

4. The method according to claim 1, wherein the subject has the IL33 variant rs1342326 and the intronic IL1RL1 variant rs1420101.

5. The method according to claim 1, wherein the IL33 antagonist comprises an IL33 trap.

6. The method according to claim 1, wherein the antibody, or antigen-binding fragment thereof, that specifically binds to IL-4R comprises dupilumab, or antigen-binding fragment thereof.

7. The method according to claim 1, wherein the eosinophilic ACOS comprises a high-eosinophil eosinophilic ACOS.

8. The method according to claim 7, wherein the subject has the intronic IL1RL1 variant rs1420101.

9. The method according to claim 7, wherein the subject has the IL33 variant rs1342326.

10. The method according to claim 7, wherein the subject has the IL33 variant rs1342326 and the intronic IL1RL1 variant rs1420101.

11. The method according to claim 7, wherein the IL33 antagonist comprises an IL33 trap.

12. The method according to claim 7, wherein the antibody, or antigen-binding fragment thereof, that specifically binds to IL-4R comprises dupilumab, or antigen-binding fragment thereof.

\* \* \* \* \*